(12) United States Patent
Vrionis et al.

(10) Patent No.: US 10,799,367 B2
(45) Date of Patent: Oct. 13, 2020

(54) BONE FUSION SYSTEM

(71) Applicants: H. Lee Moffitt Cancer Center and Research Institute, Inc., Tampa, FL (US); University of South Florida, Tampa, FL (US)

(72) Inventors: Frank D. Vrionis, Tampa, FL (US); Kamran Aghayev, Tampa, FL (US); Sabrina A Gonzalez Blohm, Tampa, FL (US); James J. Doulgeris, Oldsmar, FL (US)

(*) Notice: Subject to any disclaimer, the term of this patent is extended or adjusted under 35 U.S.C. 154(b) by 0 days.

(21) Appl. No.: 15/728,898

(22) Filed: Oct. 10, 2017

(65) Prior Publication Data

US 2018/0092751 A1 Apr. 5, 2018

Related U.S. Application Data

(63) Continuation-in-part of application No. 14/347,442, filed as application No. PCT/US2012/058968 on Oct. 5, 2012, now Pat. No. 9,820,788.
(Continued)

(51) Int. Cl.
*A61B 17/86* (2006.01)
*A61F 2/28* (2006.01)
(Continued)

(52) U.S. Cl.
CPC .............. *A61F 2/447* (2013.01); *A61B 17/70* (2013.01); *A61B 17/861* (2013.01);
(Continued)

(58) Field of Classification Search
CPC .......... A61F 2/447; A61F 2/4455; A61F 2/70; A61B 17/84; A61B 17/86; A61B 17/8625;
(Continued)

(56) References Cited

U.S. PATENT DOCUMENTS 4,456,005 A 6/1984 Lichty
4,858,601 A 8/1989 Glisson
(Continued)

FOREIGN PATENT DOCUMENTS

WO 2013052807 A2 4/2013

OTHER PUBLICATIONS

International Preliminary Report on Patentability issued in International Application No. PCT/US2015/043109 dated Feb. 16, 2016.
(Continued)

*Primary Examiner* — Tessa M Matthews
(74) *Attorney, Agent, or Firm* — Meunier Carlin & Curfman LLC

(57) ABSTRACT

A method and system for performing bone fusion and/or securing one or more bones, such as adjacent vertebra, are disclosed. The screw includes a threaded distal piece fixedly attached connected to an inner post. Both the inner post and the proximal piece have non-cylindrical receptacles at their proximal ends for engagement with driving tools. Independent rotation of the proximal piece and the distal piece enables for compression or decompression to modify the gap between two bones or bone fragments. During use, the distal piece of the bone screw is placed at least partially within a distal bone, the proximal piece is placed at least partially within a proximal bone, and one of two pieces is rotated while the other is held in a fixed position, causing movement of the proximal and distal bones relative to each other.

33 Claims, 50 Drawing Sheets

Related U.S. Application Data

(60) Provisional application No. 61/543,482, filed on Oct. 5, 2011.

(51) Int. Cl.
*A61B 17/68* (2006.01)
*A61F 2/44* (2006.01)
*A61B 17/70* (2006.01)
*A61F 2/30* (2006.01)

(52) U.S. Cl.
CPC ........ *A61B 17/863* (2013.01); *A61B 17/8625* (2013.01); *A61B 17/8635* (2013.01); *A61B 17/8665* (2013.01); *A61B 17/8685* (2013.01); *A61F 2/4455* (2013.01); *A61B 17/7059* (2013.01); *A61B 2017/681* (2013.01); *A61F 2002/2835* (2013.01); *A61F 2002/3055* (2013.01); *A61F 2002/30153* (2013.01); *A61F 2002/30261* (2013.01); *A61F 2002/30354* (2013.01); *A61F 2002/30405* (2013.01); *A61F 2002/30471* (2013.01); *A61F 2002/30479* (2013.01); *A61F 2002/30492* (2013.01); *A61F 2002/30505* (2013.01); *A61F 2002/30556* (2013.01); *A61F 2002/30565* (2013.01); *A61F 2002/30579* (2013.01); *A61F 2002/30593* (2013.01); *A61F 2002/30772* (2013.01); *A61F 2002/30836* (2013.01); *A61F 2002/30858* (2013.01); *A61F 2002/30904* (2013.01)

(58) Field of Classification Search
CPC .............. A61B 17/863; A61B 17/8635; A61B 17/8665; A61B 17/8685
See application file for complete search history.

(56) References Cited

U.S. PATENT DOCUMENTS

| | | | |
|---|---|---|---|
| 6,517,543 B1 | 2/2003 | Berrevoets et al. | |
| 7,799,057 B2 | 9/2010 | Hudgins et al. | |
| 8,043,334 B2 | 10/2011 | Fisher et al. | |
| 9,445,848 B2* | 9/2016 | Anderson | A61B 17/7071 |
| 9,482,260 B1 | 11/2016 | Krause | |
| 2002/0195827 A1 | 12/2002 | Jackson et al. | |
| 2004/0122431 A1 | 6/2004 | Biedermann et al. | |
| 2004/0210227 A1 | 10/2004 | Trail et al. | |
| 2005/0043735 A1 | 2/2005 | Ahmad | |
| 2005/0143735 A1 | 6/2005 | Kyle et al. | |
| 2005/0197660 A1 | 9/2005 | Haid et al. | |
| 2005/0261695 A1 | 11/2005 | Cragg et al. | |
| 2005/0277923 A1 | 12/2005 | Sweeney et al. | |
| 2006/0036322 A1 | 2/2006 | Reiley et al. | |
| 2006/0155297 A1* | 7/2006 | Ainsworth | A61B 17/025 606/99 |
| 2007/0270855 A1 | 11/2007 | Partin | |
| 2009/0118771 A1 | 5/2009 | Gonzalez-hernandez | |
| 2009/0254129 A1 | 10/2009 | Tipirneni et al. | |
| 2010/0003638 A1 | 1/2010 | Collins et al. | |
| 2010/0036440 A1 | 2/2010 | Morris et al. | |
| 2010/0049244 A1 | 2/2010 | Cohen et al. | |
| 2010/0082109 A1 | 4/2010 | Greenhalgh et al. | |
| 2011/0034925 A1 | 2/2011 | Tipirneni et al. | |
| 2011/0040329 A1 | 2/2011 | Ainsworth et al. | |
| 2011/0087294 A1 | 4/2011 | Reiley et al. | |
| 2011/0106172 A1* | 5/2011 | Wallenstein | A61B 17/8685 606/286 |
| 2011/0144703 A1 | 6/2011 | Krause et al. | |
| 2011/0224738 A1 | 9/2011 | Sucec et al. | |
| 2011/0282378 A1* | 11/2011 | Murphy | A61B 17/12022 606/195 |
| 2011/0319946 A1* | 12/2011 | Levy | A61B 17/7035 606/309 |
| 2013/0006361 A1 | 1/2013 | Glerum et al. | |
| 2013/0053902 A1 | 2/2013 | Trudeau et al. | |
| 2013/0211526 A1 | 8/2013 | Alheidt et al. | |
| 2013/0231747 A1 | 9/2013 | Olmos et al. | |
| 2013/0325075 A1 | 12/2013 | Jackson et al. | |
| 2014/0114312 A1 | 4/2014 | Krause | |
| 2014/0142639 A1* | 5/2014 | Vennard | A61B 17/8685 606/291 |
| 2014/0172027 A1* | 6/2014 | Biedermann | A61B 17/866 606/326 |
| 2014/0188180 A1* | 7/2014 | Biedermann | A61B 17/8625 606/328 |
| 2015/0012048 A1 | 1/2015 | Huebner et al. | |
| 2016/0310190 A1 | 10/2016 | Gonzalez Blohm et al. | |
| 2018/0071000 A1 | 3/2018 | Pham et al. | |
| 2018/0092677 A1 | 4/2018 | Peterson et al. | |
| 2018/0206897 A1* | 7/2018 | Palmer | A61B 17/866 |
| 2019/0046328 A1 | 2/2019 | Rosenwasser et al. | |

OTHER PUBLICATIONS

International Search Report and Written Opinion issued in International Application No. PCT/US2015/043109 dated Nov. 2, 2015.
International Search Report and Written Opinion issued in International Application No. PCT/US2012/058968 dated Mar. 28, 2013.
International Search Report and Written Opinion issued in International Application No. PCT/US2014/070899 dated May 14, 2015.
International Preliminary Report on Patentability and Written Opinion Issued in International Application No. PCT/US2014/070899 dated May 14, 2015.
Zimmer® Herbert™ Cannulated Bone Screw, Webpage, http://www.zimmerbiomet.com/content/dam/zimmer-biomet/medical-professionals/000-surgical-techniques/trauma/zimmer-herbert-cannulated-bone-screw.pdf, dated Jul. 27, 2015, accessed Jan. 2, 2018.
Co-Pending U.S. Appl. No. 15/500,969, filed Feb. 1, 2017.
Co-Pending U.S. Appl. No. 15/105,210, filed Jun. 16, 2016.
Co-Pending U.S. Appl. No. 15/718,786, filed Sep. 28, 2017.
Co-Pending U.S. Appl. No. 15/970,204, filed May 3, 2018.
Co-Pending U.S. Appl. No. 15/970,212, filed May 3, 2018.
Final Office Action issued in U.S. Appl. No. 15/718,786, dated Mar. 19, 2020.

* cited by examiner

BONE FUSION SYSTEM

CROSS REFERENCE TO RELATED APPLICATIONS

This application is a continuation-in-part of U.S. patent application Ser. No. 14/347,442, filed Mar. 26, 2014, which is a 35 U.S.C. § 371 national phase entry of PCT Application No. PCT/US2012/058968, filed Oct. 5, 2012. PCT Application No. PCT/US2012/058968 claims the benefit of priority to U.S. Provisional Application No. 61/543,482, filed Oct. 5, 2011. Each of these applications are incorporated by reference in their entireties for all purposes.

FIELD

This invention relates to neurosurgical and orthopedic fixation systems and more particularly to bone fusions.

BACKGROUND

Spinal interbody fusion is frequently performed procedure to treat various disorders such as degenerated disk disease, spondylolisthesis, trauma, infection, tumor and deformity. Usually, surgery involves placement of screws into the vertebral body through the vertebral pedicle and/or placement of an interbody cage with bone grafts into the disc space. Types of spinal fusion depend on the approach type such as posterior, transforaminal, lateral, etc. Although these approaches claim to be minimally invasive, they still require open incisions for cage and screw placement. For example, to perform one level interbody fusion the surgeon must perform an incision to perform discectomy and insert a cage, then four incisions to insert pedicle screws and then two more incisions to pass rods and stabilize screws to rods.

During spine stabilization operations a certain degree of compression or distraction is usually applied to stabilized vertebrae depending on the condition. Compression is usually performed on the concave side of the scoliotic deformity to correct it.

Distraction on the other hand is opposite to compression and is performed usually to decompress vulnerable structures that travel between vertebrae, i.e. nerve roots. Distraction is usually performed so as to increase the gap between vertebral bodies to decompress nerve roots escaping from neural foramina. It is also performed on the convex side of scoliotic deformity.

Improvements in fusion, compression and distraction methods and devices are therefore desired.

SUMMARY

Implementations of the present disclosure overcome the problems of the prior art by providing a bone screw including a threaded proximal piece, a threaded distal piece, and an inner post extending through the proximal piece and fixedly attached to the distal piece. The distal piece includes an external surface defining a set of threads and, in some implementations, the distal piece has a smaller diameter than the proximal piece.

The proximal piece includes a proximal head, a body, and a set of threads defined on an external surface of the body. Furthermore, the proximal piece defines a central lumen. A proximal end surface of the proximal head of the proximal piece defines a first non-cylindrical receptacle that extends axially into the proximal head. In some implementations, the proximal head of the proximal piece comprises a semi-spherical outer surface.

In some implementations, the set of threads of the proximal piece have the same pitch as the set of threads of the distal piece. The threads of the proximal and distal pieces can also include notches for facilitating tapping procedures. The first and second sets of threads can be angled in the same direction, or they can be angled in opposing directions (i.e., the first set of threads is angled toward the proximal head, and the second set of threads is angled toward a distal end of the bone screw).

The inner post includes a shaft that extends through the central lumen of the proximal piece and is fixedly attached to the distal piece, for example via welding or pins. The inner post also includes a proximal head that abuts an inner distal surface of the first non-cylindrical receptacle. In some implementations, an outer surface of the proximal head is cylindrical. A proximal end surface of the proximal head of the inner post defines a second non-cylindrical receptacle that extends axially into the proximal head of the inner post. In some implementations, axial movement of the proximal piece along the shaft of the inner post is restricted between a proximal end of the distal piece and the proximal head of the inner post.

The proximal piece is configured to be rotated separately from the distal piece via engagement of the first non-cylindrical receptacle, and the distal piece is configured to be rotated separately from the proximal piece via engagement of the second non-cylindrical receptacle. In some implementations, the first non-cylindrical receptacle has a hexagonally shaped cross-sectional shape. In some implementations, the second non-cylindrical receptacle has a hexagonally shaped cross-sectional shape.

Methods of moving a first bone in relation to a second bone are also disclosed herein. The methods can be used, for example, in compression or decompression procedures. The methods include positioning a distal piece of a bone screw at least partially within a distal bone, positioning a proximal piece of a bone screw at least partially within a proximal bone, and rotating one of the proximal or distal pieces of the bone screw while holding the other of the proximal or distal pieces of the bone screw in a fixed position. This motion moves one of the proximal or distal bones in relation to the other of the proximal or distal bones. In some implementations, the bone screw is cannulated to enable sliding over a guidewire during the positioning step. Other devices, such as a bone plate, a tulip, or a cage can be used in conjunction with the bone screw.

DETAILED DESCRIPTION OF THE INVENTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

A method and system for performing bone fusion and/or securing one or more bones are disclosed. One or more screws of the system are configured to enable compression and distraction to modify the gap between the vertebral bodies. An intervertebral cage of the system is configured for lateral expansion from a nearly straight configuration to form a large footprint in the disc space.

Generally, for fusion, adjacent vertebrae are stabilized non-invasively without prior destabilization using bilateral screw placement and an expanding cage, both of which can be combined with the use of bone filling. Screws are passed from the inferior to superior vertebra, for example, through a trans-pedicular route so as to avoid neurological compromise. At the same time, the path of screw insertion is oriented to reach superior vertebra.

The cage of the system provides a structural component for forming a bony bridge, such as through the use of bone grafting materials, between the vertebrae. The cage is configured for minimally invasive insertion, such as through a small annulotomy and subsequent cage expansion. This provides a large surface area to prevent subsidence and facilitate fusion with reduced disc removal.

The systems and methods also provide the surgeon an ability to perform compression and/or distraction maneuvers during different neurosurgical and orthopedic procedures with a predictable amount of compression/distraction in terms of both distance and force. Although described in the context of vertebrae, it should be noted that none of the implementations described herein are limited to any particular anatomical bone structure. The bone screws, cages and other components described herein may be used on any number of bones or bone fragments, such as a tibia, skull, etc.

Figure 1:
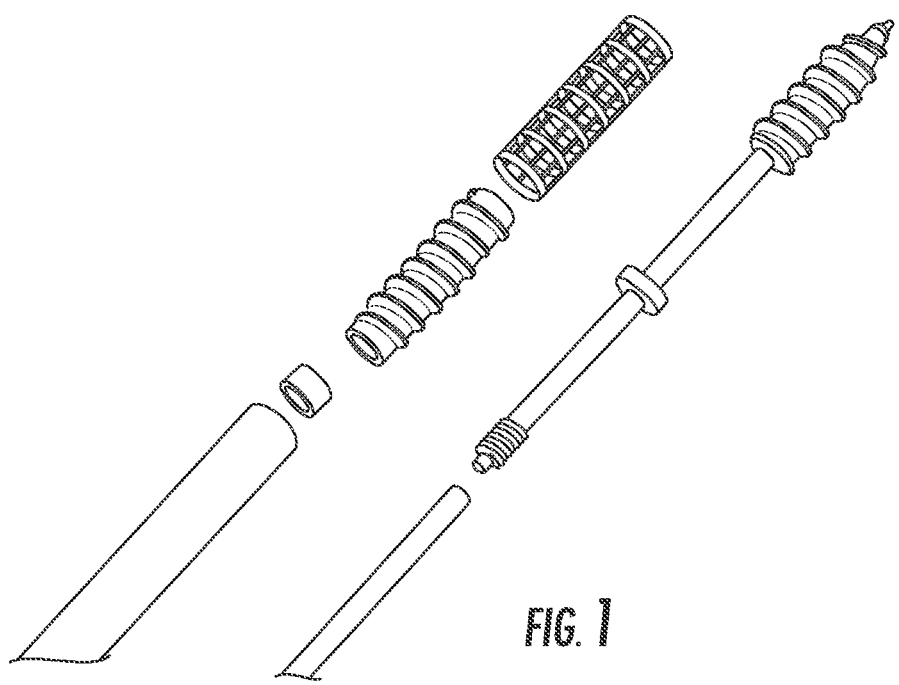
FIG. 1 is a perspective view of a bone screw and drivers.
Figure 2:
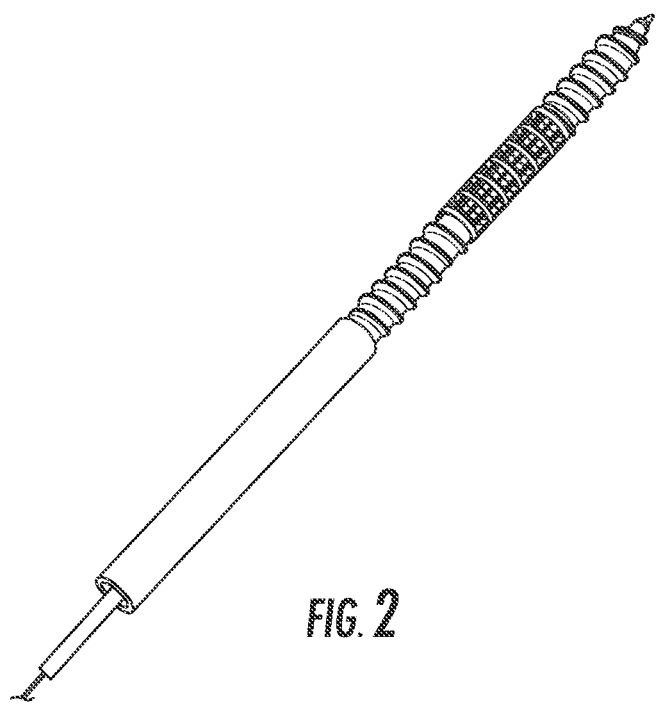
FIG. 2 is a perspective view of an assembled bone screw from FIG. 1.

As shown in FIGS. 1-2, a bone screw 10 includes a threaded tip 12, a main shaft 14 and a threaded outer sleeve 16. The bone screw 10 may also include a cage 32 and a fastener 58.

Figure 12:
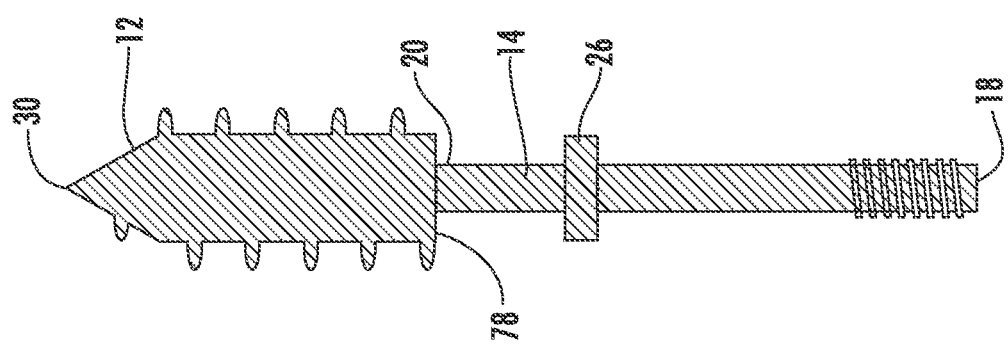
FIG. 12 is a schematic of a threaded distal tip and a main shaft of a bone screw.

As shown in FIGS. 1-2 and 12, the threaded tip 12 includes a proximal end 28 and a distal end 30. The proximal end 28 is configured for attachment of the main shaft 14, such as by having a threaded axial opening configured to receive a threaded end of the main shaft 14. The distal end 30 has a point that is configured for driving into bone, such as through an existing tapped or drilled hole in the bone, as will be shown below.

The proximal end 28 has a shape and diameter that generally matches an outer shape and diameter of the cylindrical cage 32 and/or a distal end 24 of the threaded outer sleeve 16. The proximal end 28 tapers to the point at the distal end 30. This can facilitate enlargement of the opening in the bone for subsequent passage of the remainder of the screw 10. The outer diameter of the proximal end 28, however, may also be larger than some internal diameter of the cylindrical cage 32, so that it does not slip distally off of the threaded tip 12.

As shown in FIGS. 1-2 and 12, the main shaft 14 includes a proximal end 18 and a distal end 20 and is attached to the threaded tip 12 and extends proximally therefrom. Such attachment can be by threaded insertion into the threaded tip 12, separate construction and later permanent attachment (e.g., welding) or may be integrally formed with the threaded tip 12. The main shaft 14 has a diameter that is configured to fit through axial openings extending through the remaining components of the screw 10.

The main shaft 14 at its proximal end 18 has a threaded portion with a relatively high number of threads per inch. The proximal end 18 also defines a driver interface, such as a non-circular shaped receptacle or a non-cylindrical outer shape (e.g. square or hexagonal) that is configured to accept or slide into a driver for rotational advancement of the main shaft 14 with the threaded tip 12 at its distal end.

The main shaft 14 may also include a stop member 26 coupled thereto. The stop member 26, for example, may be an annular ring positioned about half way between the proximal end 18 and the distal end 20, as shown in FIG. 1. The stop member 26 may be separately attached or integrally formed with the main shaft 14. Other shapes are possible for the stop member 16, including shapes that match an outer shape and max diameter of the threaded outer sleeve 16 at its distal end 24 or a proximal end 34 of the cylindrical cage 32 so as to facilitate its passage through a bone opening. Generally, the stop member 26 is configured to act as a stop for distal travel of the threaded outer sleeve 16 over the main shaft 14 and therefore should have a larger diameter and/or incompatible shape with respect to an axial opening 26 of the threaded outer sleeve 16.

As shown in FIG. 1, the cage 32 includes the proximal end 34 and a distal end 36. The cage 32 has a shape (e.g., cylindrical) and outer diameter that is configured to trail the proximal end 28 of threaded tip 12 smoothly upon insertion. The cage 32 has defined axially, between the ends 34, 36, an opening that is configured to allow its passage over the main shaft 14 and possibly the stop member 26 to abut (by being somewhat smaller than a maximum diameter of) the proximal end 28 of the threaded tip 12. Other cage shapes are also possible, such as a square or non-cylindrical cross-section, wherein the shapes are configured to receive bone graft material or bone growth promoting materials such as bone morphogenic protein (BMP).

The cage defines lateral or side holes or openings 38 which allow bone growth promoters held within the cage to leak, diffuse or otherwise access (or be accessed by) adjacent bone structures so as to promote fusion. The lateral openings may be, for example, square openings when the cage 32 is formed of axially aligned rings connected by radially spaced longitudinals. The lateral openings 38 may also be other shapes and distributions, such as cylindrical openings or irregularly shaped and placed openings.

The distal end 36 of the cage 32 may include one or more locking surfaces configured to mate with a corresponding locking surface on the proximal end 28 of the threaded tip 12.

As shown in FIGS. 1-12 and 13, the threaded outer sleeve 16 has a proximal end 22 and the distal end 24. The axial opening 26 is defined axially through the threaded outer sleeve 16 and extends between the proximal and distal ends 22, 24 of the outer sleeve. The axial opening 26 has a diameter sufficient to receive and allow passage of the proximal end 18 of the main shaft 14. And, the threaded outer sleeve 16 is configured to extend over and allow the threaded outer sleeve 16 to freely rotate about the proximal end 18 of the main shaft 14.

The threaded outer sleeve 16 may have threads that match the threads of the threaded tip 12 and a maximum and minimum diameter that are the same as the diameters of the proximal end 28 of the threaded tip 12. The threaded outer sleeve 16 may also have a larger diameter (maximum or minimum) than the diameter of the threaded tip 12 to facilitate rotational locking and/or secure fixation of the threaded outer sleeve 16.

Figure 14:
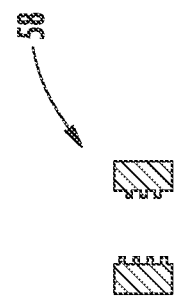
FIG. 14 is a schematic of a fastener.
Figure 13:
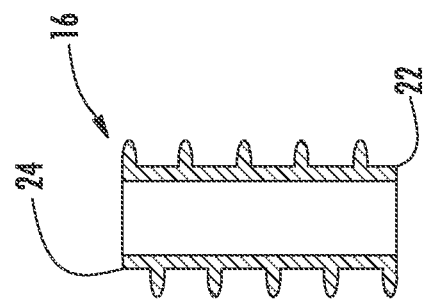
FIG. 13 is a schematic of a threaded outer sleeve.

As shown in FIGS. 1-2 and 14, the fastener 58 is a nut having a threaded inner opening and outer driving surfaces. The fastener 58 is configured for attachment to the proximal end of the main shaft 14 and engagement of the threads thereon to lock the threaded outer sleeve 16 against the stop member 26.

Figure 4:
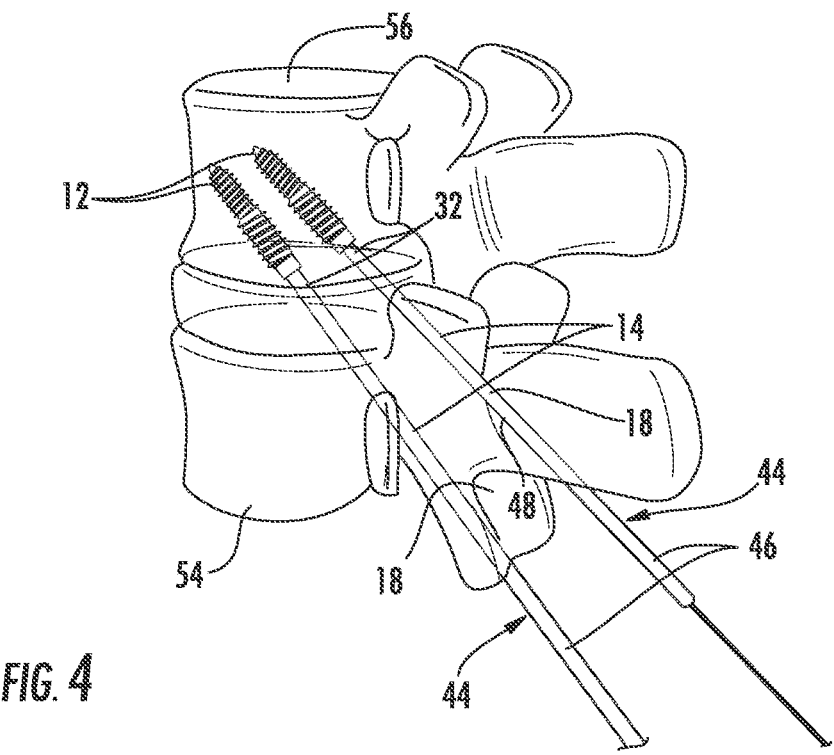
FIG. 4 is a perspective view of a threaded distal tip of a bone screw and a cage and a main shaft sleeved over each of the guide wires of FIG. 3.

As shown in FIG. 4, the threaded tip 12 and the main shaft 14 may define a central wire opening for passage over a guide or working wire 40.

Figure 18:
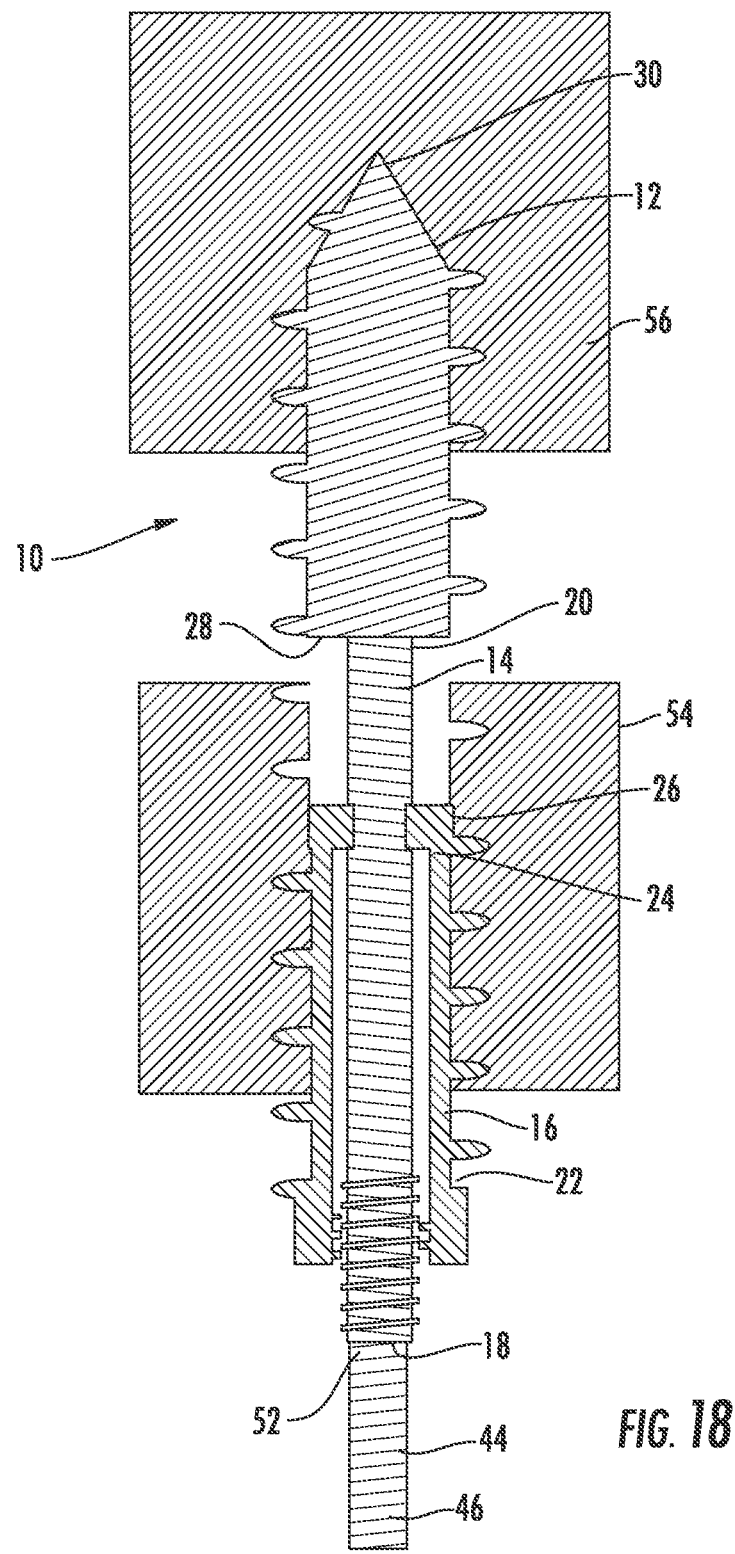
FIG. 18 is a schematic of driving of a bone screw into the tapped hole of FIG. 17.
Figure 19:
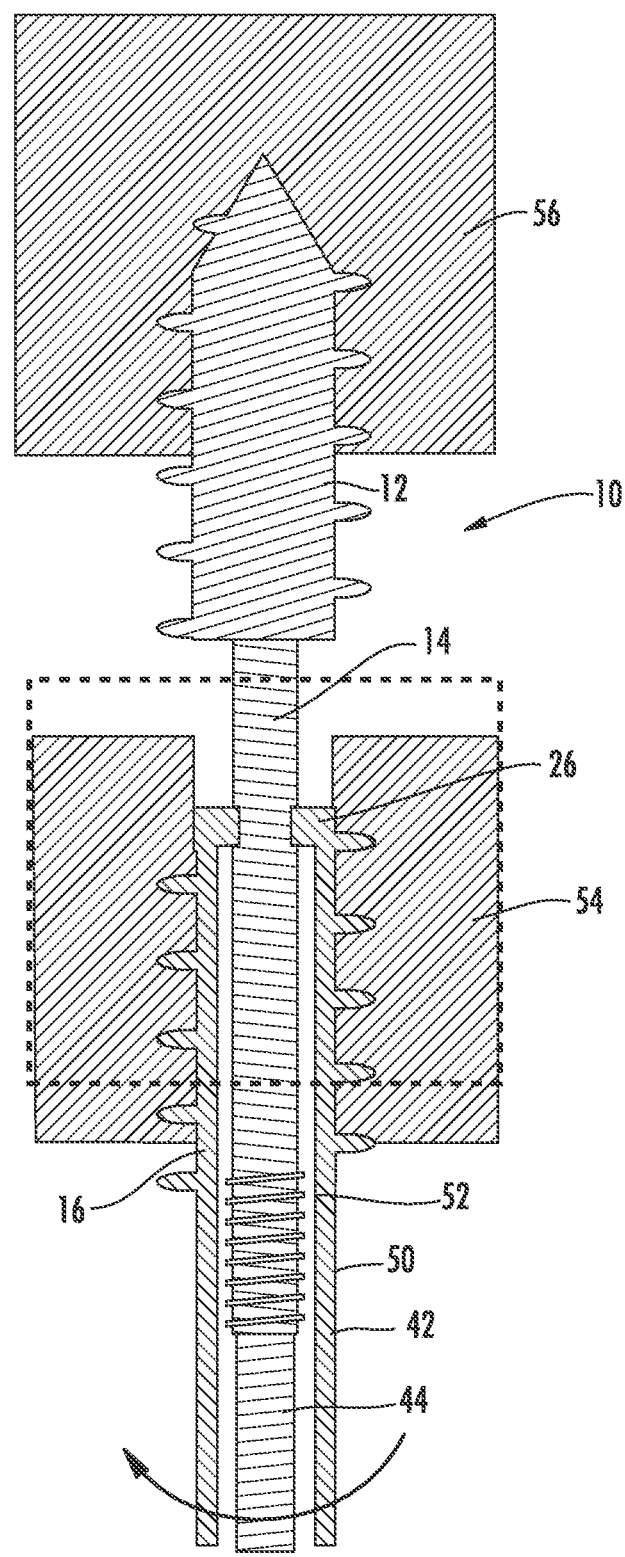
FIG. 19 is a schematic of distracting the two bones of FIG. 18 apart by rotating an outer sleeve of the bone screw.

As shown in FIGS. 18 and 19, the system may also include an outer driver 42 and an inner driver 44. The inner driver 44 has a driving shaft 46 and a driving tip 48 that is configured to mate with the driving surfaces or opening on the proximal end 18 of the main shaft. At its proximal end (not shown) the inner driver 44 (and the outer driver 42) may have a grip or handle configured for hand driving and/or be configured to mate to a motorized driver.

The outer driver 42 includes a tubular shaft 50 and a driving tip 52. The tubular shaft 50 of the outer driver 42 is configured to sleeve over the proximal end 22 of the main shaft. The driving tip 52 is configured to mate with the driving surfaces of the proximal end 22 of the threaded outer sleeve 16 and/or with the driving surfaces of the fastener 58. In this manner, the outer driver 42 is configured to advance the fully assembled bone screw 10.

Figure 15:
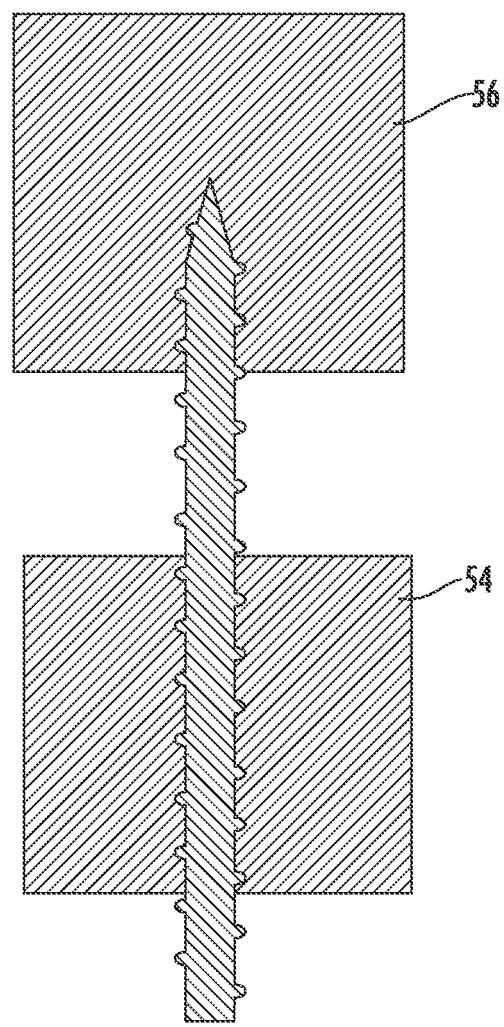
FIG. 15 is a schematic of drilling a pilot hole into two bones.
Figure 16:
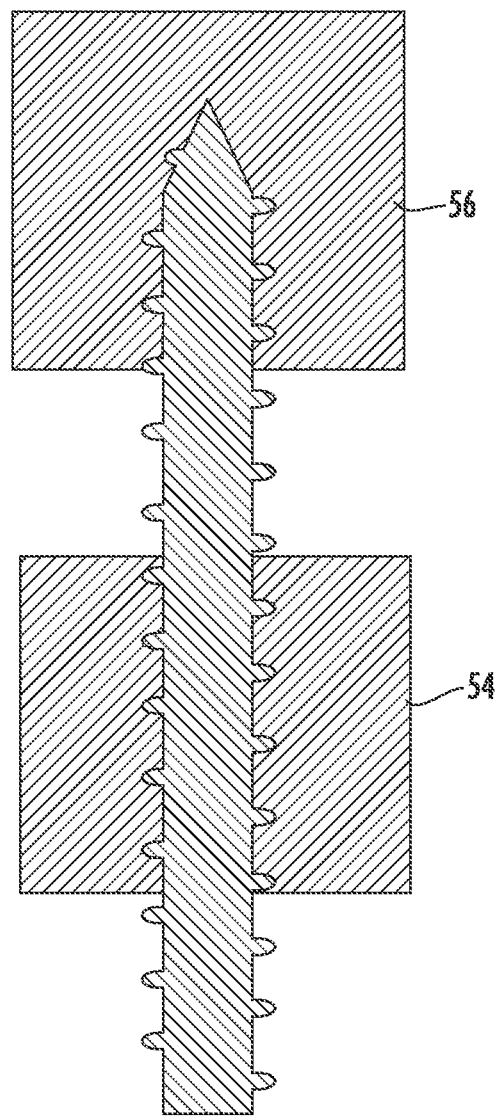
FIG. 16 is a schematic of reaming or tapping of the two bones of FIG. 15.
Figure 17:
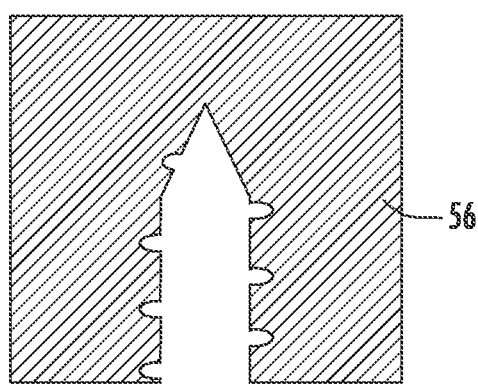
FIG. 17 is a schematic of the two bones of FIG. 16 after tapping is completed.
Figure 17:
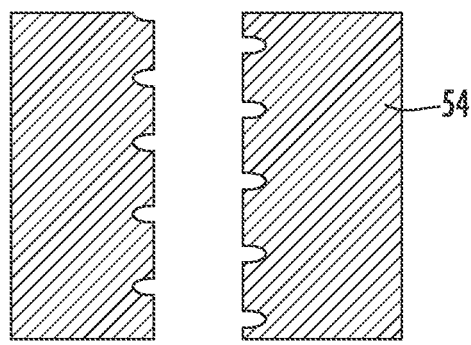

FIGS. 15-22 show use of the bone screw 10 to connect and/or compress or distract an inferior vertebra 54 and a superior vertebra 56. As shown in FIG. 15, a pilot hole is formed by use of a small drill bit which advances first through the inferior vertebra 54 and into the superior vertebra 56. As shown in FIGS. 16 and 17, the pilot hole is reamed with a remaining drill bit that is oversized relative to the small drill bit. The reamed hole approximates the diameter and thread pitch of the bone screw 10 components for easier insertion.

As shown in FIG. 18, the assembled screw 10, including threaded outer sleeve 16 sleeved over the main shaft 14 up to and abutting the stop member 26 and locked against the stop member 26 by the attached fastener nut 58, is advanced through the inferior vertebra 54 and the superior vertebra 56 using the inner driver 44. Notably, once the screw 10 is assembled and locked, the cylindrical threaded outer sleeve 16 is locked between the nut 58 and the stop member 26 on the main shaft 14 and is functioning as a regular screw.

As shown in FIG. 19, the fastener nut 58 has been removed (allowing the cylindrical threaded outer sleeve 16 to turn around the main shaft) and the outer driver 42 is engaged to the proximal end 22 of the threaded outer sleeve 16. While the inner driver 44 holds the main shaft 14 still, the outer driver 42 is rotated clockwise against the stop member 26 to distract the inferior vertebra 54 away from the superior vertebra 56.

Figure 20:
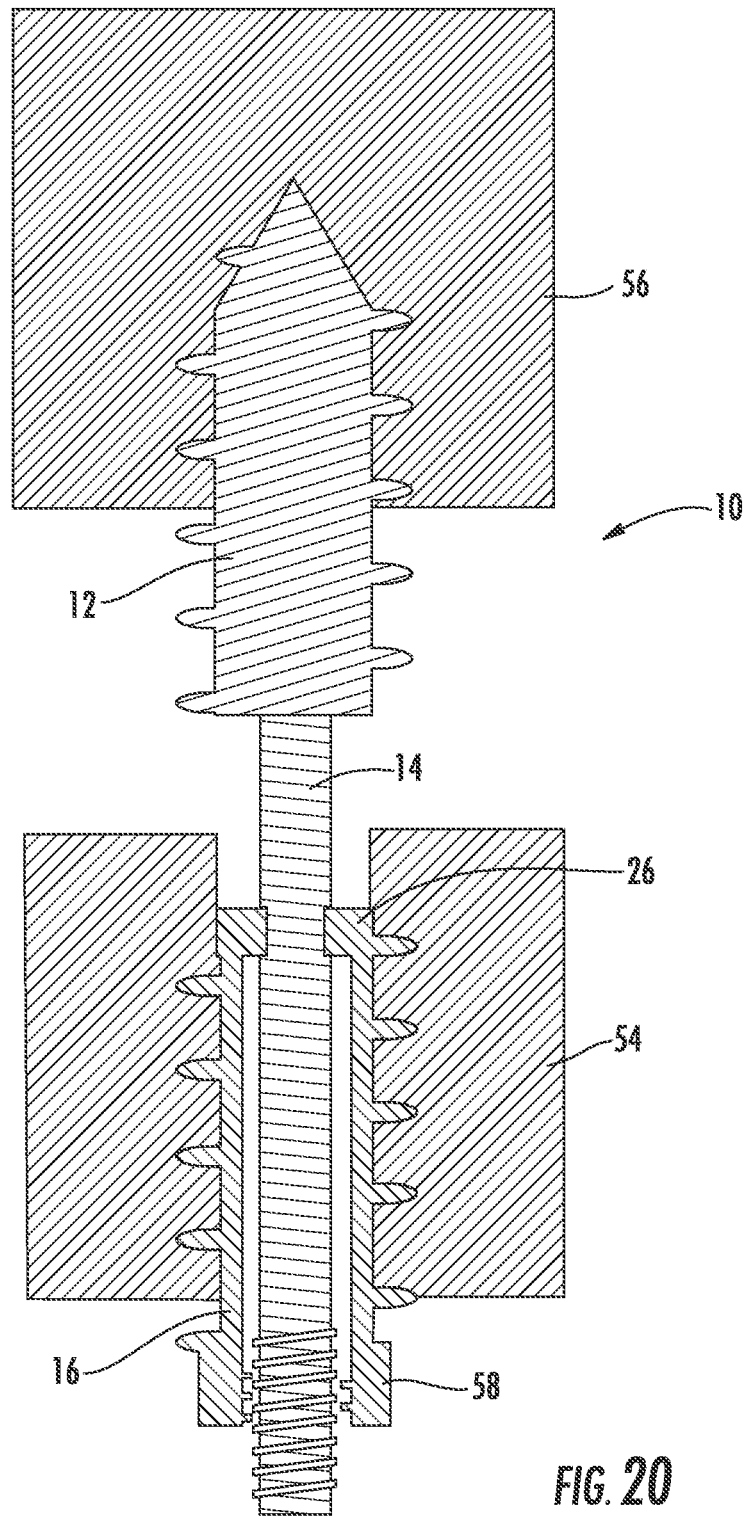
FIG. 20 is a schematic of attaching a fastener to the bone screw of FIG. 19 after distraction.

As shown in FIG. 20, once the desired distraction distance is accomplished, the fastener nut 58 is reattached to the proximal end 18 of the main shaft 14. This stops relative rotation of the sleeve 16 and the main shaft 14 and hence motion between the vertebrae 54, 56.

Figure 21:
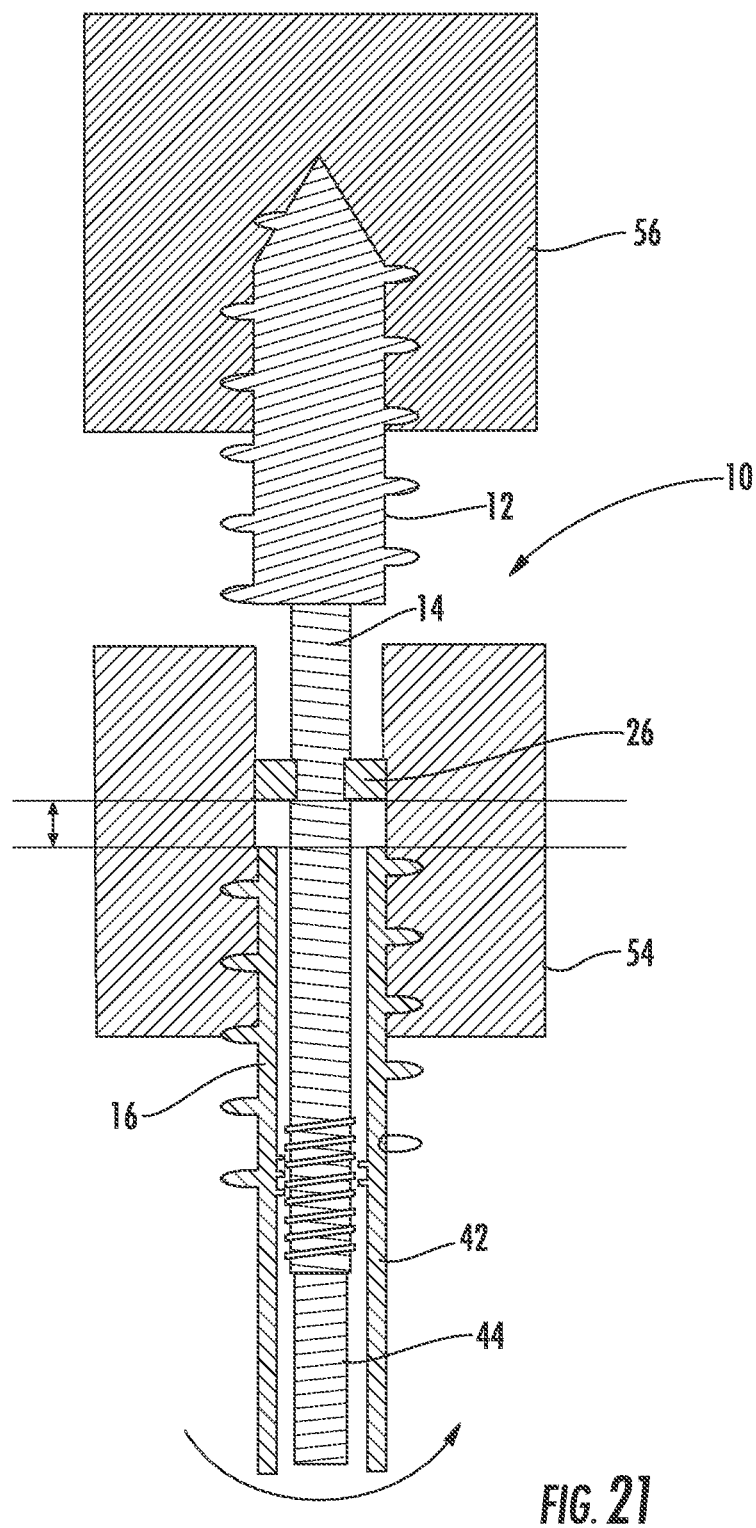
FIG. 21 is a schematic of compressing the two bones of FIG. 18 together by rotating an outer sleeve of the bone screw.
Figure 22:
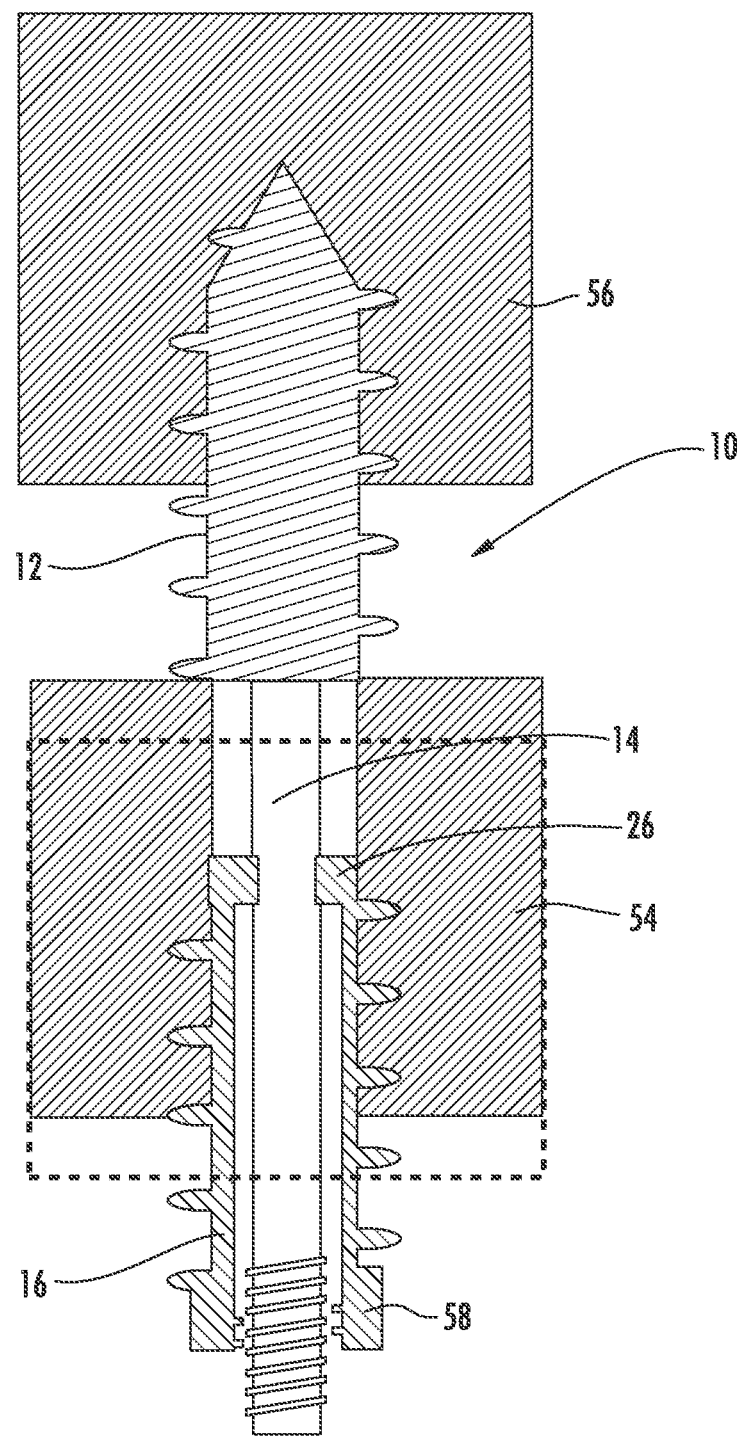
FIG. 22 is a schematic of attaching a fastener to the bone screw of FIG. 21 for further compression.

As shown in FIG. 21, the vertebrae 54, 56 (or other bones as the case may be) can be compressed relative to each other. The inner driver 44 holds the main shaft 14 still and the outer driver 42 is rotated counter-clockwise away from the stop member 25. Then, as shown in FIG. 22, the fastener nut 58 is attached to the proximal end 18 of the main shaft and as it is advanced thereon, the cylindrical outer sleeve 16 is advanced toward the stop member 26 and the vertebrae 54, 56 are compressed toward each other.

Figure 3:
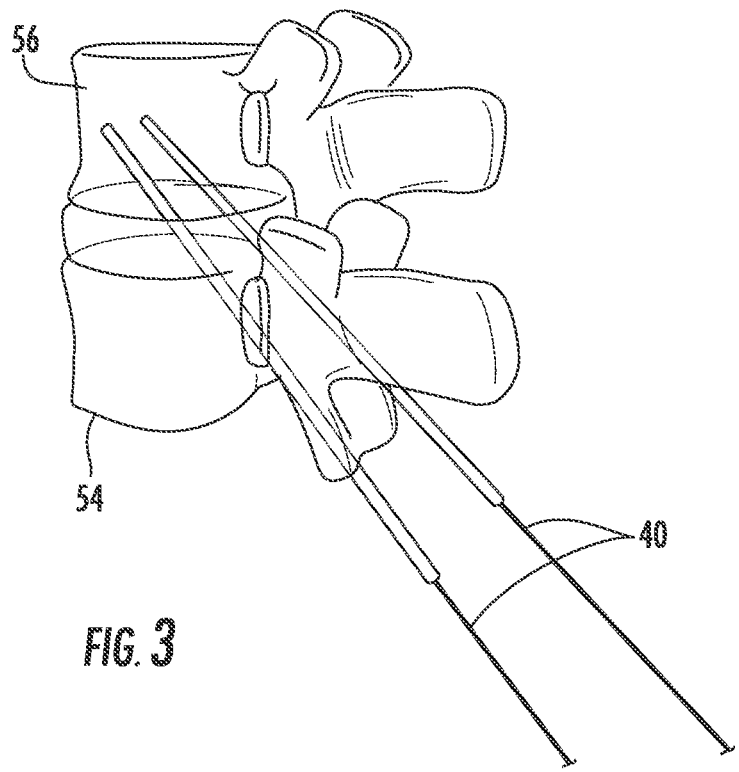
FIG. 3 is a perspective view of bilateral insertion of two needles and guide wires into two adjacent vertebrae and through a disc space.

As shown in FIG. 3, several screws 10 may be deployed to bridge two vertebrae 54, 46 across the disc space at an angle using a posterior approach or a bilateral, transpedicular approach. As shown in FIG. 3, the driving direction is an inferior to superior trajectory starting with two small 1 cm incisions in the lumbar regions. A JAMSHIDI needle is inserted through each of the incisions at the desired angle, the stylet removed and a K-wire inserted through the central opening of the needle. The needle is then removed.

Figure 5:
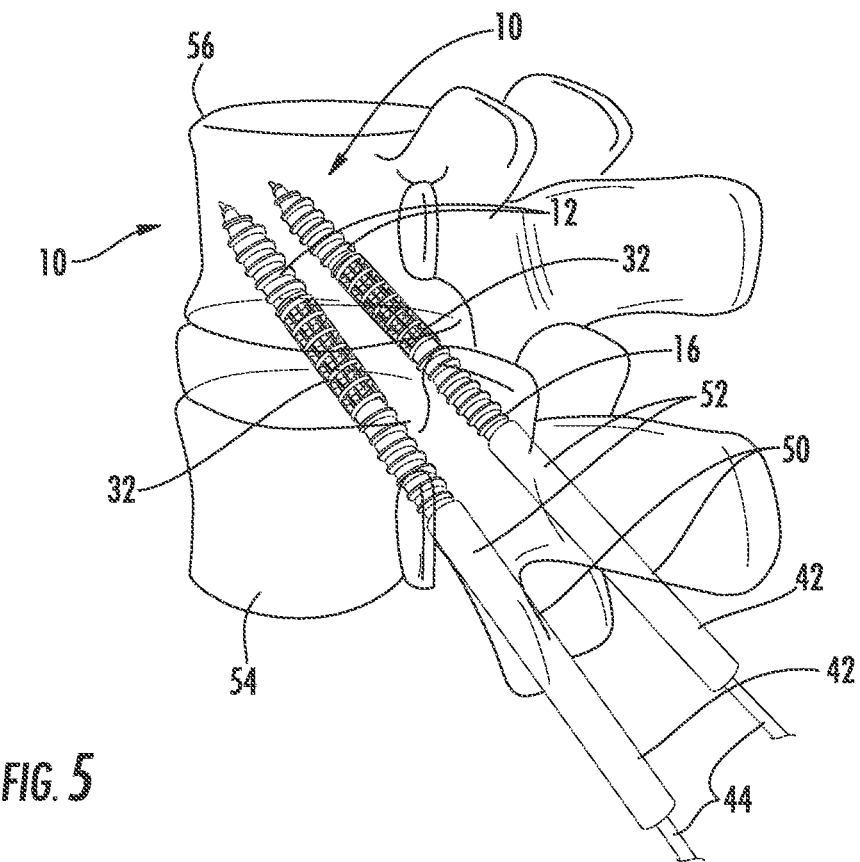
FIG. 5 is a perspective view of the bone screws of FIG. 4 with a threaded sleeve.

As shown in FIG. 4, the threaded tip 12, the main shaft 14 and the cylindrical cage 32 are advanced, using the inner driver 44, over the K-wire through the inferior vertebra 54, the disc space and into the superior vertebra 56. The cylindrical cage 32 may have been packed with a bone graft and/or fusion material that can communicate through holes in the cage. As shown in FIG. 5, the outer driver 42 is engaged on the threaded outer sleeve 16 and over the main shaft 14 to drive the threaded outer sleeve through the hole in the inferior vertebra 54.

Figure 6:
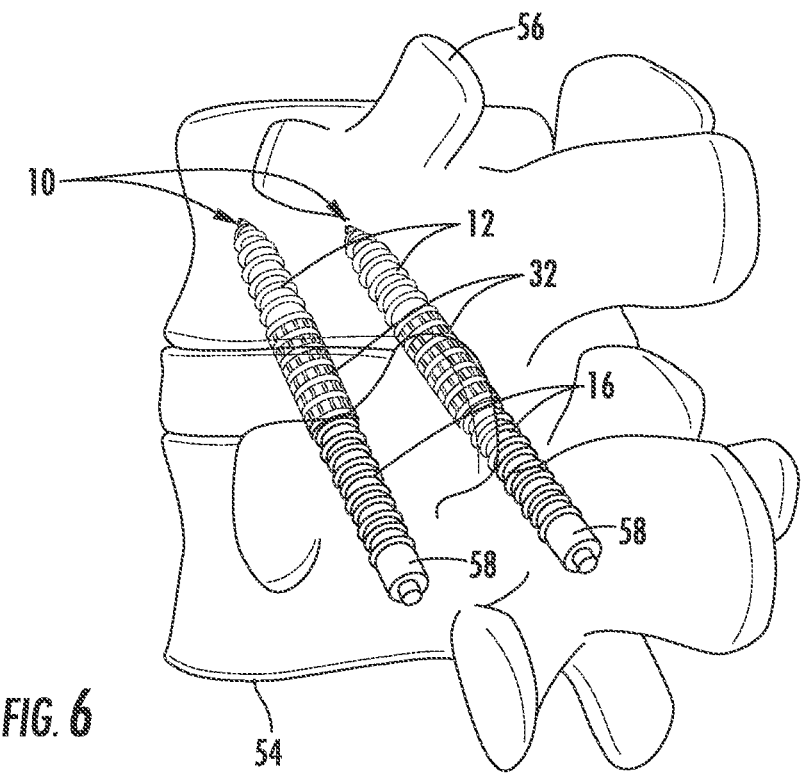
FIG. 6 is a perspective view of the bone screws of FIG. 5 with fasteners attached to their proximal ends.

As shown in FIG. 6, the locking nut 58 is attached to the main shaft 14 and the K-wire is withdrawn.

Figure 7:
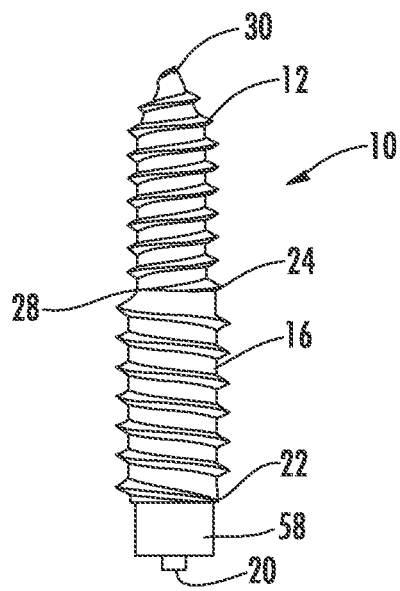
FIG. 7 is an anti-rotation bone screw.

As shown in FIG. 7, the screw 10 may also include an oppositely threaded outer sleeve 16. The main shaft 14 includes no stop member 26 and has at its end attached the locking nut 58 to form a solid screw. Attachment of the threaded outer sleeve 16 is facilitated by its initial ability to freely rotate about the main shaft 14 once the threaded tip 12 and main shaft 14 are inserted into a bone. Then, reverse-threaded outer sleeve 16 can be counter rotated until it advances to the proximal end of the threaded tip 12. The locking nut 58 is then attached.

Figure 23:
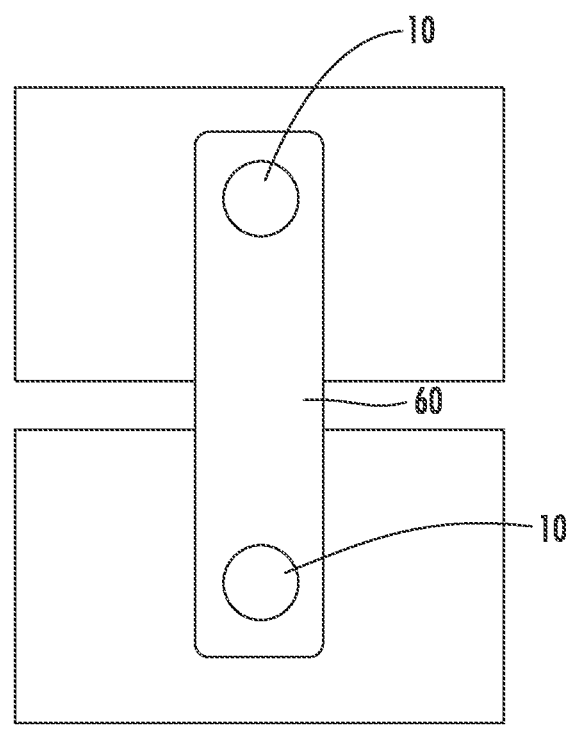
FIG. 23 is a schematic of two bones attached with a plate and secured with two anti-rotation screws shown in FIG. 7.

Because of the reverse threading of the threaded tip 12 and the outer sleeve 16, the screw 10 resists rotation when in a single structure, such as a single bone. Thus, as shown in FIG. 23, a plate 60 can be attached to bridge two bones with just two anti-rotation screws 10, one in each bone, eliminating rotational instability. Normally, two conventional screws are required in each bone to stop rotation of the plate relative to the bone. The anti-rotation screw 10 and the plate 60 may have structure for engaging each other, such as a corresponding non-cylindrical shape, to counter rotation of the plate and screw relative to each other.

Figure 9:
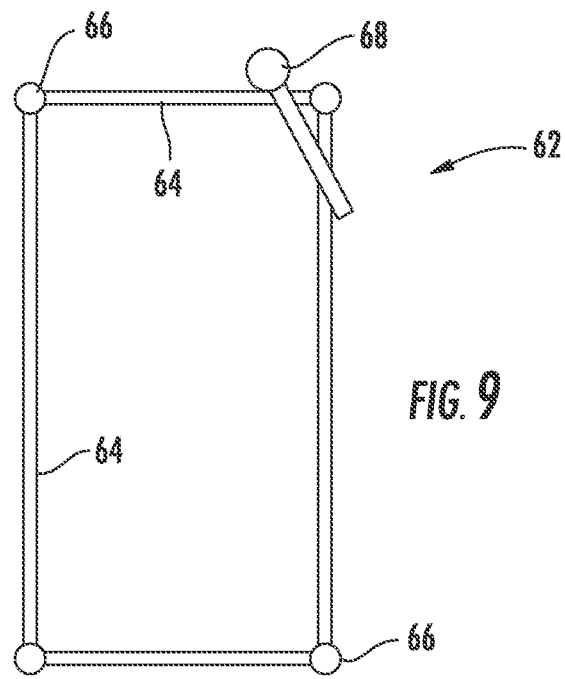
FIG. 9 is a plan view of the intervertebral cage of FIG. 8 expanded into a disc space and secured with a pin.

As shown in FIG. 9, the system may use or include an intervertebral cage 62 that includes a plurality of links 64 and hinges 66, such as four links connected by hinges to form a four-bar linkage. Each of the links has a height configured to hold endplates of two adjacent vertebrae 54, 56 apart from each other a desired distance. Two of the links may have a first length and another two of the links may have a second length, not equal to the first length, so as to form a rectangular shape or equilateral shape.

Figure 8:
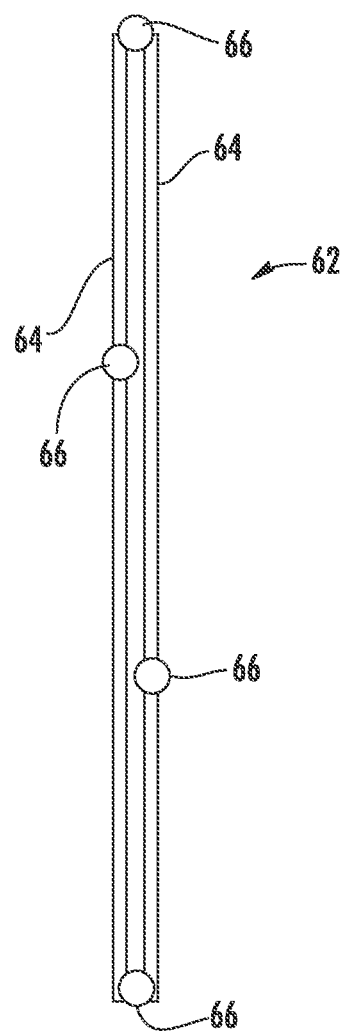
FIG. 8 is a plan view of a collapsed intervertebral cage configured for insertion through a small incision.

Advantageously, the relatively thin dimensions of the links 64 and the flexibility of the hinges 66, allow the cage to be folded relatively flat upon itself, as shown in FIG. 8. This configuration allows the cage 62 to be inserted through a small incision into the disc space or between two adjacent bones. When deployed, the first length (and the two corresponding opposing links 64) extends anterior-posteriorly within the disc space between the end plates of the vertebra 54, 56. The second length extends medio-laterally within the disc space thereby providing a relative large footprint.

As shown in FIG. 9, the cage 62 may include a pin 68 that is configured to engage an opening in two adjacent ones of the links 64, across one of the hinges 66, so as to lock the adjacent links into a predetermined angular position, such as 90 degrees. Defined in the pin 68 may be a detent that is engaged by one or both of the links 64 so that the pin 68 locks into position within the opening, wherein it can resist backing out from the opening. The pin 68 may also include a spring-biased rivet, ball or other engagement member configured to lock the relative sliding motion of the pin 68 once it has reached a predetermined position. The spring biased locking member may also be resident on one of the links and extend into the pin detent.

Figure 10:
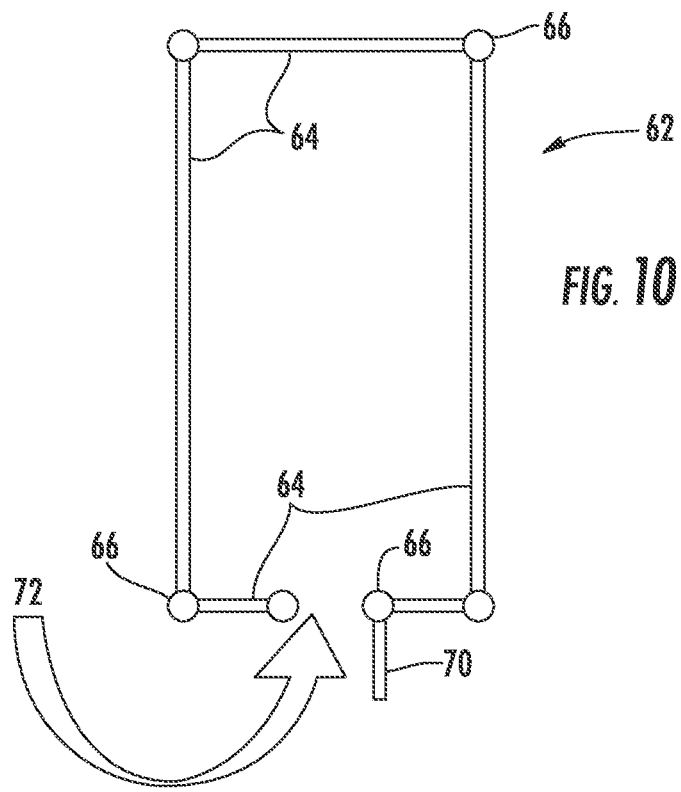
FIG. 10 is a plan view of an intervertebral cage with a door for accessing a central area of the cage.
Figure 11:
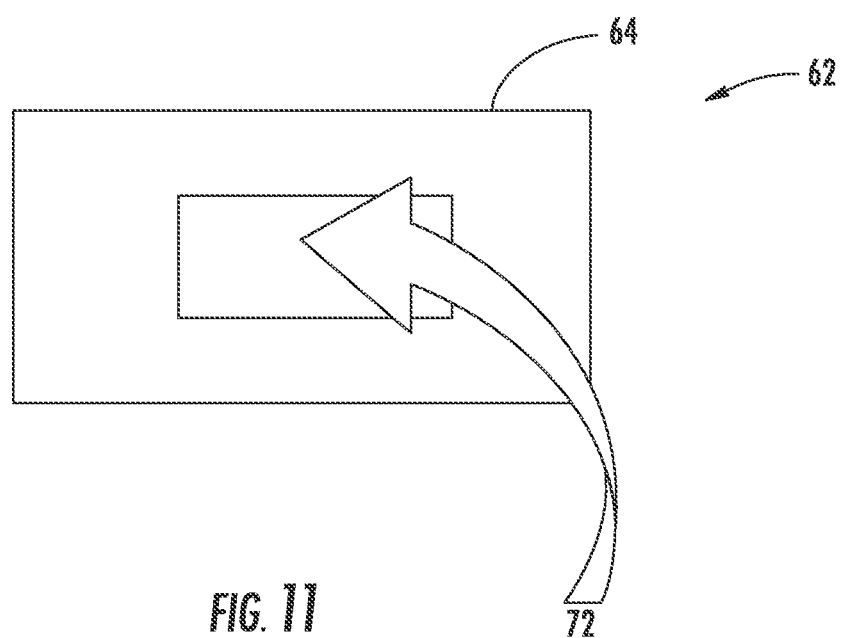
FIG. 11 is a side elevation view of an intervertebral cage having a window.

When deployed, the cage 62 has an open middle and may include a window 72 in one of the links 64 for providing access to the open middle, as shown in FIG. 11. Also, a door 72 may be included, wherein the door is configured to open on its own hinge and provide access to the open middle, as shown in FIG. 10. The door 70, or the window 72, may be used to access the open middle and place a "bone filling" such as a bone graft and/or growth promoting materials therein.

A method of using the cage 62 includes collapsing the links 64 into the linear arrangement, as shown in FIG. 8, and inserting the linear arrangement through a small incision into the disc space. Then, the two proximal links 64 of the cage 62 are pried apart (such as by using long instruments) to form a proximal angle, such as a 90 degree angle.

Simultaneously, in the case of a four bar linkage, the opposite distal links 64 open at the opposite hinge to form a distal angle because the distal links 64 are urged open with ends of the proximal links through the middle hinges. Also in the case of a four bar linkage, the distal angle is equal to the proximal angle.

Once the cage 62 is expanded in the disc space, the pin 68 is inserted through the surgical opening through the opening in the proximal two links 64 until its detent or spring-loaded mechanism locks into place, as shown in FIG. 9.

To facilitate fusion, the window 72 is accessed for insertion of a bone filling into the center opening of the cage 62, as shown in FIGS. 10 and 11. If the door 70 is present, it is opened, the bone filling is added, and the door is closed over the window 72.

Figure 24:
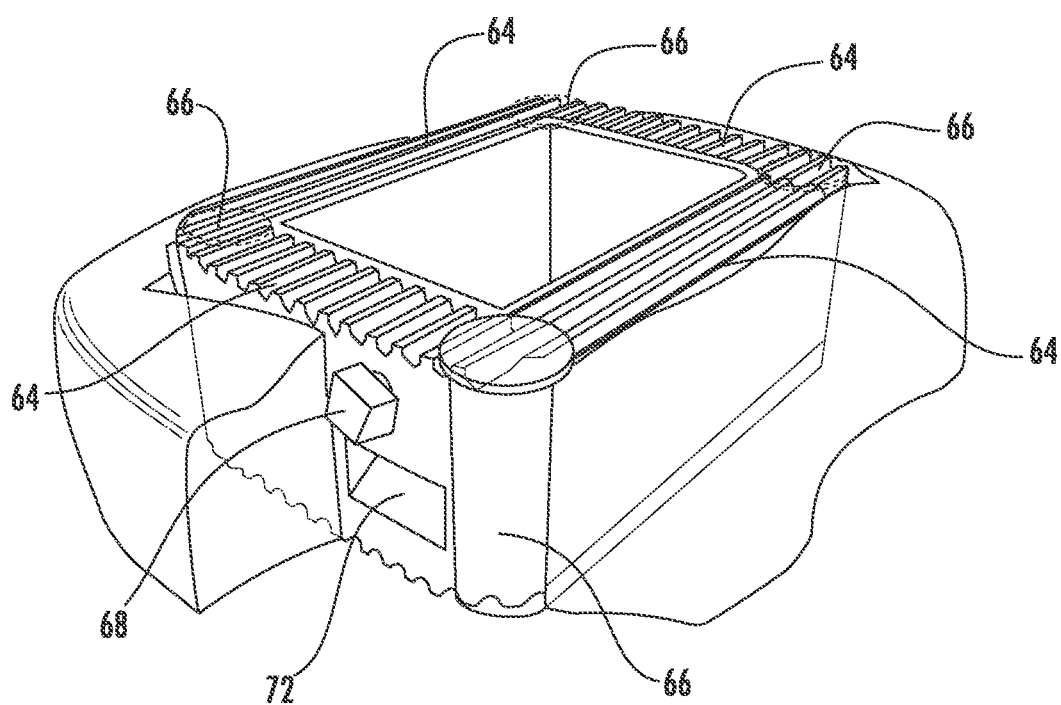
FIG. 24 shows a perspective view of an expanded cage with four links and four hinges and defining a window subjacent a pin.

The window 72 may also be positioned, as shown in FIG. 24, subjacent the opening for the pin 68. The pin may include threads and extend through an opening above the window allowing for a more compact access for both the pin and the bone filling procedure. Further, tops and bottoms of the links 64 may have defined on them serrations or ridges to improve fixation.

Further advantageously, placement of the cage 62 may be combined with attachment of bilateral bone screws 10 (either before or after cage 62 placement) as described above for improved stability and fusion potential even through minimal incisions and relatively little disc removal.

Figure 25:
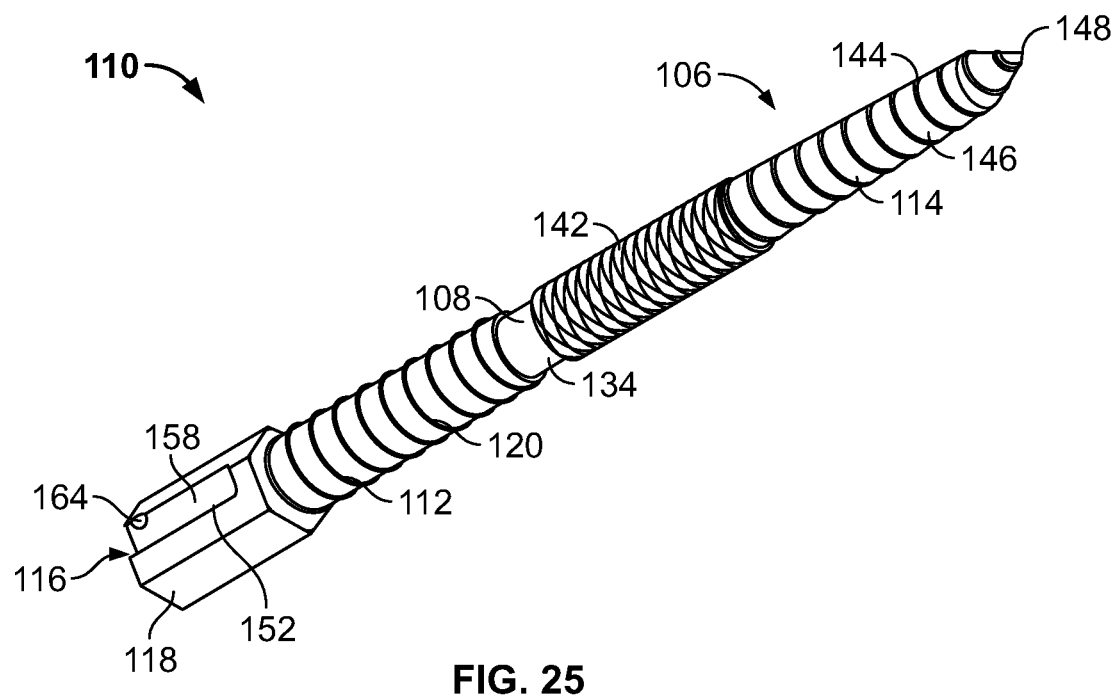
FIG. 25 shows a perspective view of a bone screw of another implementation.
Figure 26:
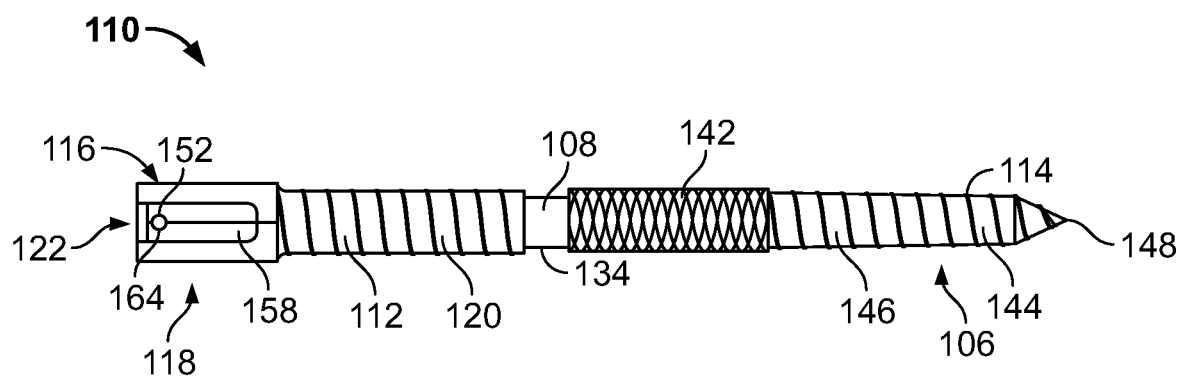
FIG. 26 shows an elevation view of the bone screw of FIG. 25.
Figure 27:
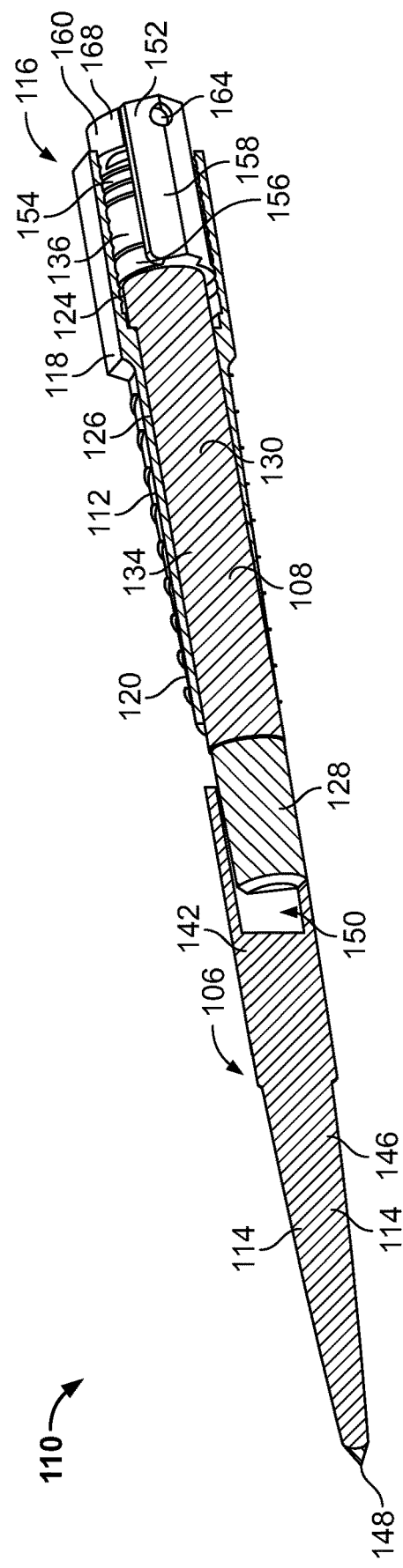
FIG. 27 shows a partial sectional view of the bone screw of FIG. 25.
Figure 31:
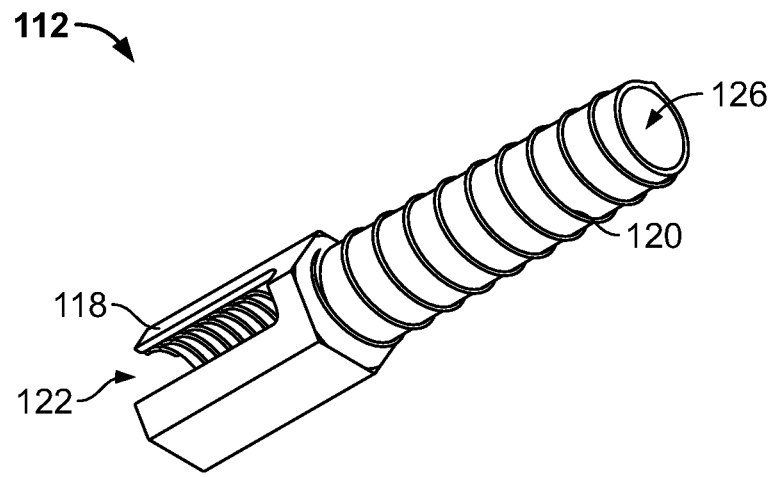
FIG. 31 shows a plan view of a proximal sleeve of the bone screw of FIG. 25.
Figure 32:
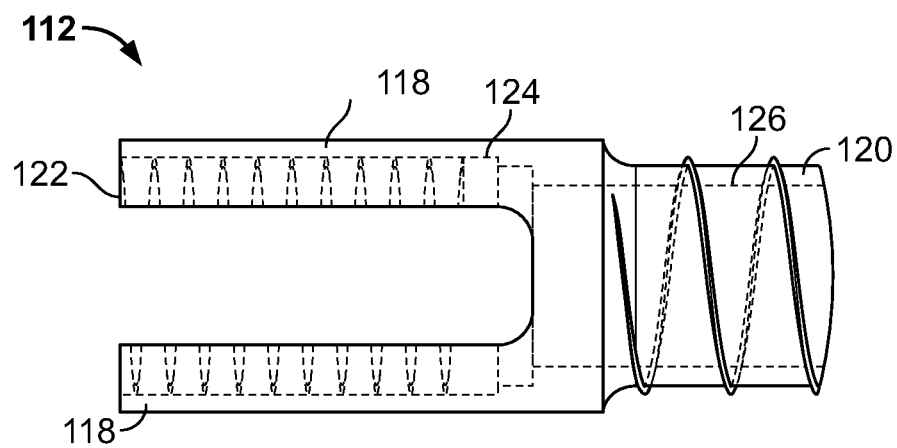
FIG. 32 shows an elevation view of the proximal sleeve of FIG. 31.

An additional implementation of a bone screw 110 is shown in FIG. 25. The bone screw 110 includes an inferior or proximal portion 112, a superior or distal portion 114 and a connector 116. The use of proximal and distal herein is relative to the healthcare worker or surgeon using the device. Inferior and superior are relative to the patient and assume the screw is being inserted through the vertebral bodies in a superior direction—towards the patient's head. Of course, these directions are for reference As shown in FIGS. 27, 31 and 32, the proximal portion 112 has a sleeve shape (generally) and includes a proximal end 118 and a distal end 120. The proximal end 118 includes a hexagonal outer diameter defining a transverse U-shaped slot 122 that extends through opposite walls of the hexagonal outer diameter. The hexagonal outer shape is configured to fit an 8 mm socket driver for advancement of the proximal portion 112. The hexagonal outer diameter may have a diameter of 7.75 mm to 7.95 mm for example for mating with an 8 mm driver.

The U-shaped slot has a width of about 3.95 to 4.20 mm. Defined within the proximal end 118 is a cylindrical bore 124 having a plurality of threads extending around the inside diameter. The threads within the cylindrical bore 124 may have a pitch of about 1 mm, a major diameter of 6.80 to 7.00 mm and a minor diameter of 6.30 to 6.50 mm. The cylindrical bore 124 has a step change in diameter where the threads end near the bottom of the bore and a second step change to a smaller 5.31 mm. (Tolerances for the measurements herein are +/−0.10 mm for a two place decimal and +/−0.05 for a three place decimal.)

The distal end 120 of the proximal portion 112 includes a gradually tapering cylindrical shaft. For example, the taper may be 0.5 degrees. The distal end 120 may have a length of 25 mm and a plurality of threads extending around its outside surface. The threads may, for example, have a pitch of 2.5 mm, a major diameter of 7.35 mm and a minor diameter of 6.75 mm. As shown in FIG. 27, the distal end 120 includes a cylindrical bore 126 that extends the length of the distal end 120 of the proximal portion 112.

Figure 35:
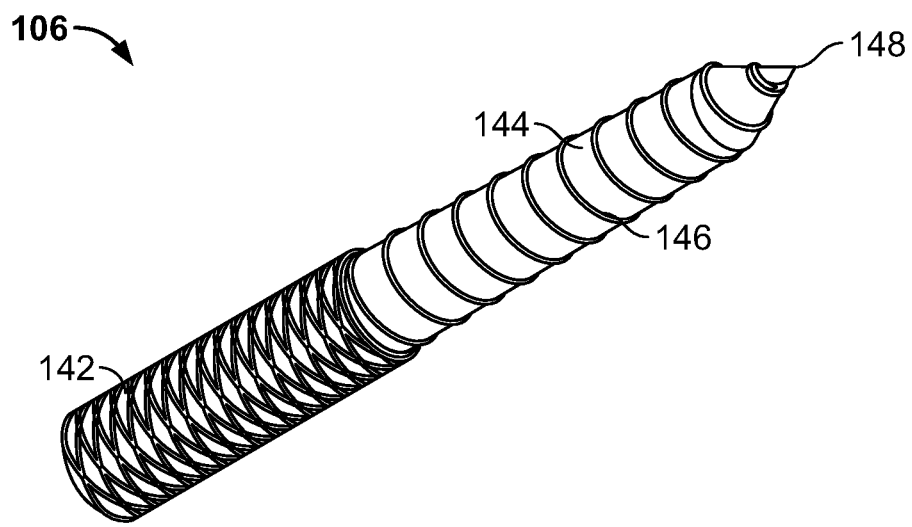
FIG. 35 is a perspective view of a distal screw portion of the bone screw of FIG. 25.
Figure 36:
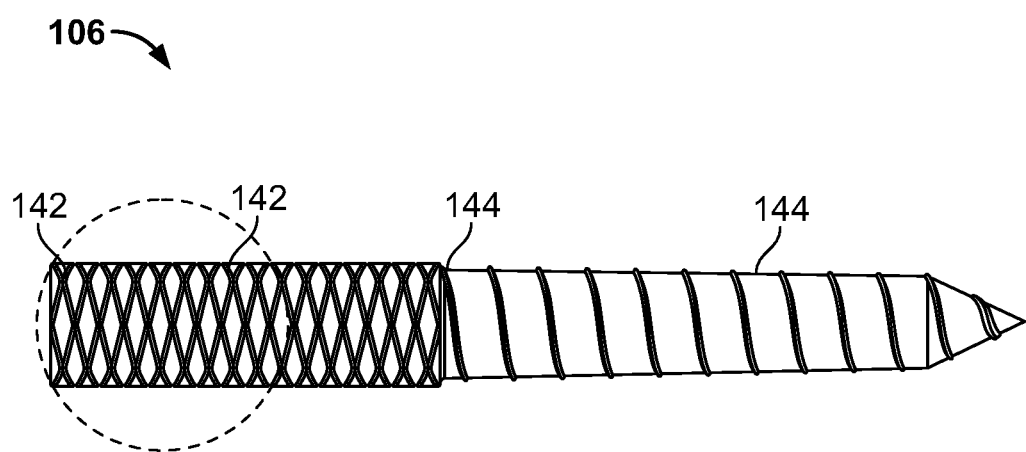
FIG. 36 is an elevation view of the distal screw portion of FIG. 35.
Figure 37:
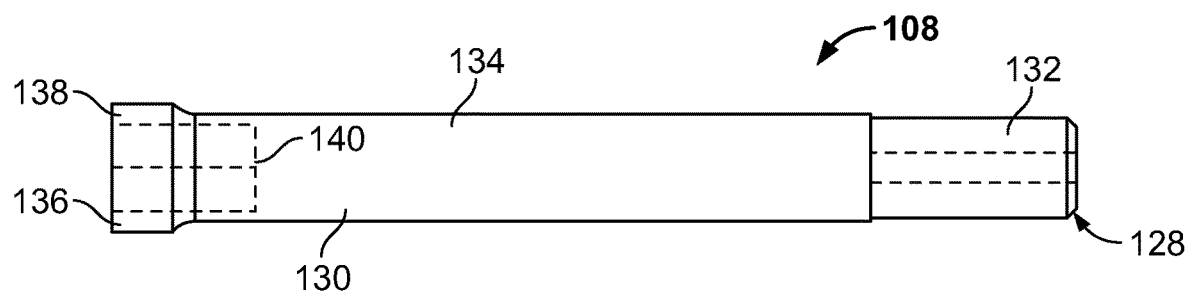
FIG. 37 is an elevation view of an inner post of the bone screw of FIG. 25.

As shown in FIGS. 27, 35 and 36, the superior or distal portion 114 includes a screw portion 106 and an inner or main shaft or post 108.

As shown in FIGS. 27 and 37-39, the inner post 108 of the distal portion 114 includes a distal end 128 and a proximal end 130. The distal end 128 of the inner post 108 includes a small diameter cylindrical section (e.g., 4.90 mm) with a chamfered free edge. For example, the chamfer may be 45 degrees. Defined within the distal end 128 of the inner post 108 is a 1.50 mm cylindrical bore. The distal end 128 of the inner post 108 may be 9.50 mm long and may include a bore 132.

Figure 29:
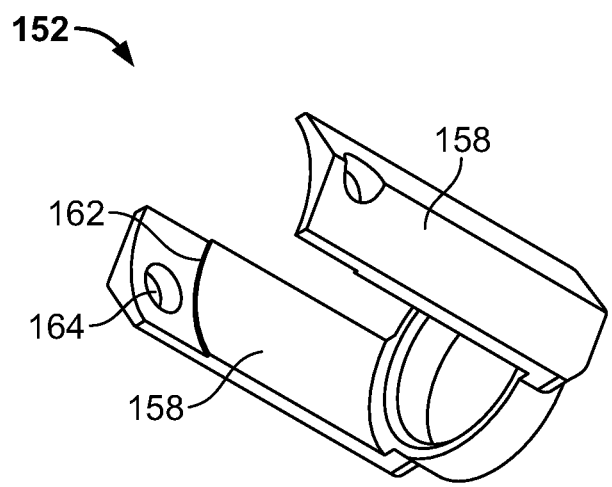
FIG. 29 shows a perspective view of a trap of the bone screw of FIG. 25.

The proximal end 130 of the inner post 108 has a shaft portion 134 that has a cylindrical shape and extends along the middle of the inner post 108. The proximal end 130 also includes a driving end 136 on its most proximal, free end, as shown in FIG. 29. The driving end 136 has a head 138 which flares out to a diameter of 6.19+/0.10 mm for example. The length of the head 138 may be 3 mm for example. The transition between the shaft portion 134 and the head 138 is defined by a convex taper, such as a taper with a 1.50 mm radius.

Figure 28:
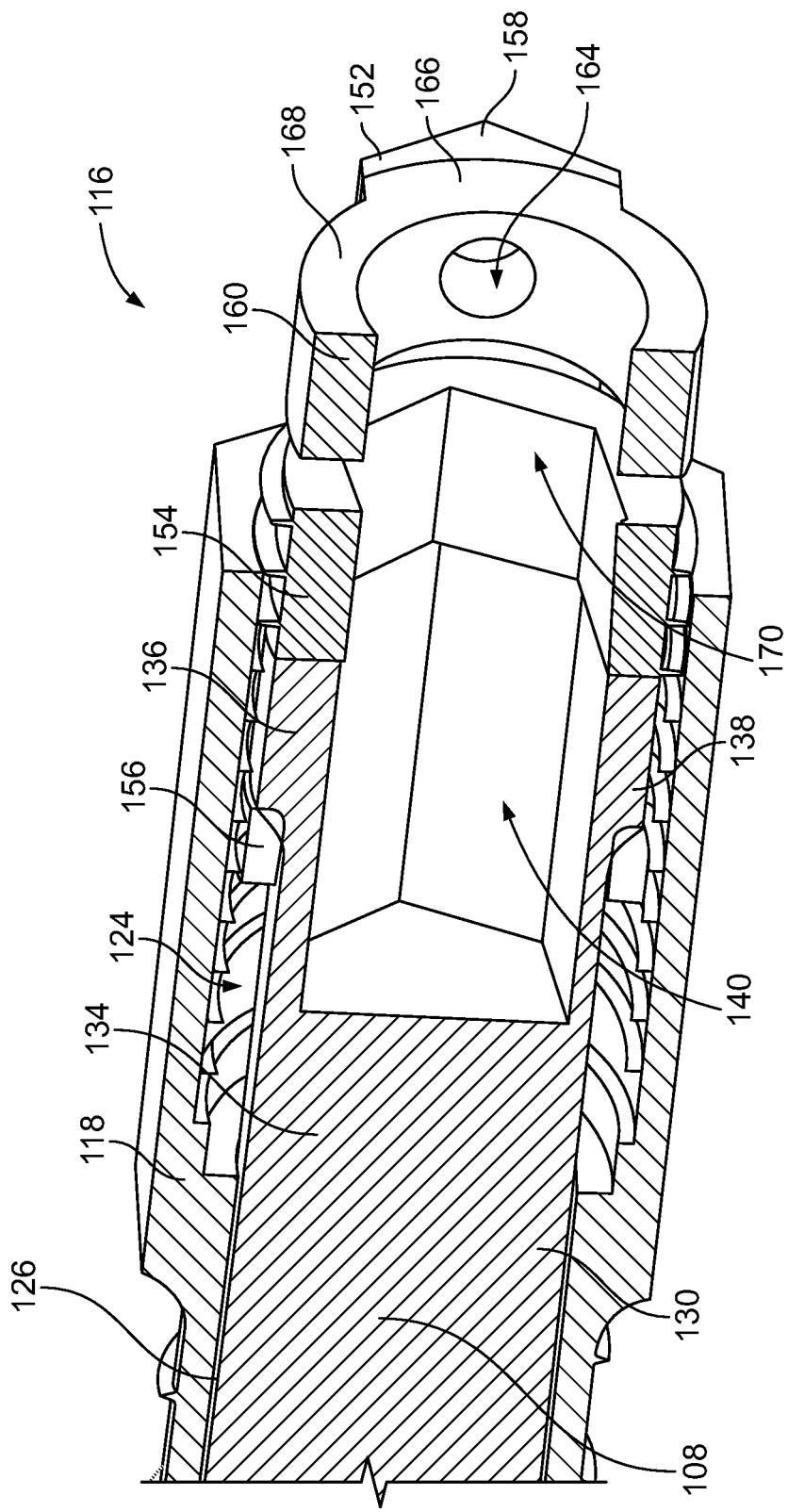
FIG. 28 shows an enlarged section view of a proximal end of the bone screw of FIG. 25.

The driving end 136 may also include a driver receptacle 140, such as the one shown in FIG. 28, with a hexagonal shape configured to receive a driver, such as an Allen wrench or screw driver with a hexagonal driving end. Notably, other non-cylindrical shapes could be defined by the driver receptacle 140 to transmit torque from a driver.

Figure 30:
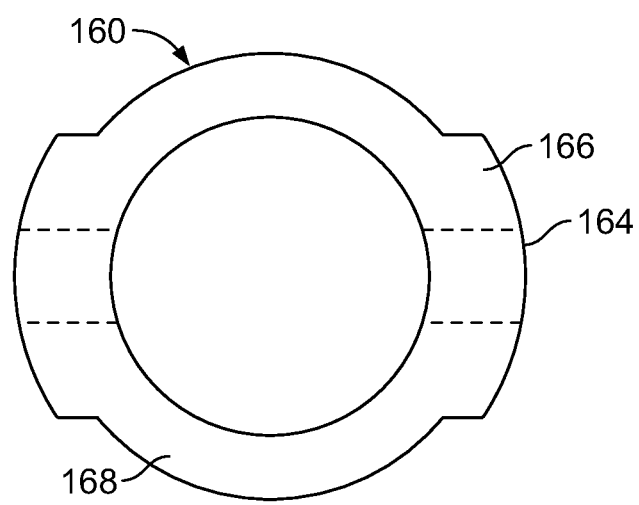
FIG. 30 shows a plan view of a cap of a connector of the bone screw of FIG. 25.

The screw portion 106 includes a proximal end 142 and a distal end 144. The proximal end is configured to facilitate bone ingrowth or other fixation of the bone screw 110 once implanted. For example, the proximal end 142, as shown in FIG. 30, may have a cylindrical shape with 20 mm length. The proximal end 142 may be a cage (as described above) for holding bone growth promoting compounds. Or, the proximal end 142 may have a knurled or textured outer surface that is configured to promote bone adhesion. The knurl for example may have a diamond shaped lattice that is configured to hold bone chips in the grooves of the knurl.

Defined within the proximal end 142 of the screw portion 106 may be a slightly tapering bore 150 having a proximal diameter of about 4.80 mm and tapering at 0.5 degrees along about a 10.00 to 10.40 mm length. This taper is configured for a press-fit reception of the inner post 108 which has a 4.90 mm diameter.

The distal end 144 of the screw portion has a conical shape that tapers gently at mid-shaft 146 and tapers aggressively near a point 148. For example, the mid-shaft 146 may taper at 1 degree along about 12.5 mm and then at 25 degrees to the distal-most point. Threads extend along the distal end 144, starting at its base and may have a pitch, for example, of 2.50 mm, a major diameter of 6.10 mm and a minor diameter of 5.40 mm.

As shown in FIGS. 27-30, 33, 34 and 38-39, the connector 116 includes a trap 152 and a locking nut or stabilizer 154. Generally, the trap 152 is configured to couple to the remainder of the bone screw 110 and to contain the stabilizer 154. The trap, as shown in FIG. 29, includes a base 156, a pair of arms 158 and a cap 160. The base 156, for example, may have a circular ring shape defining a central bore or opening. The ring shape, for example, may have a radius of about 3.20 mm and the bore a diameter of 5.31 mm. The thickness or height of the base 158 may be about 1.50 mm. The bore may also include a 45 degree chamfer.

The arms 158 extend upwards (proximally) from the base 156 and are attached on opposite sides of the base 156. The arms 158 have two angled flats defining their outer surfaces and partial cylindrical arcs defining their inner surfaces, the cylindrical arcs tracing a radius of 3.50 mm of a circle. At their proximal-most free edge is defined a lip 162 which is a step down to a slightly bigger radius (3.60 mm) partial cylindrical surface. The arms have a length of about 11 mm, or 9.50 mm more than the height of the base 156. The arms also have a width of about 3.85 mm or 3.95 mm.

Defined near the proximal or top ends of the arms 158 are a pair of aligned, concentric pin holes 164. The pin holes 164 have a radius of about 0.75 mm. The pin holes 164 are centered at the apex between the two outer angled flat surfaces of the arms 158.

As shown in FIGS. 28 and 30, the cap 160 may include a cylindrical ring 168 with a pair of enlarged ears 166. The radius of the ring 168 of the cap 160 may, for example, be about 3.15 mm. The ears 166 are portions of an outer, larger cylinder and extend from opposite sides of the ring 168. Defined through the ears 166 are a pair of pin holes 164 that are axially aligned with each other on opposite sides of the axis of the cap 160. The radius of the ears 166 is configured to match the radius of the inner opening of the arms 158 proximal the lip 162. For example, the ears may have a 3.60 mm radius. The matched radius allows the cap to be seated on the lip 162

Figure 33:
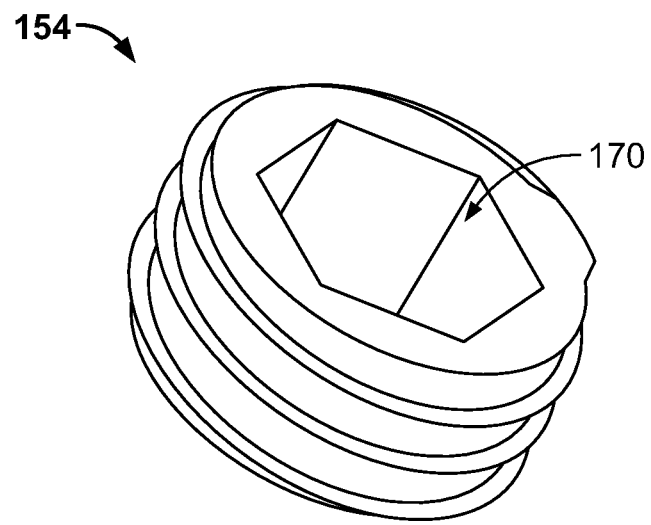
FIG. 33 shows a perspective view of a stabilizer of a connector of a bone screw of FIG. 25.
Figure 34:
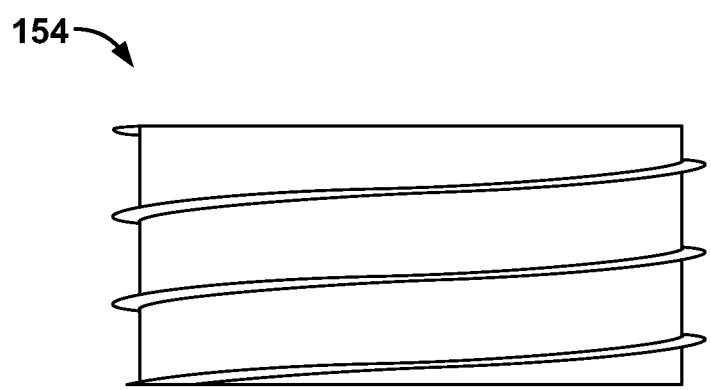
FIG. 34 is a plan view of the stabilizer of FIG. 33.

As shown in FIGS. 33-34, the stabilizer 154 has a cylindrical shape with a plurality of threads extending around its out surface. The threads, for example, have a pitch of 1 mm, a major diameter of 6.60 mm to 6.79 mm and a minor diameter of 6.10 mm to 6.29 mm. The length or height of the cylinder is about 3 mm. Defined in the center of the stabilizer is a driver receptacle 170, such as a 5/32 hexagonal receptacle for an Allen wrench. Driving of the stabilizer, as will be described in more detail below, drives compression and distraction of the proximal portion 112 and distal portion 114 of the bone screw 110.

Figure 38:
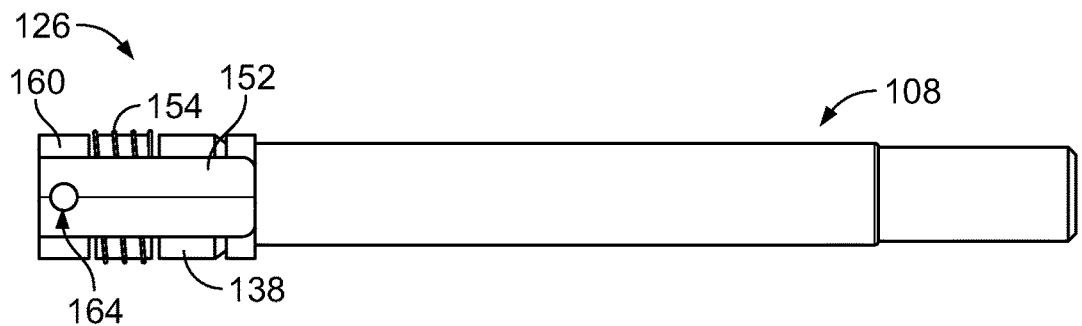
FIG. 38 is an elevation view of an assembled connector and inner post of the bone screw of FIG. 25.
Figure 39:
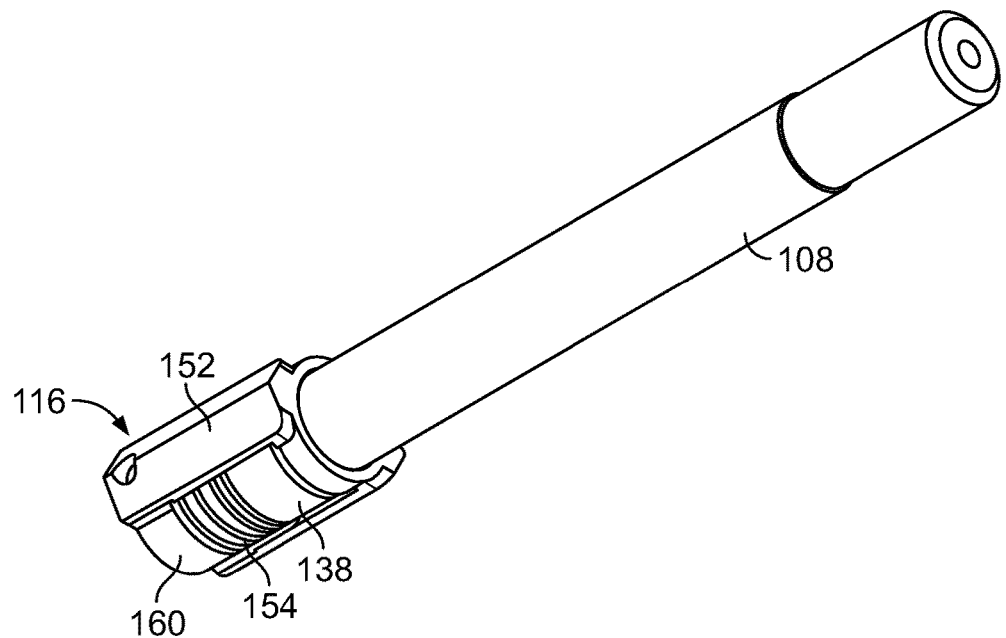
FIG. 39 is a perspective view of the assembly of FIG. 38.

As shown in FIGS. 38-39, the trap 152 and stabilizer 154 may be first assembled to the head 138 of the inner post 108. For example, the distal end 128 of the inner post 108 may be slipped through the opening in the base 156 of the trap until the head 138 is positioned between the arms 158. (The head 138 is too large to pass through the base 156 ring.) The stabilizer 154 may then be advanced, such as by an Allen wrench, along the threads within the arms 158 until it abuts the head 138. Then, the cap 160 may be slipped in between the upright arms 158 of the trap 152 until the ears 166 hit the lip 162. The pin holes 164 of the cap 160 and arms 158 are aligned. Optionally, a pin may be advanced through the pin holes 164. The pin allows for deformation in the inner post during the pressure fitting. This connection between the inner post and the superior screw may also be connected together by a rivet or other fasteners.

As shown in FIG. 27, the inner post 108 and connector 116 may then be assembled by insertion through the proximal portion 110 of the bone screw 110. In particular, the distal end 128 of the inner post 108 may be inserted through the cylindrical bores 124, 126 of the proximal portion 112 of the bone screw 110. As the inner post 108 is advanced, the arms 158 of the trap 152 are aligned with and inserted into the U-shaped slots 122 of the proximal end 118. Further advancement may include rotating or driving the stabilizer 154 so that its threads advance along the inner threads on the inside of the proximal end 118.

The distal end 128 of the inner post 108 is then press fit into the bore 150 of the proximal end 142 of the screw portion 106. Rather than a press fit, other attachments could be employed such as threaded fittings, clamps, adhesives, etc. Once this assembly is finished, the bone screw 110 is ready for use in attaching, contracting or distracting vertebrae as described, for example, in the procedures disclosed for the bone screw 10 above.

The entire bone screw 110 may be driven by way of the hexagonal shape of the proximal end 118 of the proximal portion 112 of the bone screw.

After driving into two bone pieces, such as two adjacent vertebra or bone fragments, the relative positioning of the proximal portion 112 and distal portion 114 of the bone screw 110 (and hence of the adjacent bone fragments) may be controlled by insertion of a driver through the opening in the cap 160, the driver receptacle 170 of the stabilizer 154 and into the driver receptacle 140 of the inner post 108. Rotating the driver causes the threads on the stabilizer 154 to advance (or retract if counter-rotating) along the threads of the proximal portion 112. This causes the proximal portion 112 to slide along the inner post 108 of the distal portion 114.

Counter rotation of the stabilizer 154 distracts the proximal and distal portions because the stabilizer backs into the cap 160 of the trap 152. This pulls on the arms 158 and base 156 of the trap which is nested around the head 138 of the inner post 108. As the connector assembly moves out of the proximal portion 112, the screw portion 106 on the opposite end of the inner post 108 is pulled closer to the proximal portion.

Figure 40A:
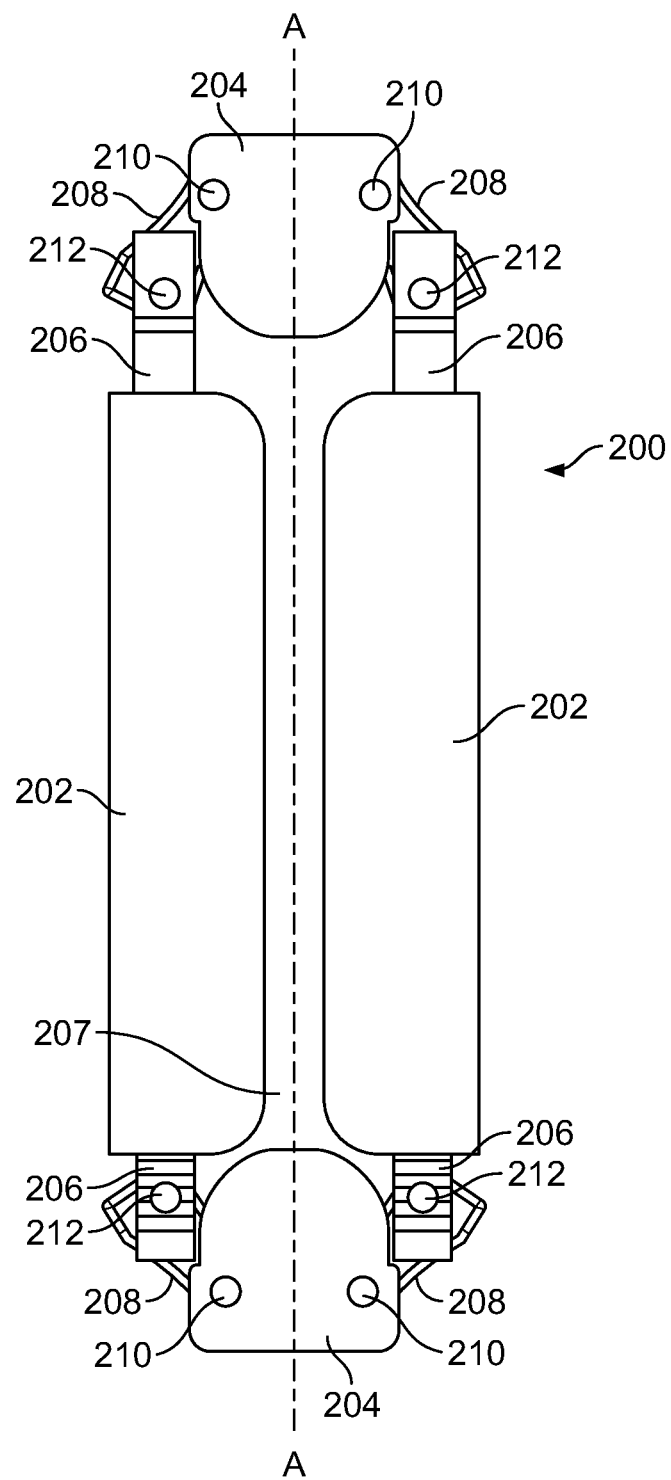
FIG. 40A is a plan view of a laterally and vertically expandable cage.
Figure 40B:
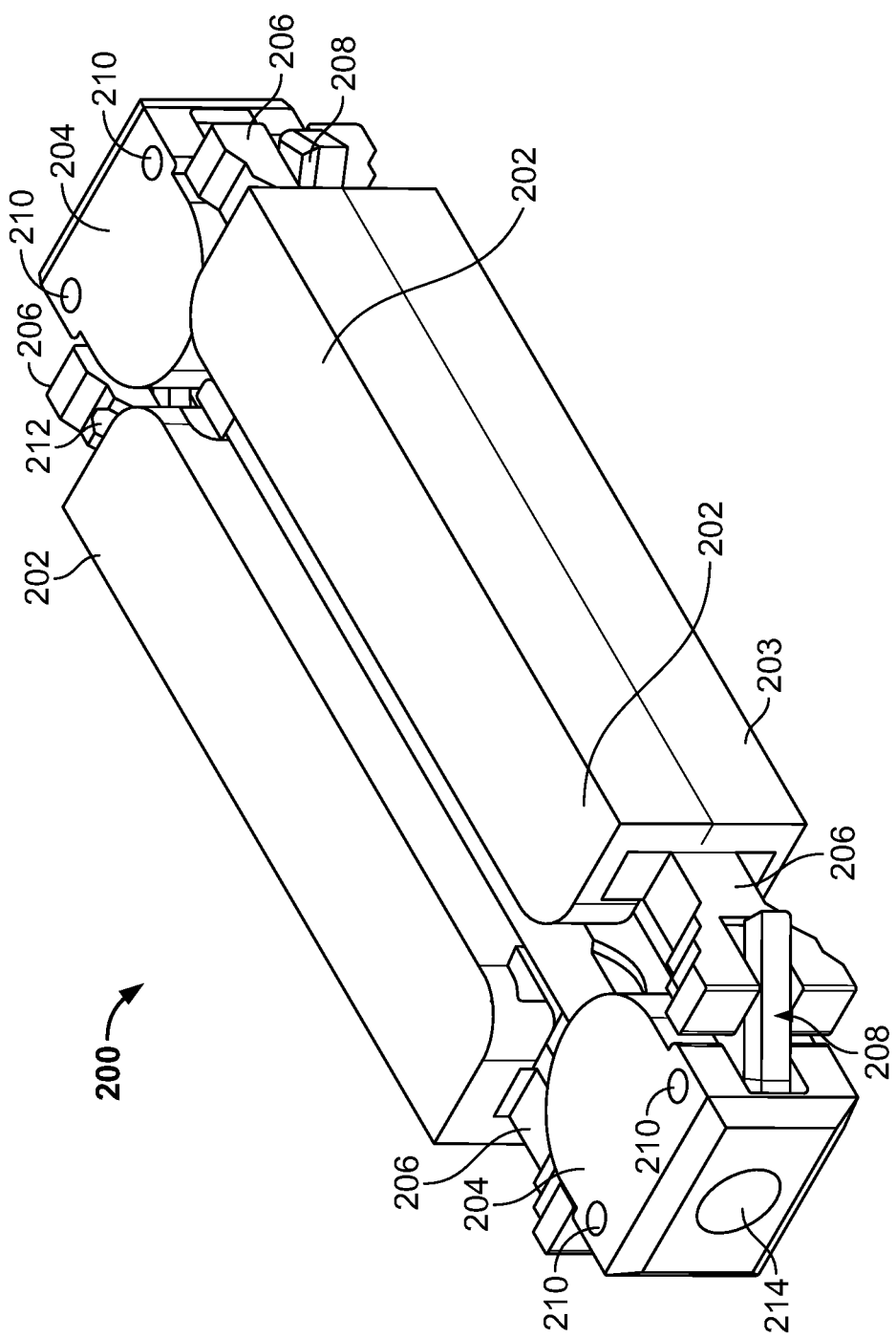
FIG. 40B is a perspective view of the expandable cage of FIG. 40A.

FIGS. 40A and 40B illustrate an example expandable intervertebral cage in an unexpanded state. FIG. 40A is top view illustration of the example expandable intervertebral cage 200. The cage is designed for implantation between two vertebrae of a patient at any location along the spine. For example, the cage can be implanted between two adjacent cervical, thoracic, lumbar, or sacral vertebrae. The cage is optionally used to fuse two adjacent vertebrae. The cage is optionally used to adjust the spacing between two adjacent vertebrae. The cage is optionally used with additional pharmacological, biological or mechanical agents administered at the site or in proximity to the site of implantation.

Figure 41A:
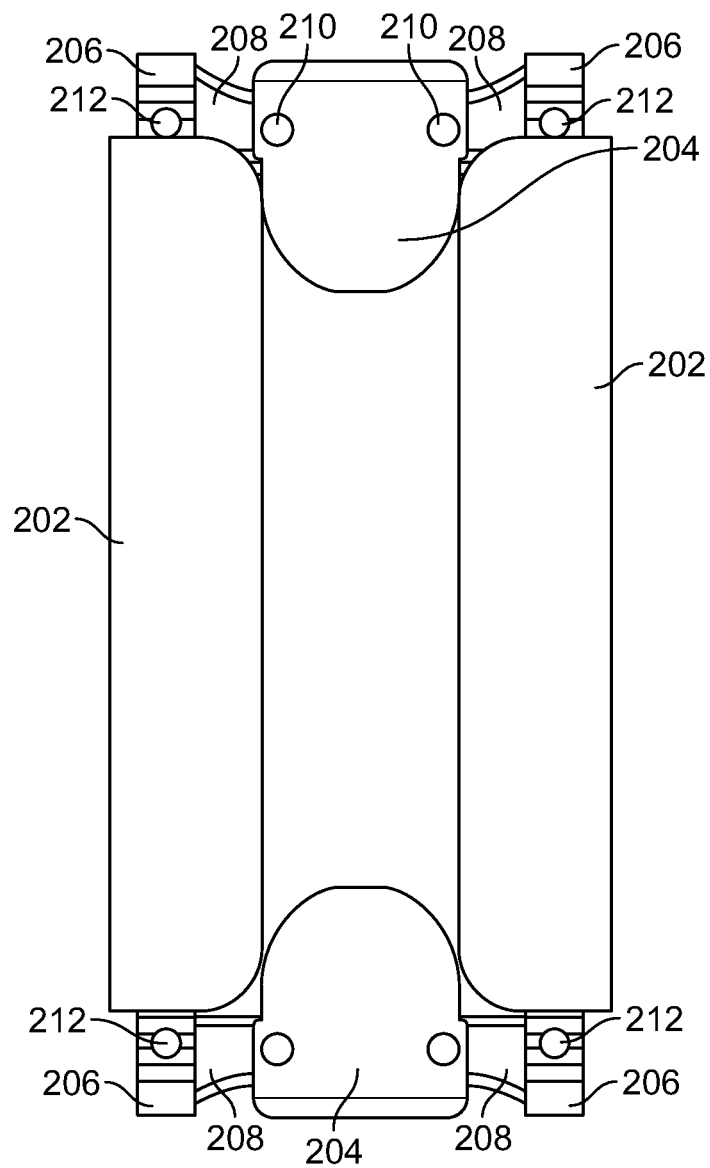
FIG. 41A is a plan view the expandable cage of FIG. 40A in a laterally expanded configuration.
Figure 41B:
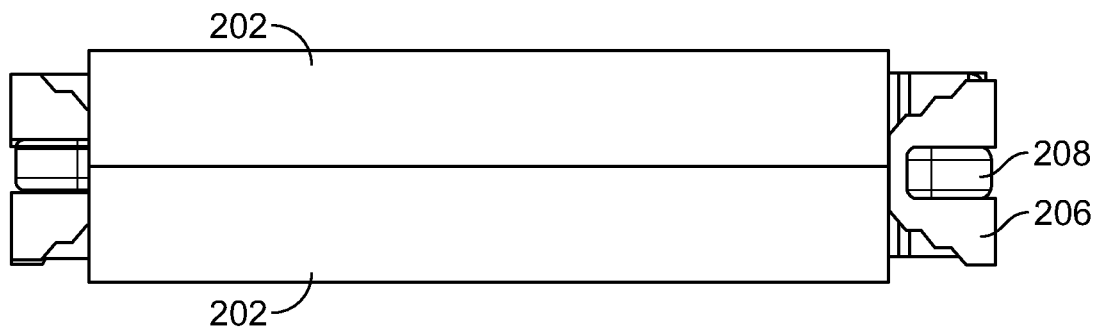
FIG. 41B is a perspective view of the expandable cage of FIG. 41A.

The cage 200 is optionally expandable both horizontally and vertically as will be described below. Optionally the cage is inserted between two adjacent vertebrae of the patient in a non-expanded state. An example of a horizontally expanded, but vertically non-expanded, state is shown in FIGS. 41A and 41B.

Once positioned as desired by a medical professional, the cage 200 can be expanded in a horizontal direction; for example, in the horizontal plane of the intervertebral space in which the cage is located. The cage 200 can also be optionally expanded in a vertical direction, which can increase the vertical separation between the adjacent vertebrae. Optionally, the horizontal expansion is performed before the vertical expansion. Optionally a single actuator is used to first cause horizontal expansion followed by vertical expansion. In this way, a low height and width profile of the unexpanded cage can be used for implantation and then with use of the single actuator, the height and width profile can be expanded as desired.

The cage 200 includes two pairs of longitudinal bars. Each pair includes an upper bar 202 and a lower bar 203 (as shown, for example, in FIG. 41B). The pairs are spaced from one another across the vertical midline plane A-A of the cage. The spacing across the vertical midline plane creates a space 207 that can be widened when the cage is expanded in the horizontal direction.

To cause movement of each bar pair away from the vertical midline plane, the cage includes at least one spacer 204. The one or more spacer 204 is moveable into and between the space 207 between the bar pairs. The size of the spacer 204 prior to horizontal expansion is larger than width of the space 207. To cause expansion, one or both of the spacers 204 are moved into the space 207, which urges the bars horizontally away from the midline plane A-A. Optionally, a surface of a spacer 204 is curved and corresponding surfaces of the bars are also curved. When the curved surfaces contact each other it facilitates entry of the spacer 204 into the space 207 and horizontal separation of the bar pairs.

As mentioned above, the cage 200 can also be expanded vertically. For example, the cage 200 optionally includes one or more separators 206. In the example cage 200 shown in FIGS. 40A-44, there are four separators.

Each separator 206 is positioned such that it can be moved between the bars (202 and 203) of the cage. In this regard, a first separator is positioned at a first end of one of the bar pairs for movement between that pair of bars, a second separator is positioned at a first end of the opposite bar pair for movement between that pair of bars, a third separator is positioned at a second end of one of the bar pairs for movement between that pair of bars, and a fourth separator is positioned at a second end of the opposite bar pair for movement between that pair of bars.

Each separator can be advanced between the individual bars at their given location. The separators have a height profile that is larger than any spacing between the upper 202 and lower bars 203 when the cage has not been vertically expanded. When one or more separator is advanced between the upper and lower bars, therefore, the bars are urged to separate, resulting in vertical expansion of the at least that bar pair.

Each separator 206 optionally has the same vertical or height profile so that when all four separators are advanced between the bars, the bar pairs symmetrically expand vertically. Optionally, however, one or more separator can have a different vertical or height profile from one or more of the other separators. The differing vertical or height profiles optionally result in an asymmetric vertical expansion of the cage when the separators are advanced between the bars. For example, a separator with a larger vertical dimension results in greater vertical displacement between the bars at the location where it is advanced between the bars, while a separator with a smaller vertical dimension results in a smaller vertical displacement between the bars at the location where it is advanced between the bars. Therefore, by selecting different sizes of separators in combination different asymmetric vertical expansion profiles are achieved.

Similarly, the width profile of the spacers 204 may also differ. In this way, asymmetric horizontal expansion is optionally accomplished.

Each spacer 204 is optionally connected via two connectors 208 that are on the same end of the bars. A spacer 204 is connected via two pivot pins 210 to the connector, for example, allowing the spacer to pivot relative to each connector. The connectors are also pivotably connected to the separators 206 located on the same end of the bars.

A threaded rod 220 (shown, for example, in FIGS. 41A, 43 and 44) optionally connects with the two spacers 204. By actuating the threaded rod 220, for example by rotating it at point 222, the two spacers are moved towards each other between the bar pairs resulting in separation of the bar pairs away from the vertical midline plane. The spacers 204, for example, may be drawn to each other by having different direction threads within their respective openings.

As the spacers advance towards each other, the connectors pivot relative to the spacers 204 and to the separators 206. As shown in FIG. 40A, the midline of each connector is acutely angled relative to the vertical midline plane of the cage. As shown in FIG. 41A, as the spacers are advanced closer to one another and the bar pairs separate horizontally, eventually the connectors rotate to a more closely perpendicular orientation relative to the vertical midline axis.

During this movement of the spacers, from the position shown in FIG. 40A to the position shown in FIG. 41A, the separators remain substantially in the same position, due to the free pivoting of the connectors about the pivot points (210 and 212). Because there has been movement of the spacers towards each other but the separators have stayed substantially stationary, the cage undergoes horizontal expansion without substantial vertical expansion. A side view of the orientation of FIG. 41A, where horizontal expansion has occurred but vertical expansion has not occurred is shown in FIG. 41B.

Figure 42A:
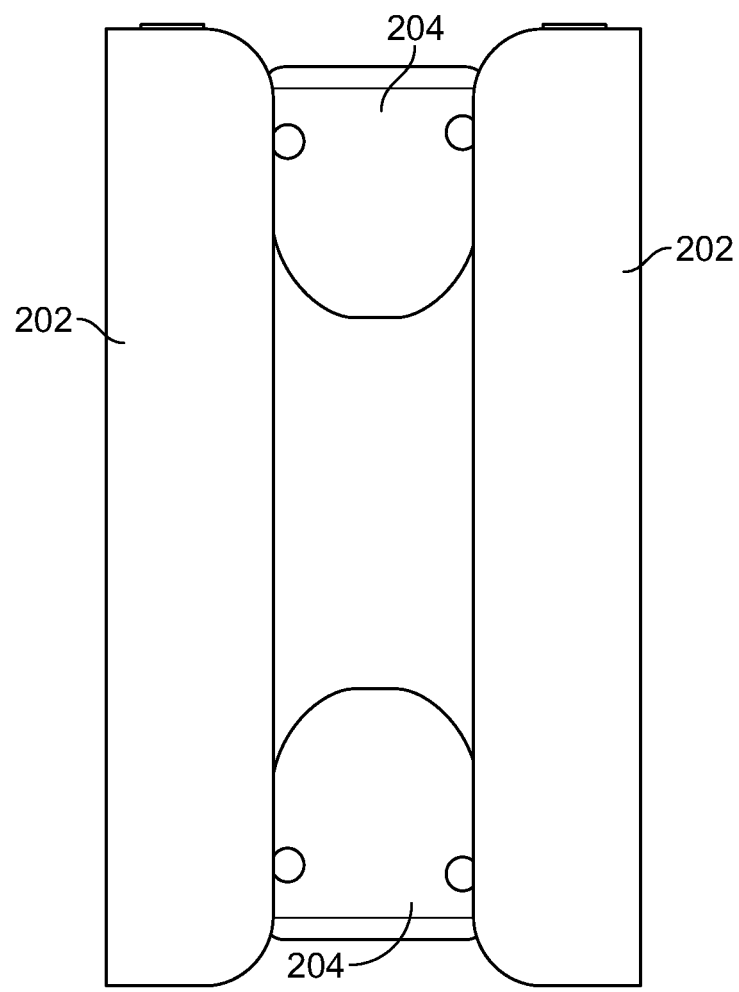
FIG. 42A is a plan view of the expandable cage of FIG. 41A further vertically expanded.
Figure 42B:
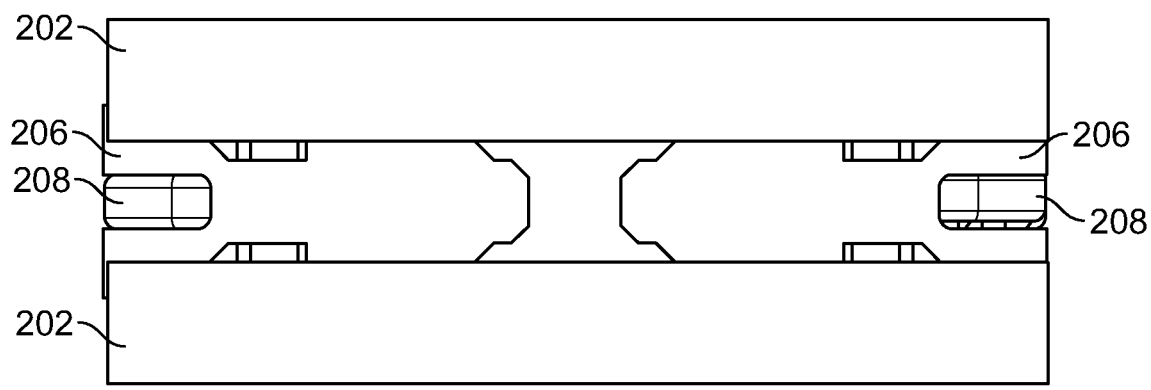
FIG. 42B is a side elevation view of the expandable cage of FIG. 42A.

As the spacers 204 are further advanced towards each other, the connector continues to pivot relative to the spacer and the separators and horizontal expansion progresses without substantial vertical expansion. Eventually the connectors cannot rotate any further as they contact one or more stop surfaces of the cage. For example, the stop surface is optionally a portion of the spacer and/or a surface of a bar that limits the ultimate extent of rotation. Once rotation has been stopped, continued actuation of the threaded rod 220 results in advancement of the separators 206 between the rods rather than further advancement of the spacers 204 towards each other. The result is that as the threaded rod is further actuated, the cage stops its horizontal expansion and begins a substantial vertical expansion as the separators 206 move between the rods to urge them apart vertically. In this way, the cage 200 is optionally expandable both horizontally and vertically. The horizontal expansion can occur prior to any substantial vertical expansion of the cage. FIG. 42B shows a side view after horizontal and vertical expansion.

Figure 43:
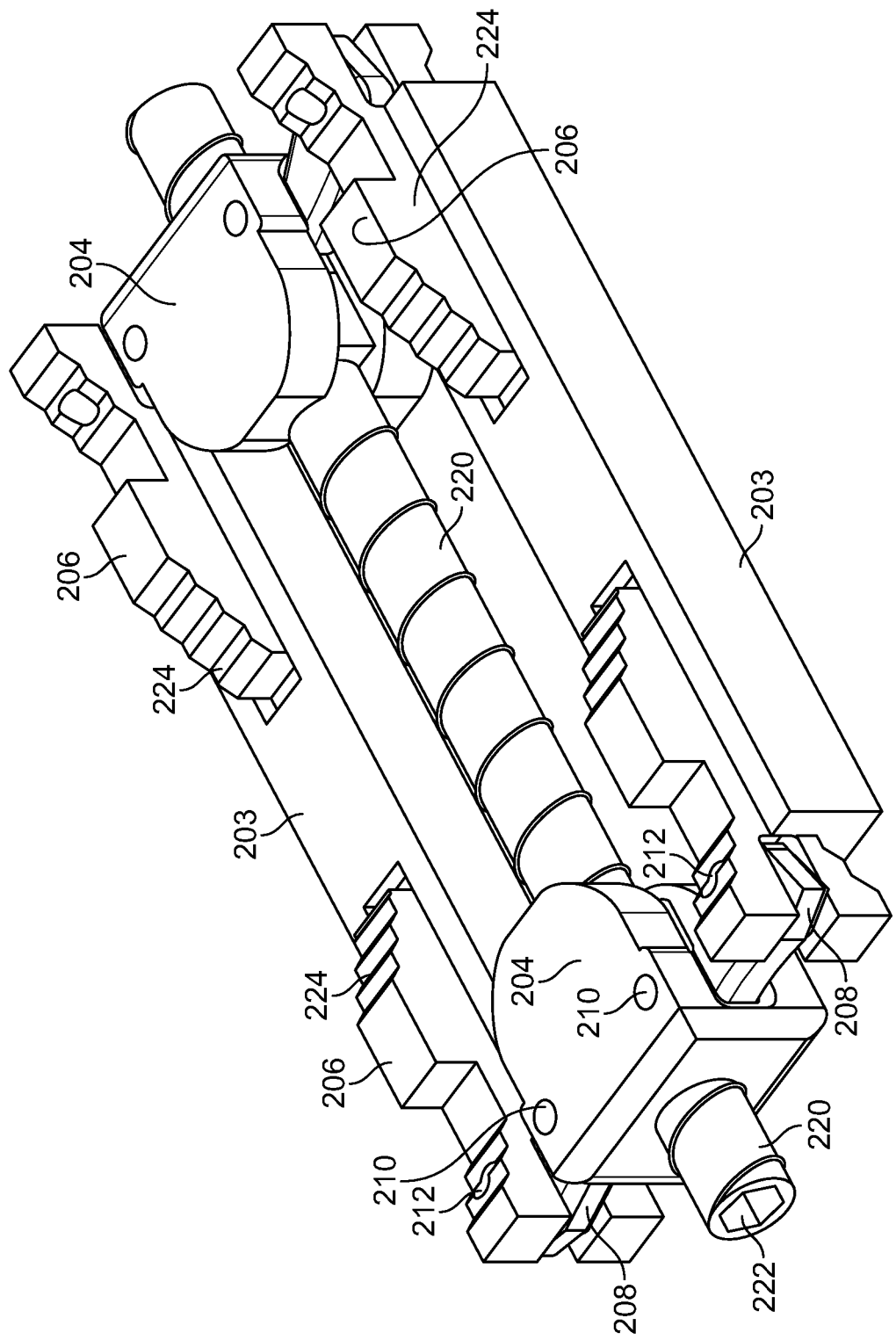
FIG. 43 is a partially disassembled view of the expandable cage of FIG. 42A.

As shown in FIG. 43, the separators 206 optionally have a sloped front surface with a lower vertical rise towards the front of each spacer and a higher vertical rise towards the back of each spacer. Optionally, as also shown in FIG. 43, the slope is stepped with each step being sequentially higher.

In this regard, as a separator is advanced between the bars, vertical separation between the bars at that location of the separator increases until the portion of the separator having its maximal height dimension is positioned between the bars, or until a desired vertical separation between the bars is achieved. In addition, when the slope is stepped, the vertical separation between the bars at a location of the separator can be adjusted to progressively greater amounts by progressively advancing new steps between the bars.

Figure 44:
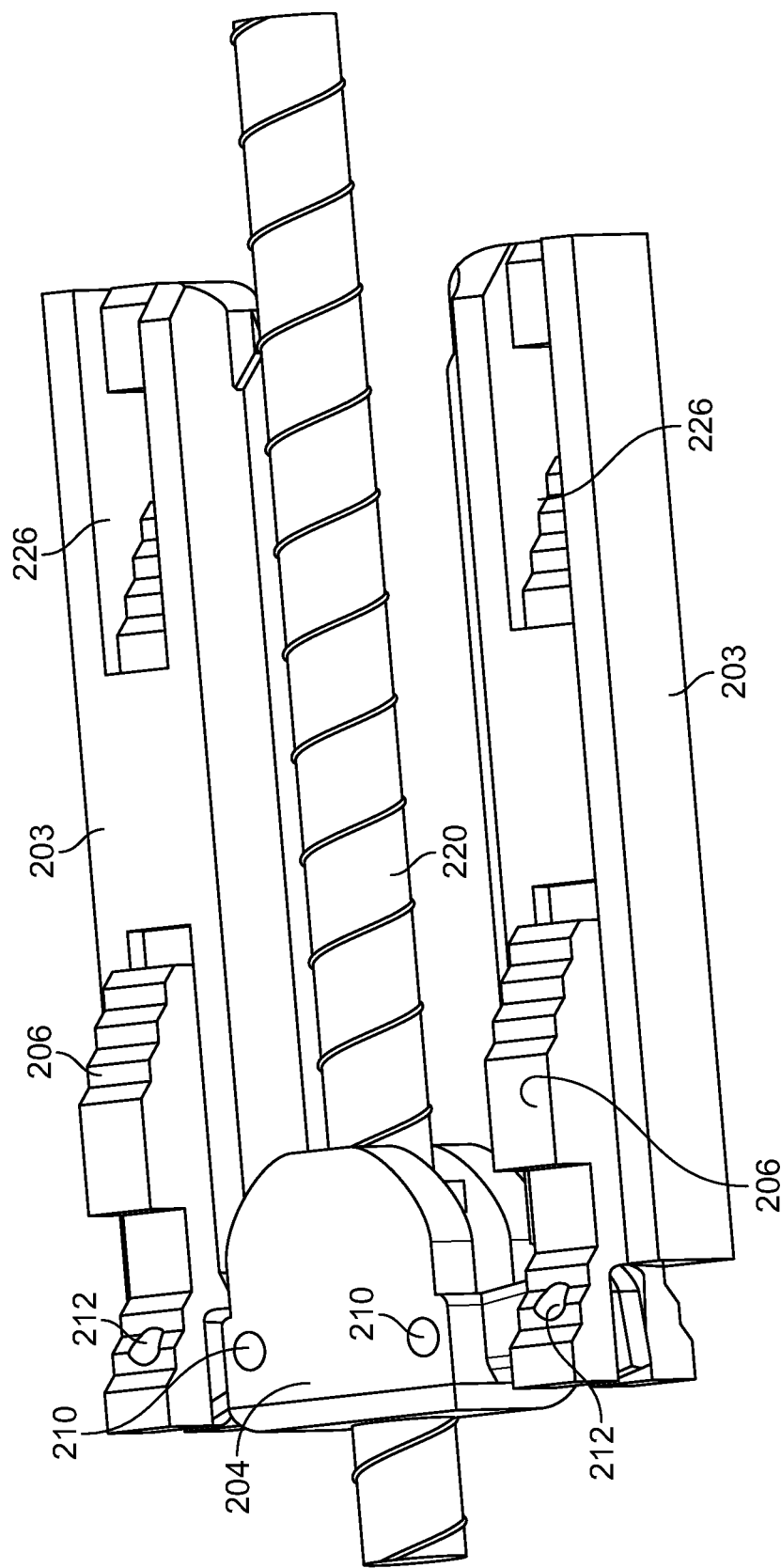
FIG. 44 is a further disassembled view of the expandable cage of FIG. 43.

Each bar, for example, as shown in FIGS. 43 and 44, optionally includes grooves 226 to accept the advancing separators 206. The grooves optionally include a complementary shape to the separator that is being advanced there into the groove.

Figure 45:
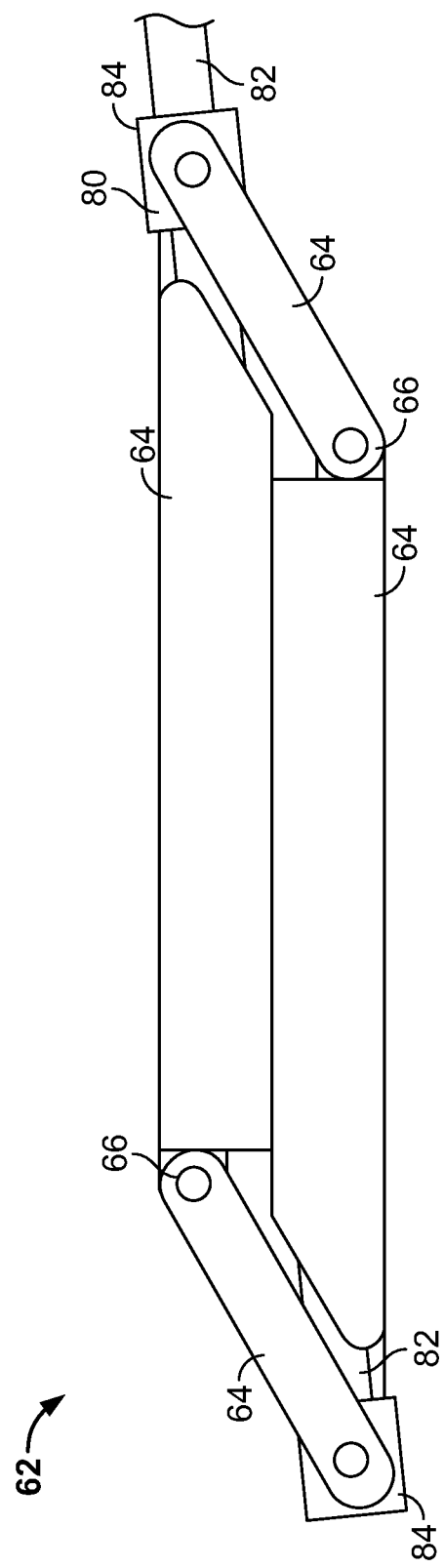
FIG. 45 is a plan view of a collapsed, four-bar intervertebral cage.
Figure 46:
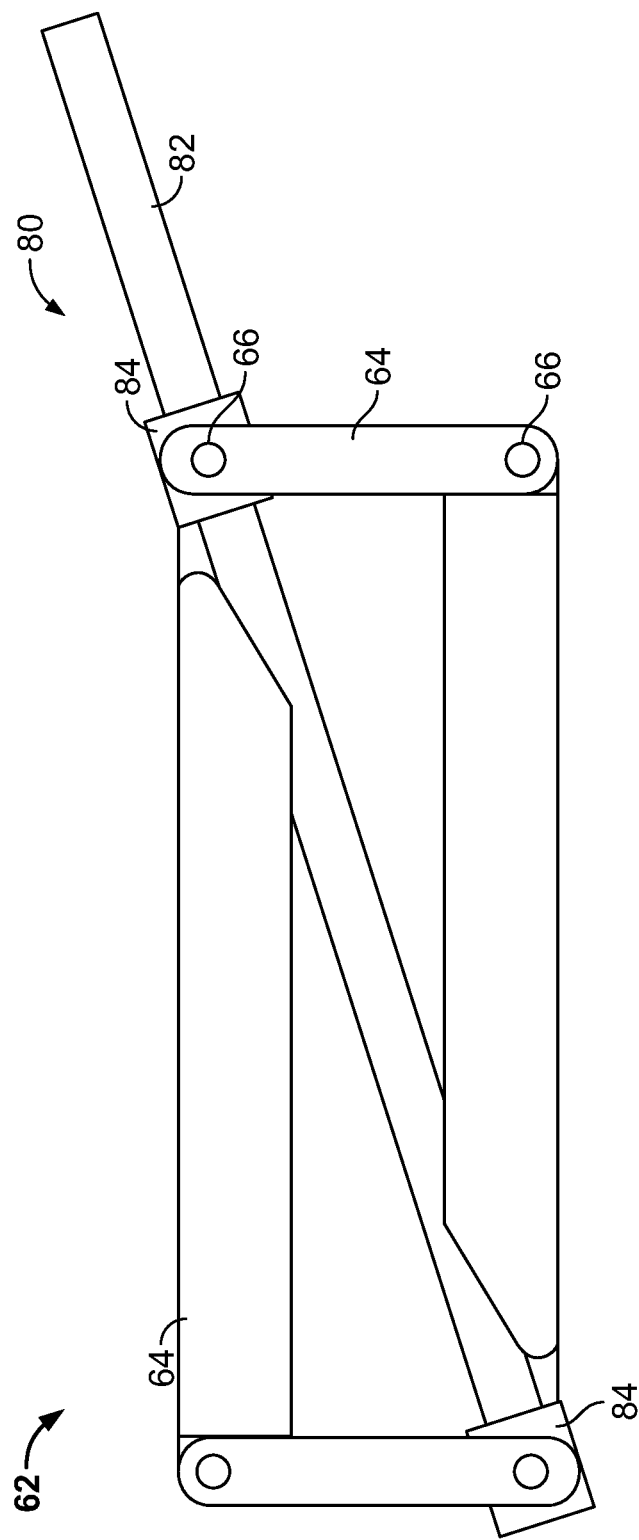
FIG. 46 is a plan view of the intervertebral cage of FIG. 45 in an expanded configuration.
Figure 47:
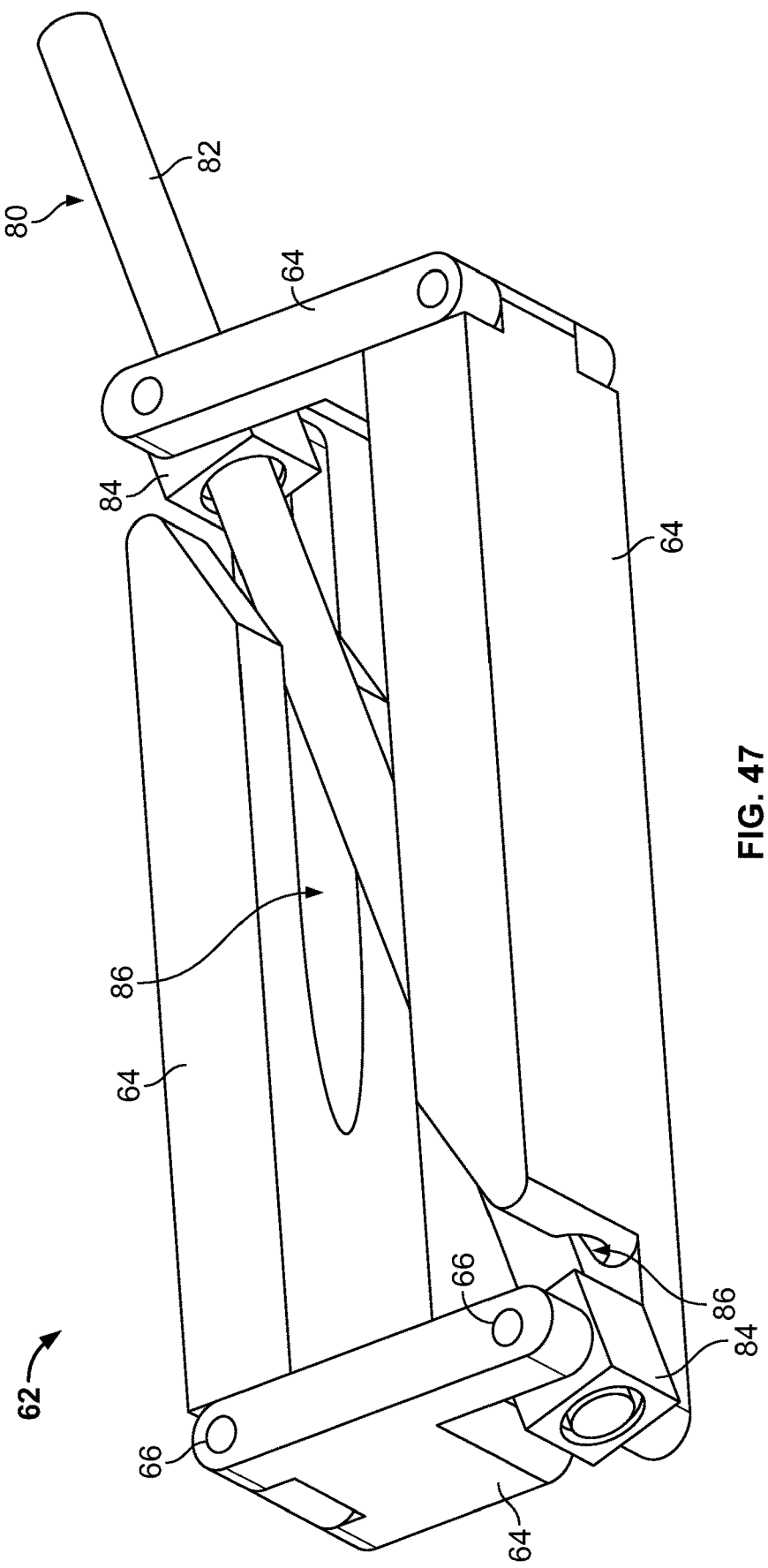
FIG. 47 is a perspective view of the intervertebral cage of FIG. 46.

Another implementation of the intervertebral cage 62 is shown in FIGS. 45-50 that include the use of a diagonally oriented draw bolt 80. FIGS. 45-47, for example, show a four-bar linkage (similar to the cage described above) that includes four links 64 interconnected by hinges 66. Two corners of the cage 62, however, are transfixed by the draw bolt 80 which includes a shaft 82 and a pair of nuts 84.

The shaft 82, for example, may be a threaded rod that is configured to extend through threaded openings in the nuts 84. The nuts 84 are positioned at the two diagonally opposing corners of the four-bar linkage. Each nut includes a pin 68 that extends into adjacent linkage ends that sandwich the nut between them. In this manner, the two adjacent links 64 can rotate relative to the nut 84. Each of the links also may include a scallop 86 or other adaptive space configured to allow the draw bar to achieve a collapsed position, such as is shown in FIGS. 45 and 46. The hinges 66 not transfixed are comprised of a pin 68 extending through a collinear opening in interdigitated portions of the adjacent ends of the links, as shown in FIG. 47.

A portion of the shaft 82 of the draw bolt 80 may have an extended length off of one hinge. This facilitates rotation of the shaft 82 after implantation of the cage 62 in the collapsed condition, such as is shown in FIG. 45. The two nuts 84 are drawn toward each other by rotation of the shaft 82 which may have different handed threads (or the nuts have different handed threads) to cause them to move toward each other with uni-directional rotation. Rotation of the shaft 82, therefore, may result in the expanded configuration shown in FIGS. 46 and 47.

Figure 48:
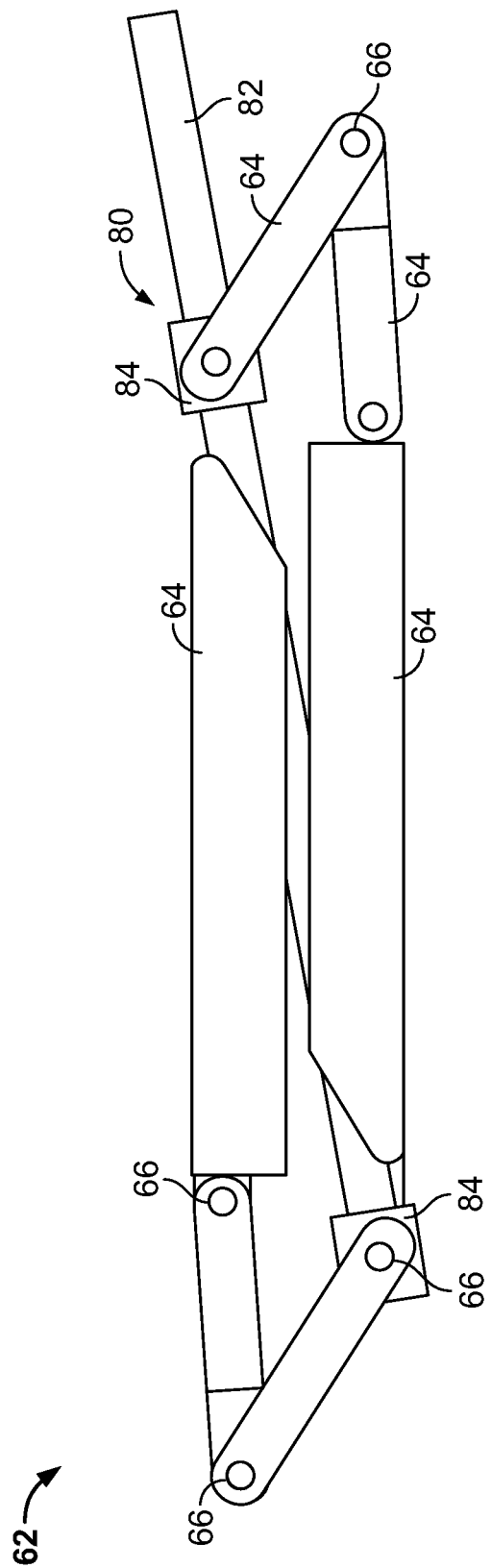
FIG. 48 is a plan view of a collapsed, six-bar intervertebral cage.
Figure 49:
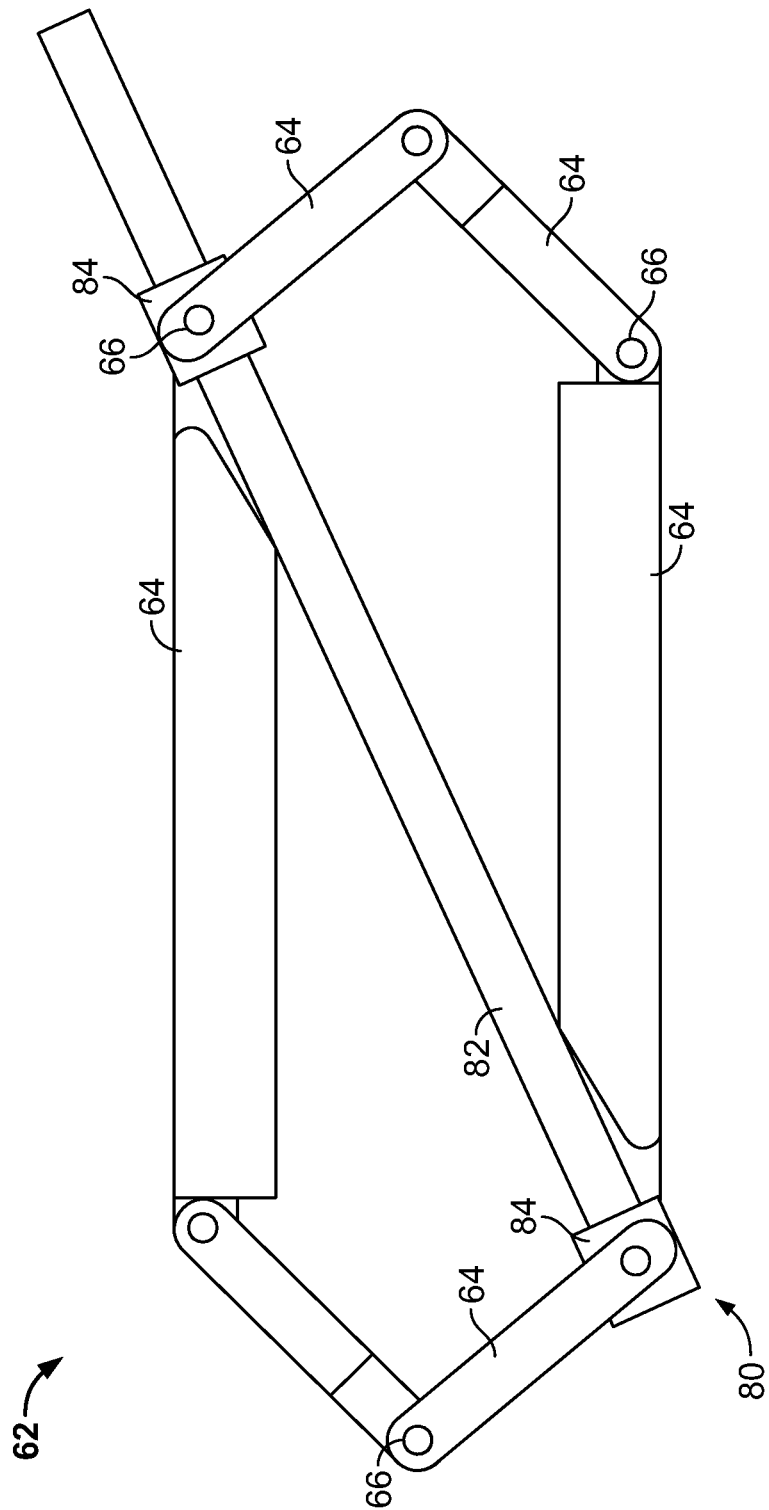
FIG. 49 is a plan view of the intervertebral cage of FIG. 48 in an expanded configuration.
Figure 50:
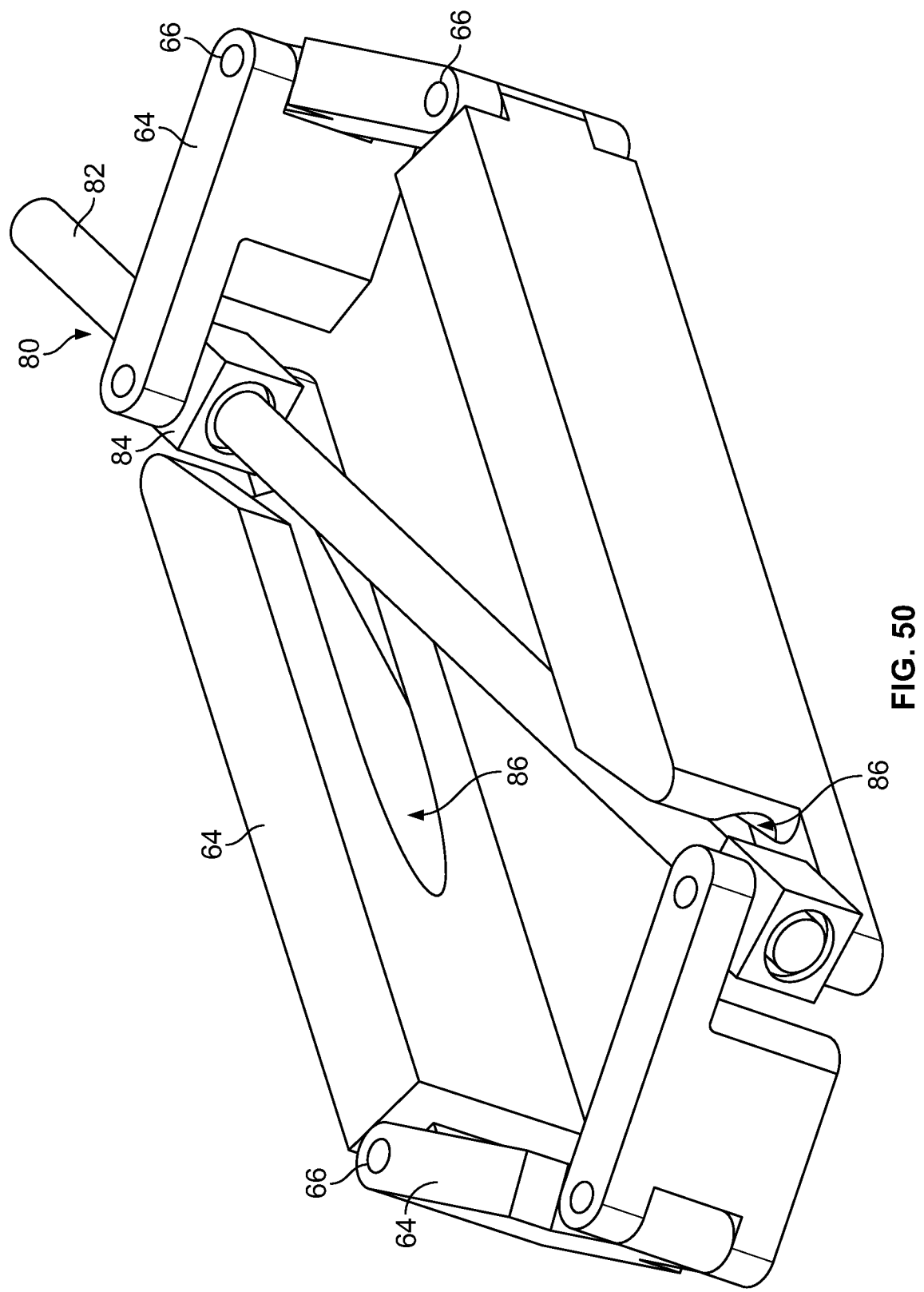
FIG. 50 is a perspective view of the intervertebral cage of FIG. 49.

Additional numbers of links 64 could be employed, such as 5, 6, 8 or additional links, although even link numbers have symmetrical expansion characteristics. FIGS. 48-50, for example, show use of six links 64 moving from a collapsed configuration (FIG. 48) to an expanded configuration (FIGS. 49-50) by way of rotation of the shaft 82 of the draw bolt 80.

Figure 51:
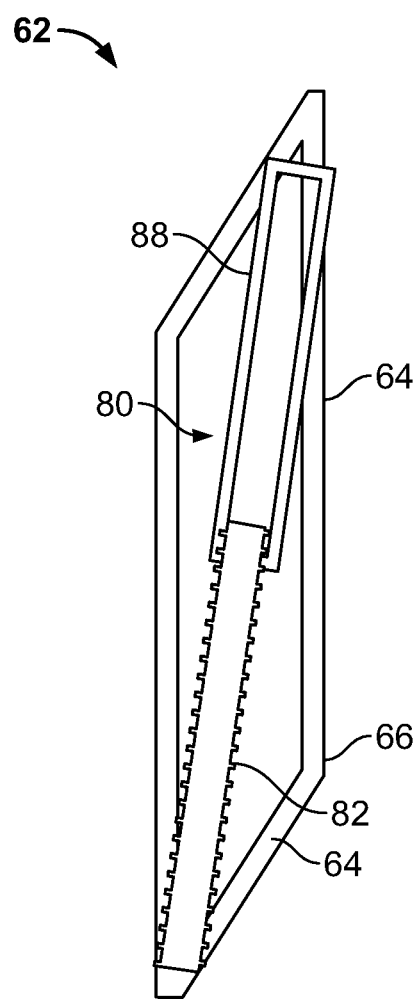
FIG. 51 is a schematic of another intervertebral cage in a collapsed configuration.
Figure 52:
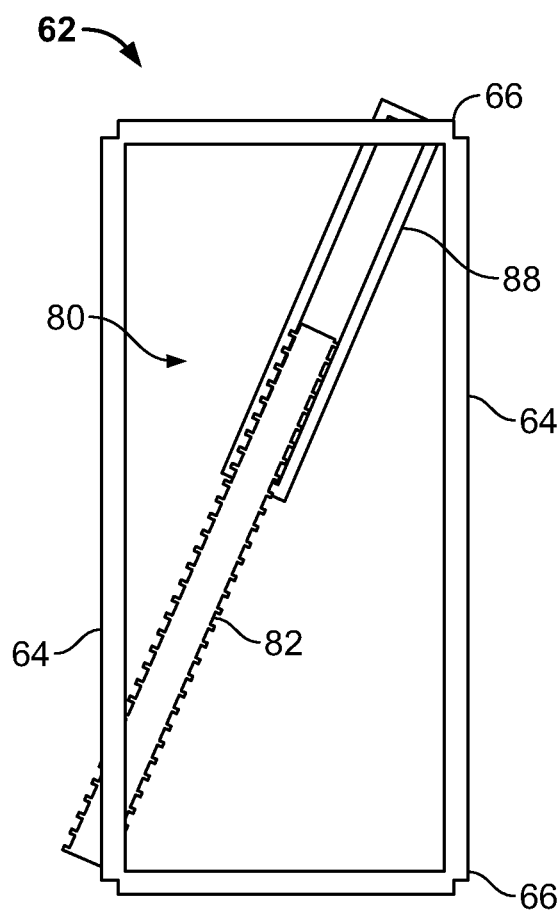
FIG. 52 is a schematic of the intervertebral cage of FIG. 51 in an expanded configuration.

FIGS. 51 and 52 show a variation wherein the draw bolt 80 includes a threaded shaft 82 which can reciprocate into and out of an internally threaded sleeve 88.

Figure 53:
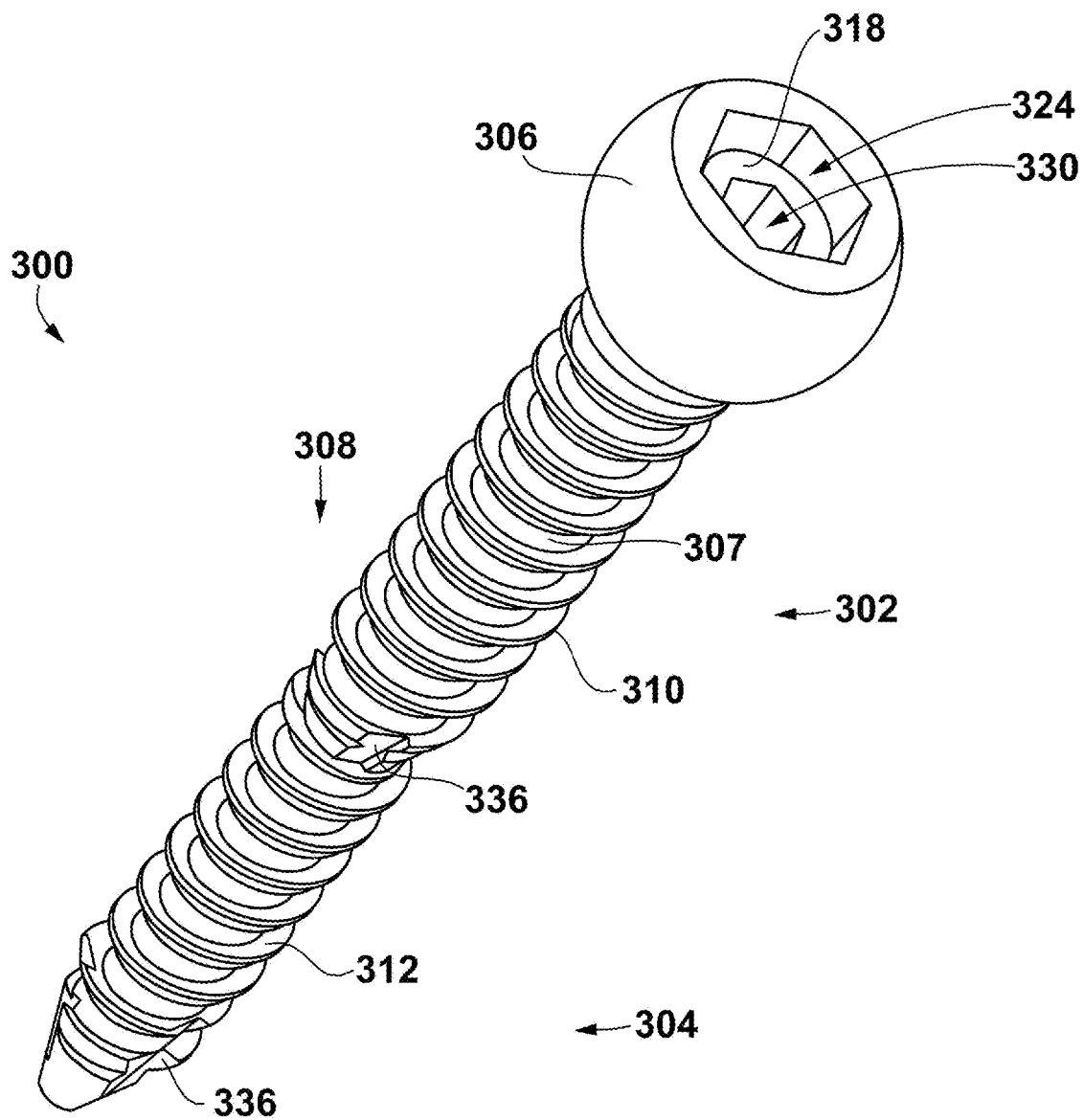
FIG. 53 is a perspective view of an embodiment of a bone screw.
Figure 54:
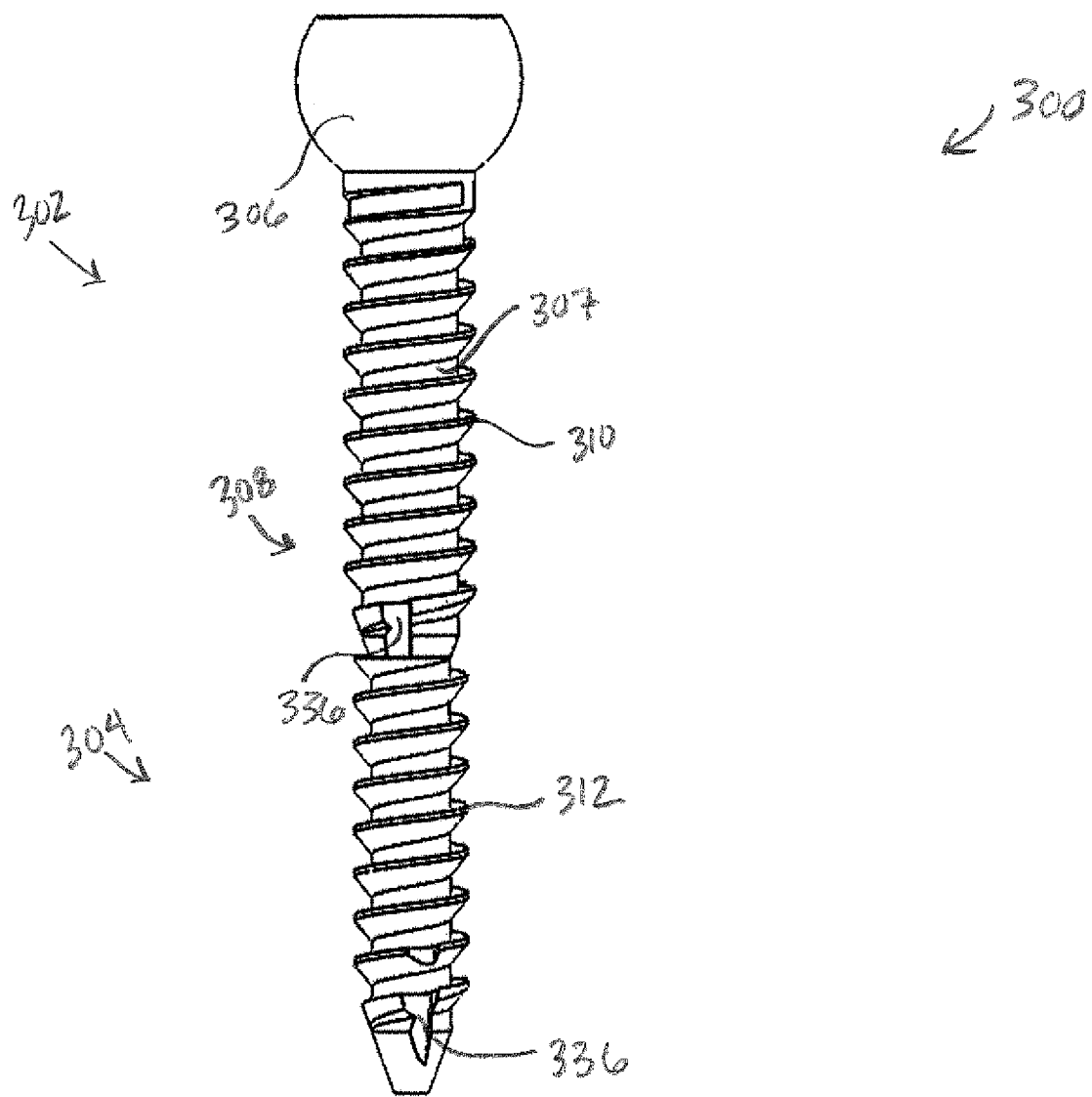
FIG. 54 is a side view of the bone screw embodiment of FIG. 53.
Figure 55:
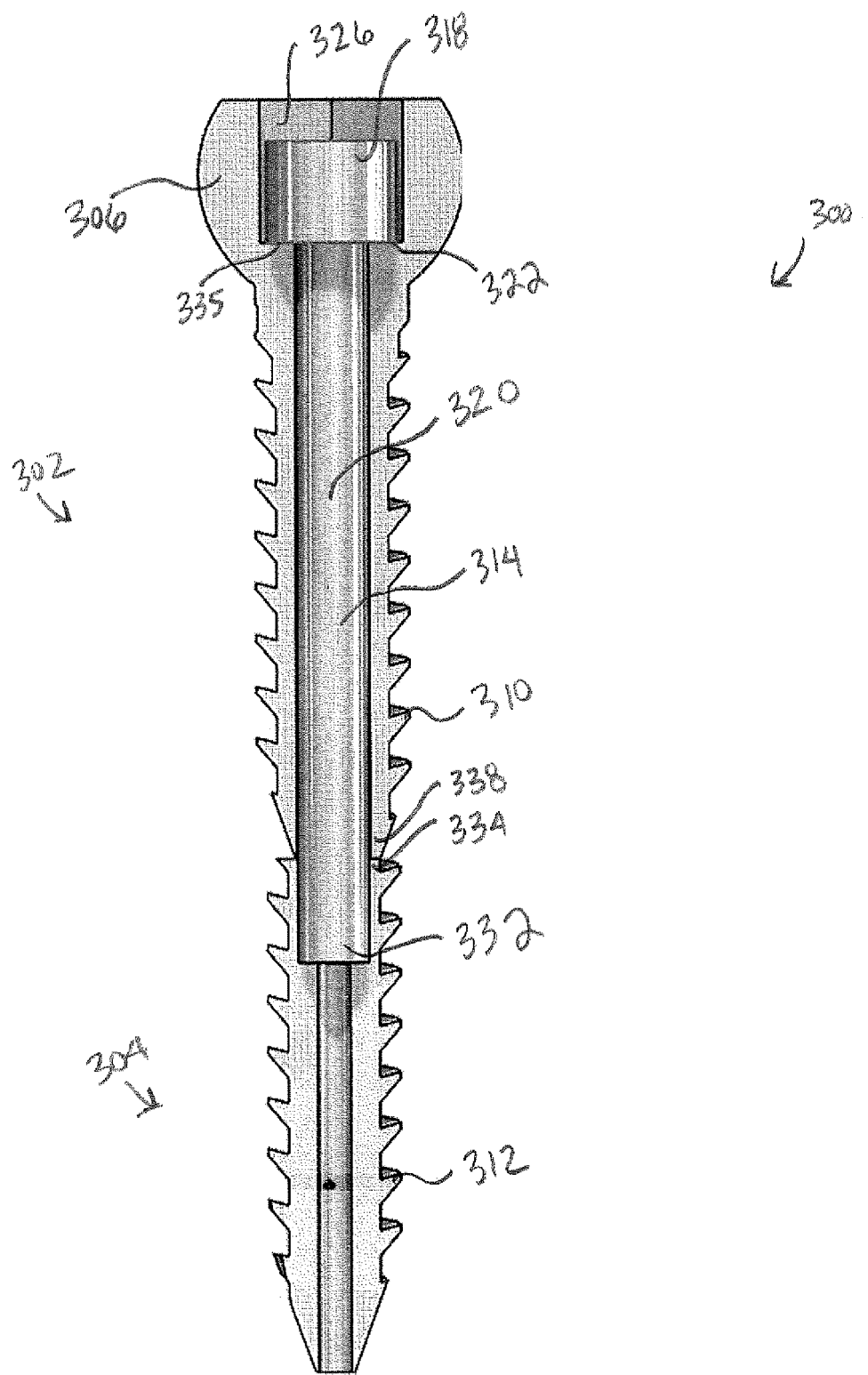
FIG. 55 is a sectional side view of the bone screw embodiment of FIG. 53.
Figure 56:
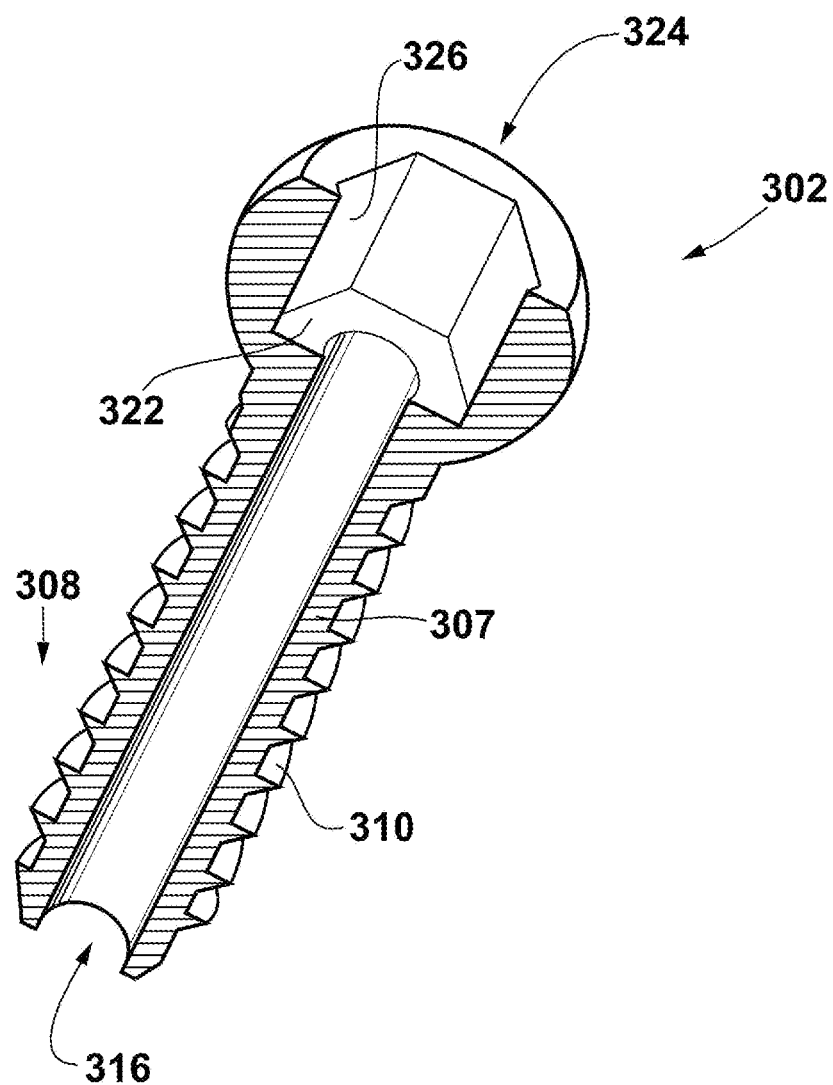
FIG. 56 is sectional perspective view of the proximal piece of the bone screw embodiment of FIG. 53.

FIG. 53 shows a perspective view of a bone screw 300 having separately rotatable proximal and distal pieces 302, 304 and an inner post 320. FIG. 54 shows a side view of the bone screw 300 of FIG. 53. Proximal piece 302 includes a proximal head 306 and a body 307. The body 307 extends between the proximal head 306 and a distal end 308 of the body. A set of threads 310 extends along an external surface of the body 307. The proximal head 306 has a semi-spherical external shape. A proximal end surface of the proximal head 306 defines a non-cylindrically shaped receptacle 324 that extends axially into the head 306. For example, the receptacle 324 shown in FIGS. 53, 55, and 56 is shaped like a hexagonal prism. The proximal head 306 further defines an inner, distal end surface 322 of the receptacle 324 that lies within a plane that is transverse to a central axis A-A of the proximal piece 302. The receptacle 324 has a height $H_R$. The proximal piece 302 also defines a central lumen 316 that extends axially from the distal end surface 322 of the receptacle 324 to the distal end 308 of the proximal piece 302. The central lumen 316 is shown in FIG. 56.

Figure 58:
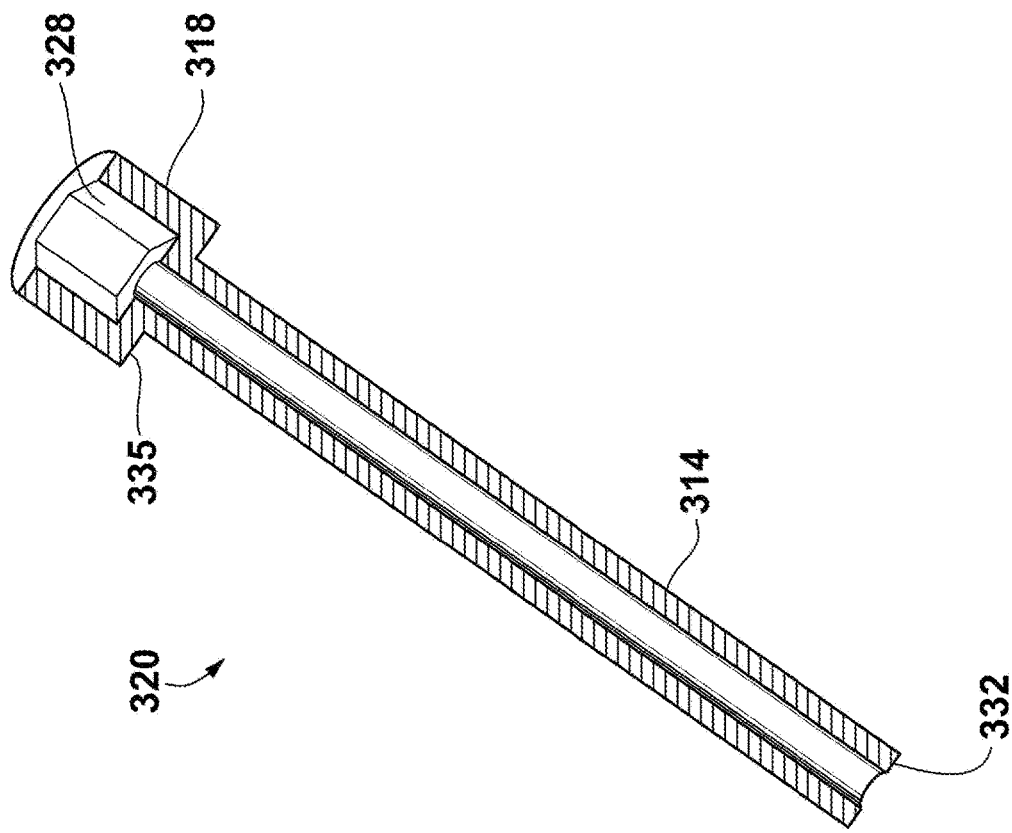
FIG. 58 is a perspective sectional view of the inner post of the bone screw embodiment of FIG. 53.
Figure 57:
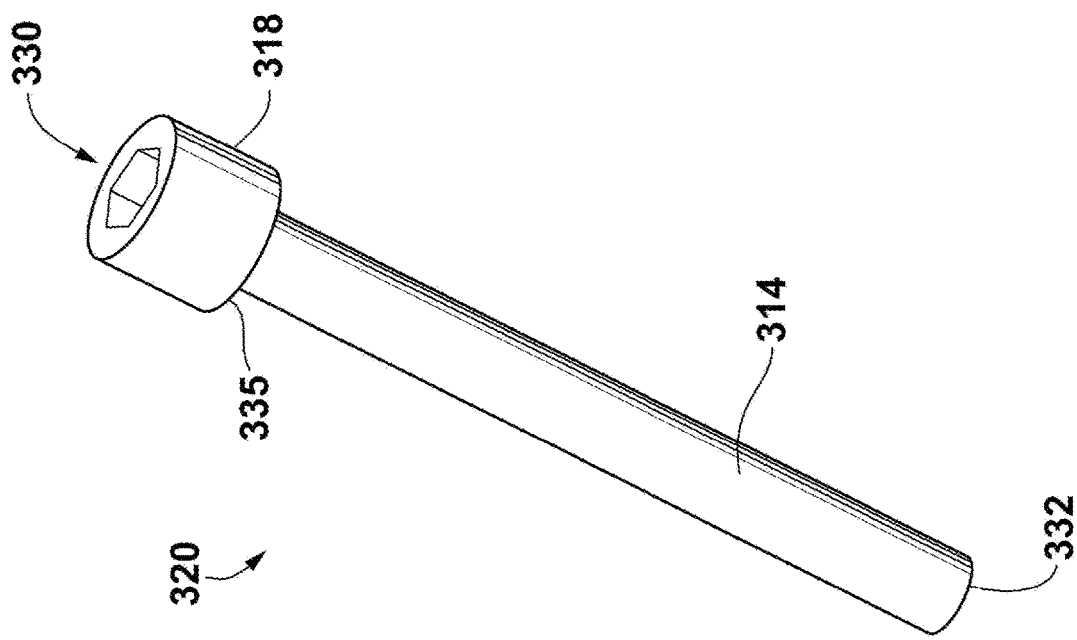
FIG. 57 is a perspective view of the inner post of the bone screw embodiment of FIG. 53.

FIG. 57 shows a side perspective view of the inner post 320, while FIG. 58 shows a cross sectional perspective view of the same. The inner post 320 has a shaft 314 with a proximal end and a distal end 332. The post 320 also includes a proximal head 318 at the proximal end of the shaft 314. The proximal head 318 has a cylindrically shaped outer surface and an outer, distal end surface 335 that extends through a plane that is transverse to a central axis B-B of the inner post 320. A diameter $D_P$ of the proximal head 318 is greater than a diameter $D_S$ of the shaft 314. And, the proximal head 318 has a height $H_P$ that is less than the height $H_R$ of the receptacle 324. A proximal end surface of the proximal head 318 of the post 320 defines a second non-cylindrical receptacle 330 that extends axially into the head 318.

Figure 59:
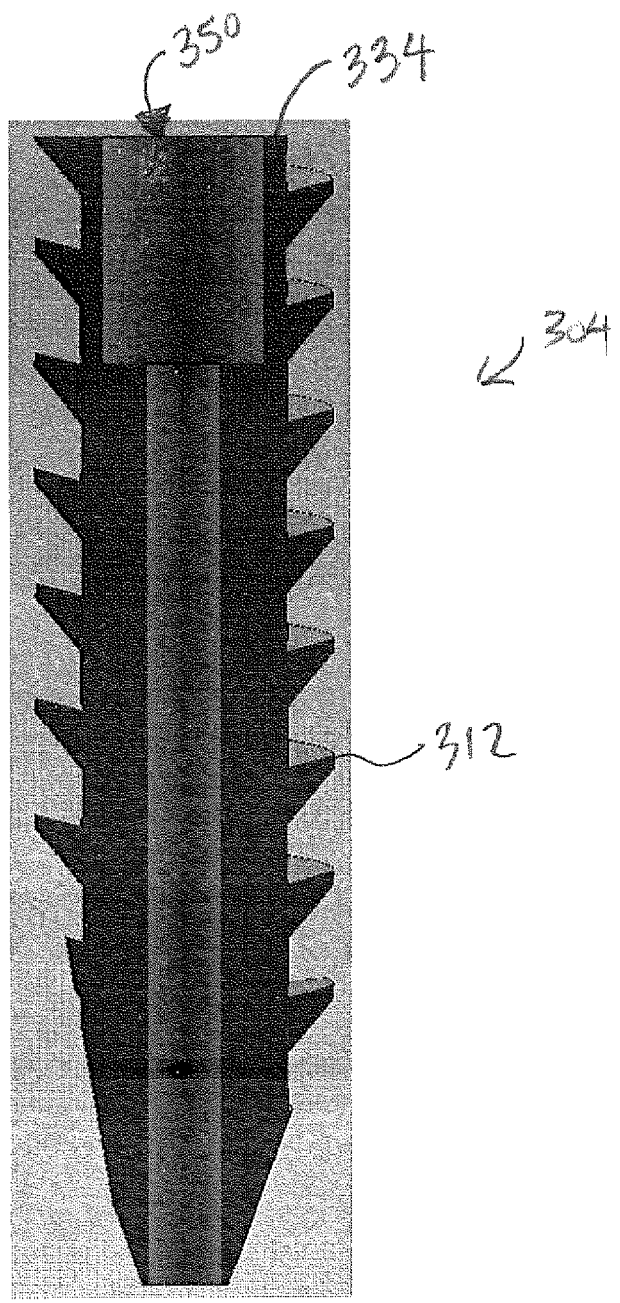
FIG. 59 is a perspective sectional view of the distal piece of the bone screw embodiment of FIG. 53.
Figure 66:
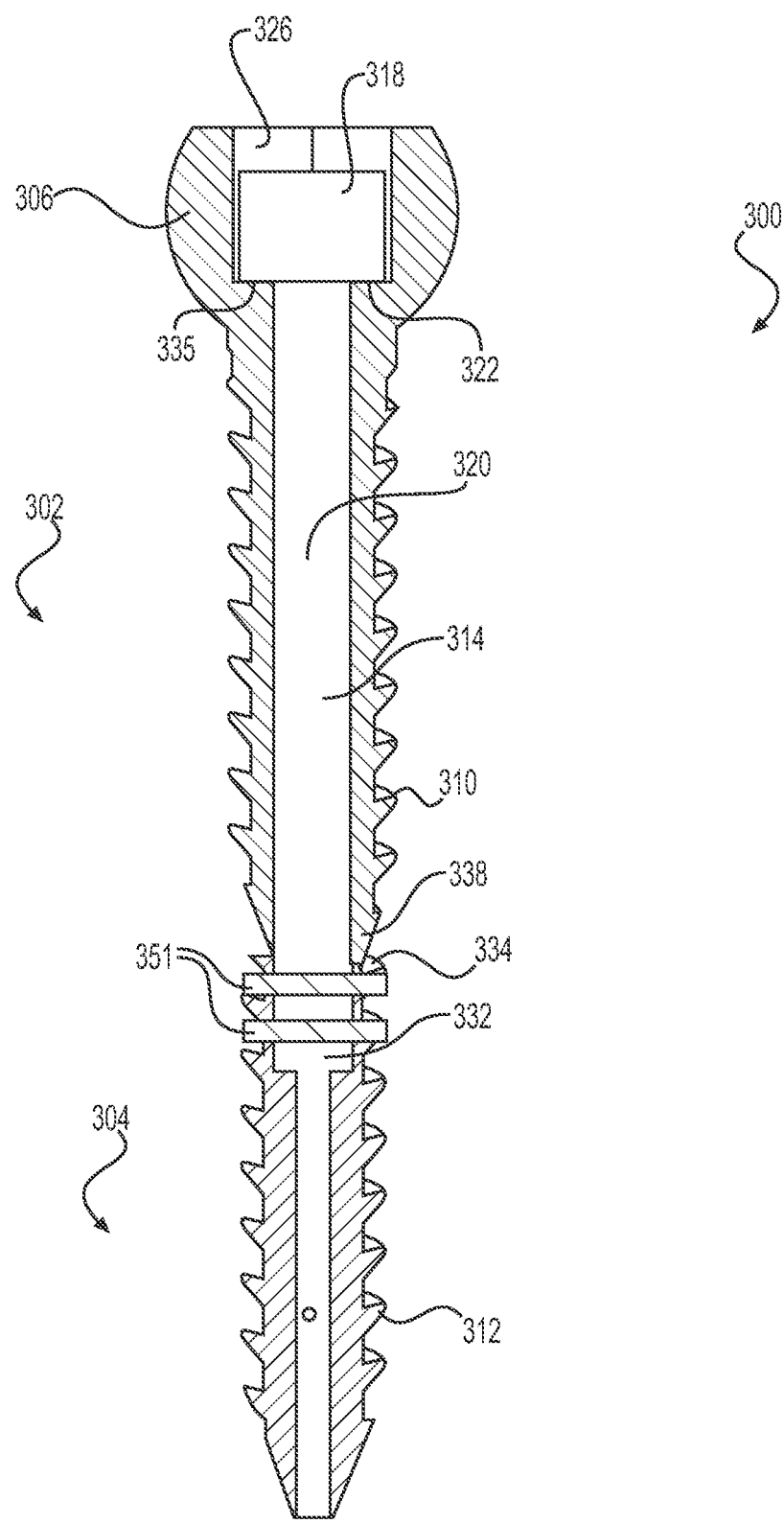
FIG. 66 shows an embodiment of a bone screw wherein the shaft of the inner post is affixed to the distal piece with pins.

An external surface of the distal piece 304 includes a second set of threads 312. In addition, the distal piece 304 defines a receptacle 350 that extends axially from a proximal end surface 334 of the distal piece 304. As shown in FIGS. 55 and 59, the distal end 332 of the shaft 314 is fixedly attached to the proximal end surface 334 of the distal piece 304 by press fitting the distal end 332 of the shaft 314 into the receptacle 350. However, in other implementations, the inner post 320 and the distal piece 304 can be fixedly attached in a variety of ways, including welding or, as shown in FIG. 66, the use of pins 351 that extend through the walls of both the distal piece 304 and the inner post 320. Because the inner post 320 is fixedly attached to the distal piece 304, they can be rotated together, for example, when the second non-cylindrical receptacle 330 is engaged with a complementarily shaped tool.

The inner post 320 and the distal piece 304 can be cannulated to enable sliding over a guidewire, as shown in FIGS. 53-59.

When assembled, the shaft 314 of the inner post 320 extends through the central lumen 316 and is fixedly attached to the distal piece 304. In addition, the outer distal end surface 335 of the proximal head 318 of the inner post 320 abuts the inner distal surface 322 of the non-cylindrical receptacle 324 defined by the proximal head 306 of the proximal piece 302.

Advantageously, with the bone screw fully assembled as shown in FIGS. 53-55, the non-cylindrical receptacle 324 can be engaged and rotated independently of the second non-cylindrical receptacle 330, enabling separate rotation of proximal piece 302 and the distal piece 304. For example, the distal piece 304 could be separately rotated from the proximal piece 302 using a tool having a central column shaped to complement to an inner surface 332 of the second non-cylindrical receptacle 330. Similarly, the proximal piece 302 could be separately rotated from the distal piece 304 by engaging a tool having an external surface that is shaped to complement the first non-cylindrical receptacle 324. By having the height $H_R$ of the receptacle 324 be greater than the height $H_P$ of the proximal head 318 of the post 320, the tool for rotating the proximal piece 302 is able to fit within the receptacle 324 and engage an inner surface 326 of the receptacle. To engage both receptacles 324, 330 with the same tool the central column of the tool can be surrounded by an outer sheath shaped to complement the non-cylindrical receptacle 324. The central column of the tool could be separately rotatable from the outer sheath, or the central column and outer sheath could rotate together to drive simultaneous rotation of proximal and distal pieces 302, 304.

The non-cylindrical receptacles 324, 330 shown in FIGS. 53-58 have a hexagonal shaped cross section, but the receptacles could be any non-cylindrical shape that facilitates engagement with complementary driving tools. And, although the outer surface of proximal head 318 is cylindrical as shown, the outer surface of the proximal head 318 can be any shape that enables its rotation within the non-cylindrical receptacle 324.

As shown in the side sectional view of FIG. 55, proximal axial movement of the proximal piece 302 along the shaft 314 is restricted by abutment of the distal surface 322 of the receptacle 324 and the distal end surface 335 of the proximal head 318 of the inner post 320. Distal axial movement of the proximal piece 302 along the shaft 314 is restricted by abutment of the distal end 308 of the proximal piece 302 with the proximal end surface 334 of the distal piece 304. While axial sliding is restricted, sufficient tolerances are maintained between abutting surfaces to allow for rotation of the proximal piece 302 relative to the proximal head 318 and the distal piece 304. Given this advantageous design, according to some implementations, it is possible to assemble the bone screw 300 with just the proximal piece 302, the distal piece 304, and the inner post 320. Reducing the number of parts lessens the risk of a part becoming detached from the main assembly, which would require additional surgical intervention.

In some embodiments of bone screw 300, distal piece 304 has a smaller diameter than proximal piece 302. In some embodiments, the first set of threads 310 and the second set of threads 312 have an equivalent pitch and lead. The first and/or second sets of threads 310, 312 can include notches 336, or self-tapping slots, that enable the threads to cut the bone. The notches 336 are axially extending channels cut into the outer surfaces of the proximal and distal pieces 302, 304. As shown in FIG. 54, the notches 336 extend proximally from positions at or adjacent to the distal ends of proximal and distal pieces 302, 304, cutting through multiple crests of threads 310, 312. The notches 336 can, in some implementations, have a tapered shape that narrows approaching the distal end of the proximal or distal piece 302, 304. The notches 336 can, in some implementations, cut through the threads 310, 312 and into the outer wall of the proximal or distal piece 302, 304. The thread type can be buttress threads for unidirectional load bearing, as shown in FIG. 55. In some embodiments, such as the one shown in FIG. 63 and discussed in greater detail below, the thread type can be a combination of buttress threads and reverse buttress threads. Alternatively, the thread type can be, for example, Unified, American National, Sharp V, Metric, Whitworth, or Square The bone screw 300 can be used to move a first bone in relation to a second bone. This movement can be a compression of adjacent bones or a decompression of adjacent bones. In some cases, the procedure can begin with placement of a guidewire within a hole that has been drilled into the bones, followed by moving the cannulated bone screw 300 over the guidewire and into the desired surgical location. However, the procedure can also be performed without a guidewire. Either way, the distal piece 304 is positioned at least partially within a distally positioned bone. In some cases, the proximal end surface 334 of the distal piece 304 can be positioned within a gap defined between two adjacent bones. The proximal piece 302 is positioned at least partially within the proximally positioned bone. The distal end of the proximal piece 302 can also be positioned within the gap between the two adjacent bones. One or the other of the proximal or distal pieces 302, 304 is then rotated, while the other is held in a fixed position (both axially and rotationally). With the two pieces axially fixed within the bone, the rotation of one of the two pieces shifts axial forces to the bones within which it is lodged. The direction of the rotation is responsible for the direction of movement of the bones. Hence the bone screw 300 can be used in both compression and decompression procedures. As used herein, the term "bone" refers to whole bones and bone fragments.

Figure 64:
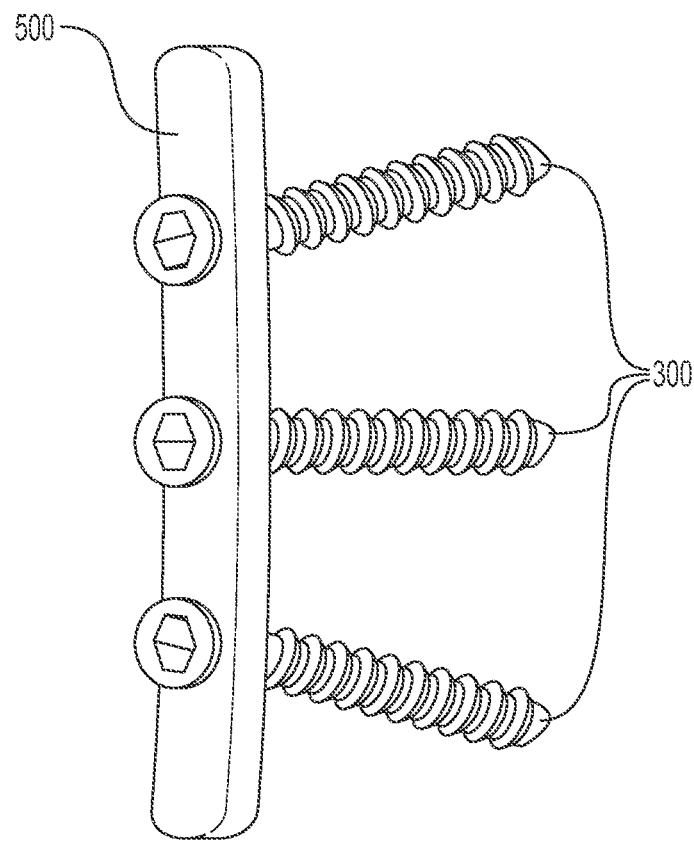
FIG. 64 shows bone screws being used in conjunction with a bone plate.
Figure 65:
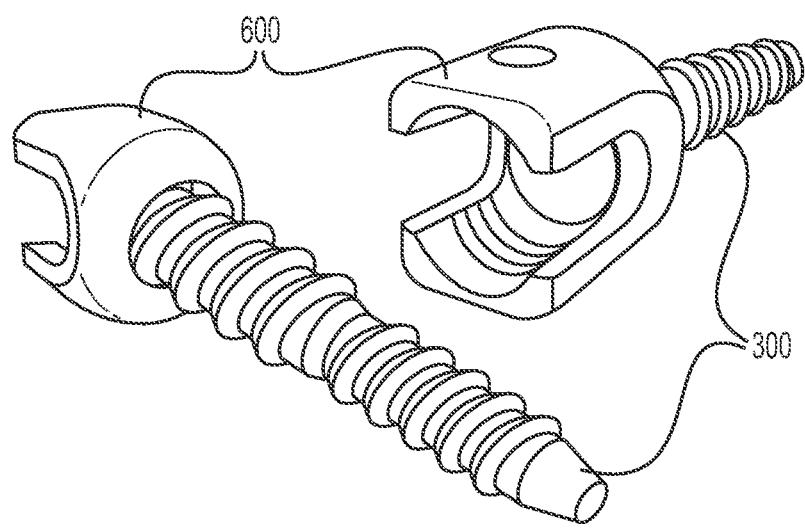
FIG. 65 shows bone screws being used in conjunction with tulips.

Bone screw 300 can be used in surgical procedures that involve additional components. For example, the semispherical shape of the proximal head 306 of proximal piece 302 facilitates its use in, for example, the proximal housing of a polyaxial screw. For example, as shown in FIG. 65, the semispherical head 306 of screw 300 can cooperate with the tulip 600 of a pedicle screw, acting as the ball of the ball and socket joint. In certain procedures, bone screw 300 can be utilized in conjunction with a bone plate 500, as shown in FIG. 64.

Figure 60:
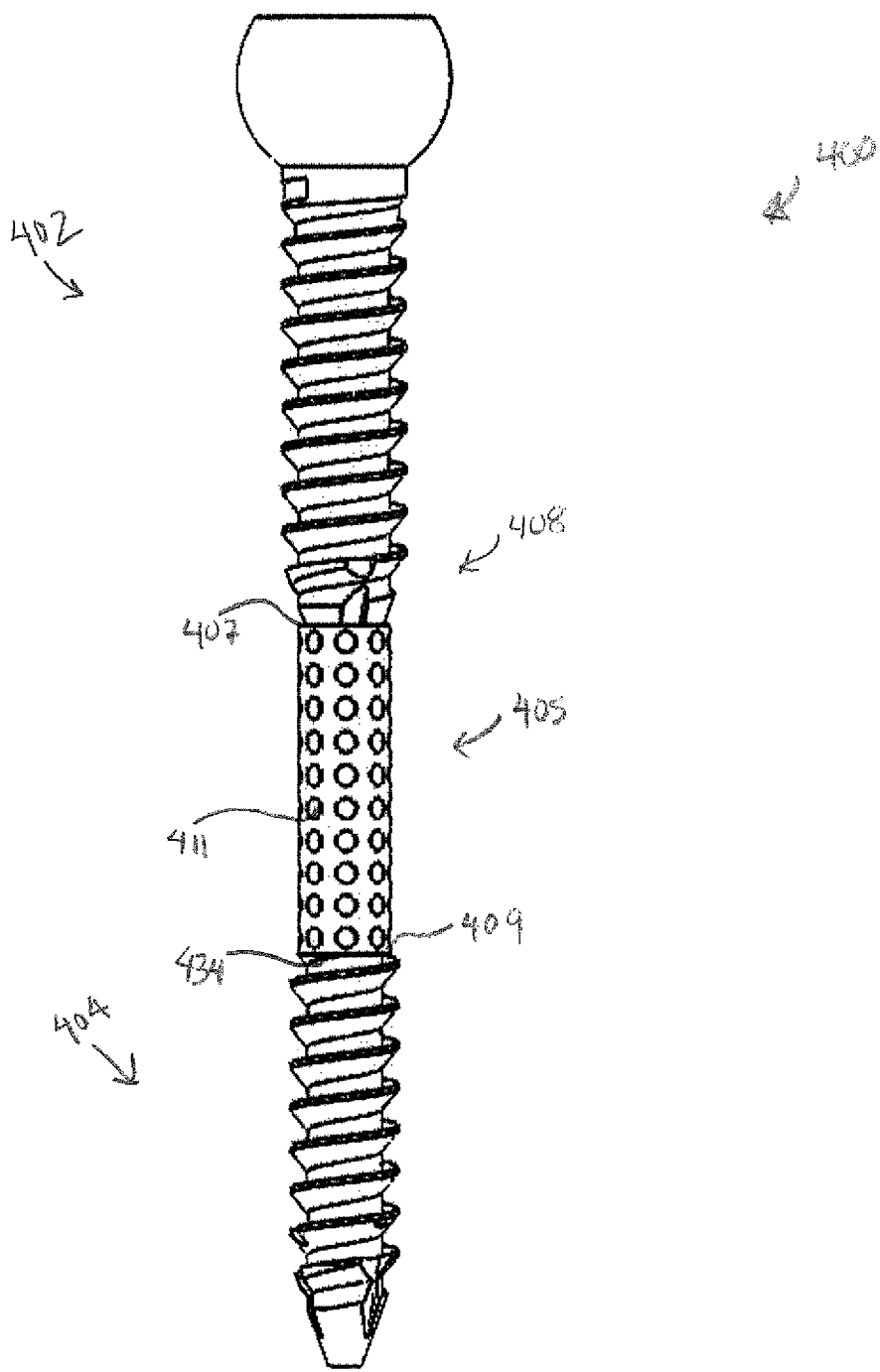
FIG. 60 is a side view of an embodiment of a bone screw.
Figure 61:
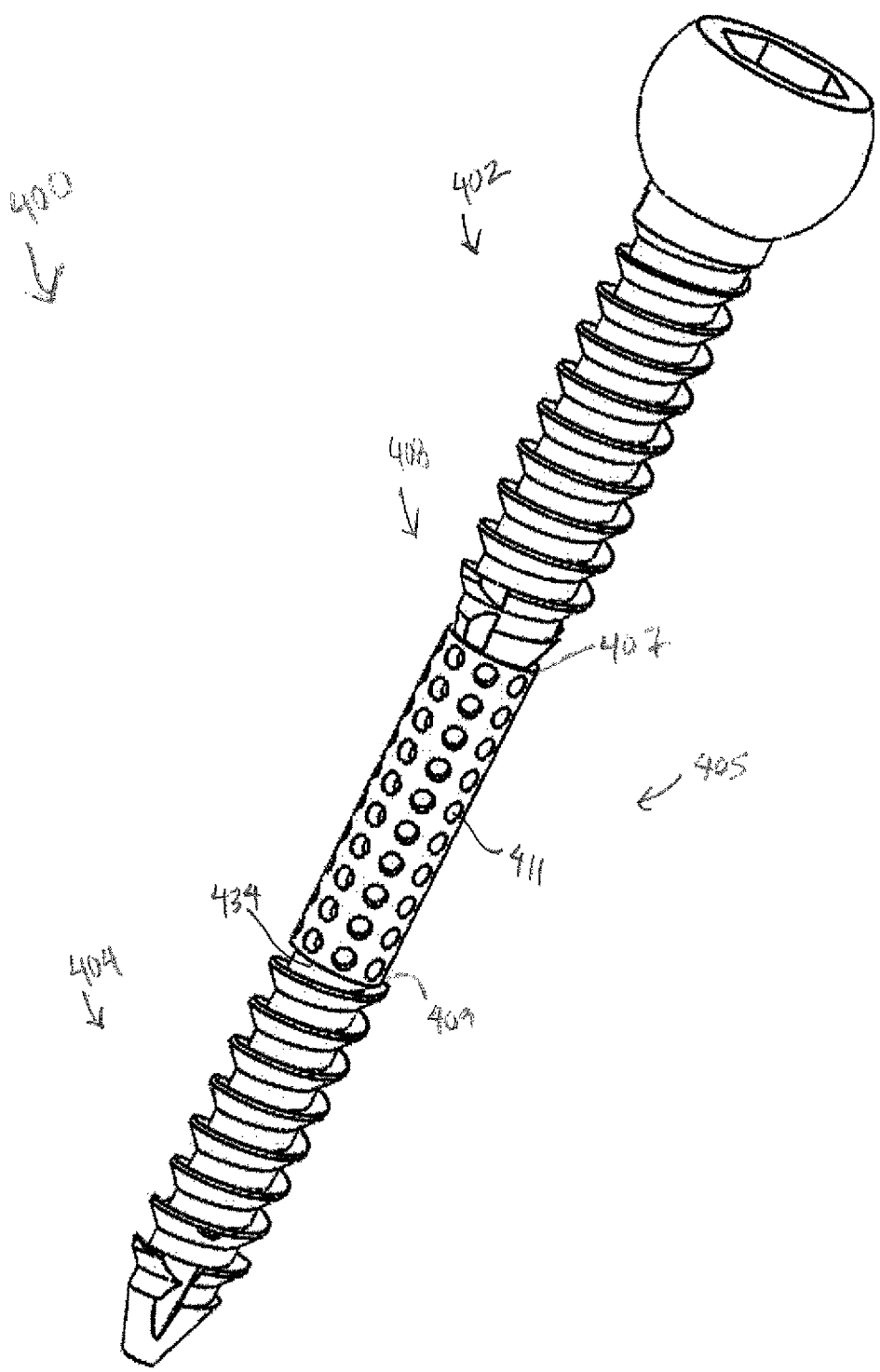
FIG. 61 is a perspective view of the bone screw embodiment of FIG. 60.
Figure 62:
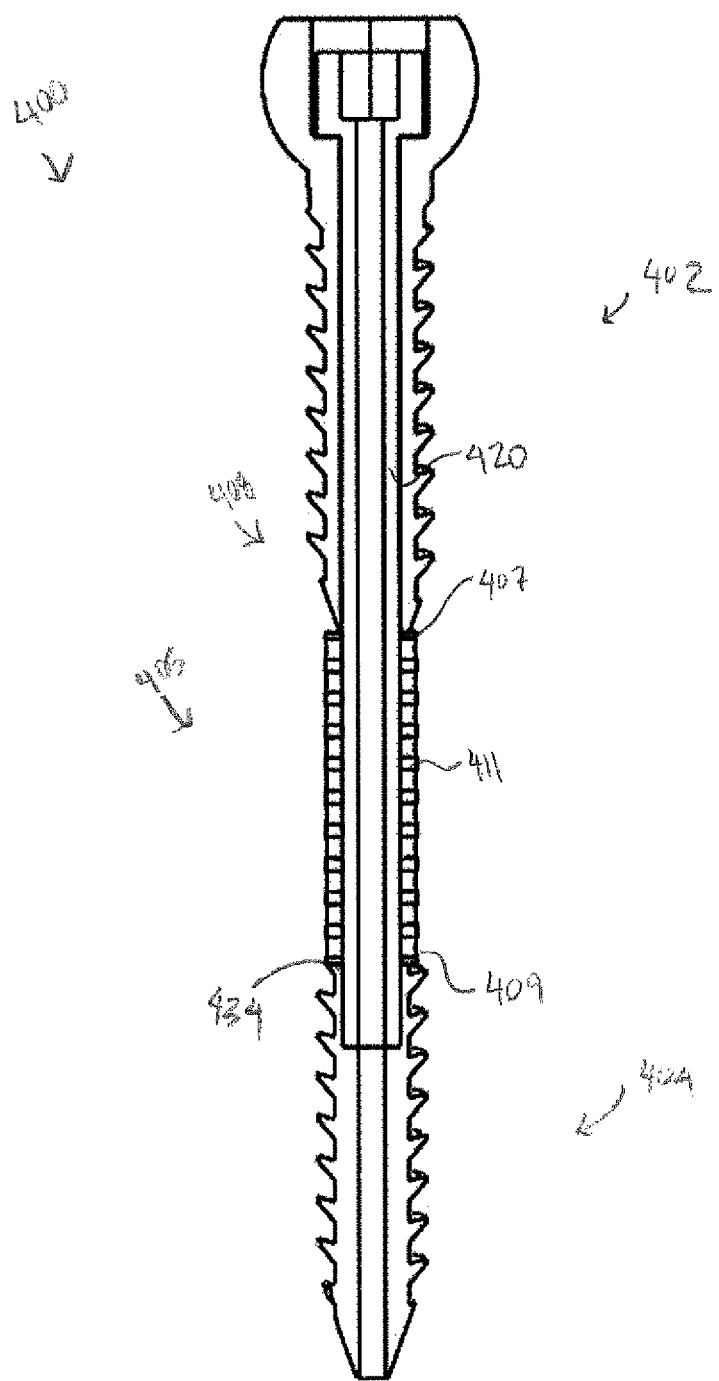
FIG. 62 is a cross sectional view of the bone screw embodiment of FIG. 60.

FIGS. 60-62 show an embodiment of a bone screw 400 that includes a proximal piece 402, a distal piece 404, an inner post 420, and a cage 405. Cage 405 includes a proximal end 407 and a distal end 409. Cage 405 has a shape (e.g., cylindrical) and outer diameter that is equivalent to or smaller than the outer diameter of proximal end 434 of distal piece 404. The cage 405 defines axially, between the ends 407, 409, an opening through which the inner post 420 extends. The proximal end 434 of the distal piece 404 abuts the distal end 409 of the cage 405, and the distal end 417 of the proximal piece 402 abuts the proximal end 407 of the cage 405. The cage 405 has a cylindrical shape as shown, but in other implementations, the cage may have a non-cylindrical shape, such as a rectangular or triangular shaped prism. In some embodiments, the cage 405 is formed of a compliant material, such that compression of the ends 407, 409 causes cage 405 to spread radially.

Cage 405 is configured to receive bone graft material or bone growth promoting materials such as bone morphogenic protein (BMP). The cage 405 defines a plurality of radial openings 411 which allow bone growth promoters held within the cage to leak, diffuse, or otherwise access (or be accessed by) adjacent bone structures so as to promote fusion. The radial openings may be round, as shown in FIGS. 60-63, or they may be non-round, such as square, openings when, for example, the cage 405 is formed of axially aligned rings connected by radially spaced longitudinal connectors (as in FIGS. 5-6, described above). Or, for example, the cage may be a lattice structure, defining diamond shaped openings. Adjacent radial openings 411 are axially aligned in columns and rows in the figures shown, but in other implementations, adjacent radial openings may be arranged in an offset or irregular pattern.

Figure 63:
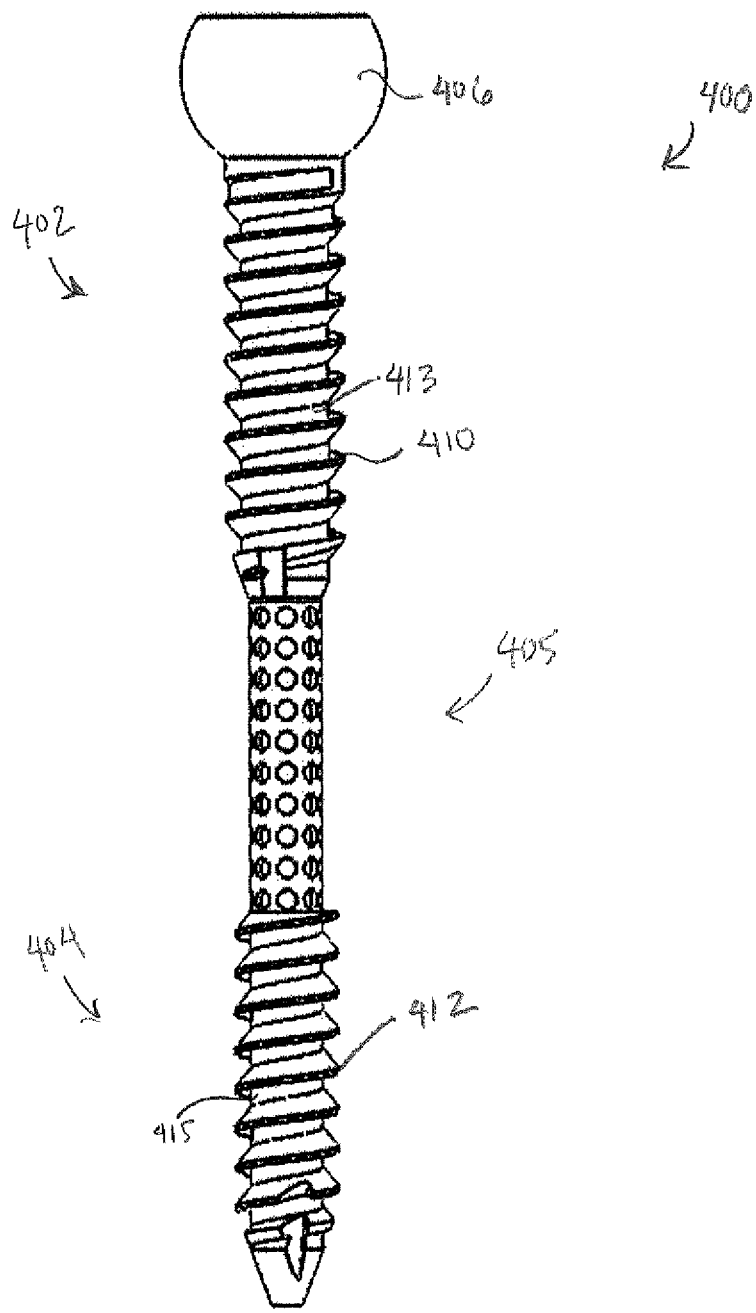
FIG. 63 is a side view of an embodiment of a bone screw.

FIG. 63 shows another embodiment of a bone screw 400. In this embodiment, the first set of threads 410 on the proximal piece 402 are buttress threads angled toward the proximal head 406 (i.e., an acute angle is formed with external surface 413 of the proximal piece 402 on the proximal side of the first set of threads 410 and an obtuse angle is formed with the external surface 413 of the proximal piece 402 on the distal side of the first set of threads 410). In contrast, the second set of threads 412 on the distal piece 404 are reverse buttress threads angled toward the distal end of the bone screw 400, forming an acute angle with the external surface 415 of the distal piece 404 on the distal side of the second set of threads 412 and an obtuse angle with the external surface 415 of the distal piece 404 on the proximal side of the second set of threads 412. This embodiment could be especially advantageous for distraction procedures.

A number of aspects of the systems, devices and methods have been described. Nevertheless, it will be understood that various modifications may be made without departing from the spirit and scope of the disclosure. Accordingly, other aspects are within the scope of the following claims.

That which is claimed:

1. A bone screw comprising;
a proximal piece comprising a proximal head, a body, and a first set of threads defined on an external surface of the body, the proximal piece defining a central lumen, and a proximal end surface of the proximal head defining a first non-cylindrical receptacle that extends axially into the proximal head;
a distal piece having an external surface defining a second set of threads;
an inner post comprising a shaft and a proximal head, wherein the shaft extends through the central lumen of the proximal piece and is fixedly attached to the distal piece by welding, and the proximal head of the inner post abuts an inner distal surface of the first non-cylindrical receptacle;
a proximal end surface of the proximal head of the inner post defines a second non-cylindrical receptacle that extends axially into the proximal head of the inner post;
wherein the proximal piece is configured to be rotated separately via engagement of the first non-cylindrical receptacle, and the distal piece is configured to be rotated separately via engagement of the second non-cylindrical receptacle.

2. The bone screw of claim 1, wherein axial movement of the proximal piece along the shaft of the inner post is restricted between a proximal end of the distal piece and the proximal head of the inner post.

3. The bone screw of claim 2, wherein the bone screw consists of the proximal piece, the distal piece, and the inner post.

4. The bone screw of claim 2, wherein a pitch of the first set of threads is the same as a pitch of the second set of threads.

5. The bone screw of claim 2, wherein the distal piece has a smaller diameter than the proximal piece.

6. The bone screw of claim 1, wherein the inner post and the distal piece are cannulated.

7. The bone screw of claim 1, wherein the first non-cylindrical receptacle has a hexagonally shaped cross sectional shape.

8. The bone screw of claim 1, wherein the second non-cylindrical receptacle has a hexagonally shaped cross sectional shape.

9. The bone screw of claim 1, wherein an outer surface of the proximal head of the inner post is cylindrical.

10. The bone screw of claim 1, wherein the proximal head of the proximal piece comprises a semi-spherical outer surface.

11. The bone screw of claim 1, wherein the first set of threads comprises notches.

12. The bone screw of claim 1, wherein the second set of threads comprises notches.

13. The bone screw of claim 1, configured to engage with a bone plate.

14. The bone screw of claim 1, configured to engage with a tulip.

15. The bone screw of claim 1, further comprising a cage.

16. The bone screw of claim 1, wherein the first set of threads is angled toward the proximal head of the proximal piece, and the second set of threads is angled toward a distal end of the bone screw.

17. A bone screw comprising;
a proximal piece comprising a proximal head, a body, and a first set of threads defined on an external surface of the body and angled toward the proximal head of the proximal piece, the proximal piece defining a central lumen, and a proximal end surface of the proximal head defining a first non-cylindrical receptacle that extends axially into the proximal head;
a distal piece having an external surface defining a second set of threads angled toward a distal end of the bone screw;
an inner post comprising a shaft and a proximal head, wherein the shaft extends through the central lumen of the proximal piece and is fixedly attached to the distal piece, and the proximal head of the inner post abuts an inner distal surface of the first non-cylindrical receptacle;
a proximal end surface of the proximal head of the inner post defines a second non-cylindrical receptacle that extends axially into the proximal head of the inner post;
wherein the proximal piece is configured to be rotated separately via engagement of the first non-cylindrical receptacle, and the distal piece is configured to be rotated separately via engagement of the second non-cylindrical receptacle.

18. The bone screw of claim 17, wherein axial movement of the proximal piece along the shaft of the inner post is restricted between a proximal end of the distal piece and the proximal head of the inner post.

19. The bone screw of claim 18, wherein the bone screw consists of the proximal piece, the distal piece, and the inner post.

20. The bone screw of claim 18, wherein a pitch of the first set of threads is the same as a pitch of the second set of threads.

21. The bone screw of claim 18, wherein the distal piece has a smaller diameter than the proximal piece.

22. The bone screw of claim 17, wherein the inner post and the distal piece are cannulated.

23. The bone screw of claim 17, wherein the shaft is welded to the distal piece.

24. The bone screw of claim 17, wherein the shaft and the distal piece are held together by one or more pins.

25. The bone screw of claim 17, wherein the first non-cylindrical receptacle has a hexagonally shaped cross sectional shape.

26. The bone screw of claim 17, wherein the second non-cylindrical receptacle has a hexagonally shaped cross sectional shape.

27. The bone screw of claim 17, wherein an outer surface of the proximal head of the inner post is cylindrical.

28. The bone screw of claim 17, wherein the proximal head of the proximal piece comprises a semi-spherical outer surface.

29. The bone screw of claim 17, wherein the first set of threads comprises notches.

30. The bone screw of claim 17, wherein the second set of threads comprises notches.

31. The bone screw of claim 17, configured to engage with a bone plate.

32. The bone screw of claim 17, configured to engage with a tulip.

33. The bone screw of claim 17, further comprising a cage.

* * * * *